(12) United States Patent
Siew et al.

(10) Patent No.: US 12,364,834 B2
(45) Date of Patent: Jul. 22, 2025

(54) NASAL SEAL AND RESPIRATORY INTERFACE

(71) Applicant: Fisher & Paykel Healthcare Limited, Auckland (NZ)

(72) Inventors: Silas Sao Jin Siew, Auckland (NZ); Amit Galgali, Auckland (NZ); Ryan Anthony Graham, Auckland (NZ); Mark Andrew Thompson, Auckland (NZ); Olivia Marie Allan, Auckland (NZ); Bruno Sintive, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 791 days.

(21) Appl. No.: 17/039,512

(22) Filed: Sep. 30, 2020

(65) Prior Publication Data

US 2021/0244906 A1 Aug. 12, 2021

Related U.S. Application Data

(63) Continuation of application No. 14/442,923, filed as application No. PCT/NZ2013/000211 on Nov. 15, 2013, now Pat. No. 10,821,250.

(60) Provisional application No. 61/727,322, filed on Nov. 16, 2012.

(51) Int. Cl.
*A61M 16/06* (2006.01)
*A61M 16/08* (2006.01)

(52) U.S. Cl.
CPC ........ *A61M 16/0666* (2013.01); *A61M 16/06* (2013.01); *A61M 16/0616* (2014.02); *A61M 16/0683* (2013.01); *A61M 16/0825* (2014.02); *A61M 2210/0618* (2013.01)

(58) Field of Classification Search
CPC .............. A61M 16/06; A61M 16/0605; A61M 16/0611; A61M 16/0666; A61M 16/0616; A61M 16/0683; A61M 2210/0618
See application file for complete search history.

(56) References Cited

U.S. PATENT DOCUMENTS

| 1,610,793 A | 12/1926 | Leo |
| 2,353,643 A | 7/1944 | Bulbulian |
| 2,452,722 A | 11/1948 | Boothby et al. |

(Continued)

FOREIGN PATENT DOCUMENTS

| AU | 2005/100738 A4 | 11/2005 |
| AU | 2013345489 | 5/2014 |

(Continued)

OTHER PUBLICATIONS

International Search Report; PCT/NZ2013/000211; dated Apr. 4, 2014; 6 pages.

(Continued)

*Primary Examiner* — Colin W Stuart
*Assistant Examiner* — Douglas Y Sul
(74) *Attorney, Agent, or Firm* — VIA LLP

(57) ABSTRACT

A nasal seal for a respiratory interface comprises a supple lower-nose-receiving center part having a concave shape pre-formed to receive and sealingly contact the tip, lower sides, and base of the nose and sealingly contact the upper lip, and position an aperture for gas flow beneath the nares of wearer. The seal may have resilience or memory towards this preformed shape.

26 Claims, 47 Drawing Sheets

(56) References Cited

U.S. PATENT DOCUMENTS

| | | |
|---|---|---|
| 2,620,794 A | 12/1952 | George |
| 2,881,444 A * | 4/1959 | Fresh ............... A61F 9/026 |
| | | 2/9 |
| 2,970,593 A | 2/1961 | Seeler |
| 3,040,741 A | 6/1962 | Carolan |
| 3,042,035 A | 7/1962 | George |
| 3,065,747 A | 11/1962 | Charles |
| 3,079,917 A | 3/1963 | Godfrey |
| 3,295,529 A | 1/1967 | Stephen et al. |
| 3,530,031 A | 9/1970 | Loew |
| 3,792,702 A | 2/1974 | Delest |
| 3,815,596 A | 6/1974 | Keener et al. |
| 3,824,999 A | 7/1974 | King |
| 3,850,168 A | 11/1974 | Ferguson et al. |
| 3,850,171 A | 11/1974 | Ball et al. |
| 4,033,353 A | 7/1977 | La Rosa |
| 4,454,880 A | 6/1984 | Muto et al. |
| 4,480,639 A | 11/1984 | Peterson et al. |
| 4,513,896 A | 4/1985 | Hirsch |
| 4,753,233 A | 6/1988 | Grimes |
| 4,915,105 A | 4/1990 | Lee |
| 4,947,488 A | 8/1990 | Ashinoff |
| 4,960,121 A | 10/1990 | Nelson et al. |
| 5,237,986 A | 8/1993 | Seppala et al. |
| 5,485,837 A | 1/1996 | Solesbee et al. |
| 5,560,354 A | 10/1996 | Berthon-Jones et al. |
| 5,657,752 A | 8/1997 | Landis et al. |
| 5,676,133 A | 10/1997 | Hickle et al. |
| 5,724,965 A | 3/1998 | Handke et al. |
| 5,832,918 A | 11/1998 | Pantino |
| 5,921,239 A | 7/1999 | McCall et al. |
| 6,019,101 A | 2/2000 | Cotner et al. |
| 6,119,694 A | 9/2000 | Correa et al. |
| 6,338,342 B1 | 1/2002 | Fecteau et al. |
| 6,386,198 B1 | 5/2002 | Rugless |
| 6,418,929 B1 | 7/2002 | Norfleet |
| 6,431,172 B1 | 8/2002 | Bordewick |
| 6,467,483 B1 | 10/2002 | Kopacko et al. |
| 6,470,886 B1 | 10/2002 | Jestrabek-Hart |
| 6,497,232 B2 | 12/2002 | Fecteau et al. |
| 6,561,190 B1 | 5/2003 | Kwok |
| 6,581,594 B1 | 6/2003 | Drew et al. |
| 6,584,977 B1 | 7/2003 | Serowski |
| 6,591,837 B1 | 7/2003 | Byram |
| 6,729,333 B2 | 5/2004 | Barnett et al. |
| 6,892,729 B2 | 5/2005 | Smith et al. |
| 6,928,657 B2 | 8/2005 | Bell et al. |
| 6,951,218 B2 | 10/2005 | Gradon et al. |
| 7,077,139 B2 | 7/2006 | Amante et al. |
| 7,178,525 B2 * | 2/2007 | Matula, Jr. ......... A61M 16/0616 |
| | | 128/207.11 |
| 7,255,106 B2 | 8/2007 | Gallem et al. |
| 7,353,827 B2 | 4/2008 | Geist |
| 7,448,386 B2 | 11/2008 | Ho et al. |
| 7,461,656 B2 | 12/2008 | Gunaratnam et al. |
| 7,493,902 B2 | 2/2009 | White et al. |
| 7,556,043 B2 | 7/2009 | Ho et al. |
| 7,658,189 B2 | 2/2010 | Davidson et al. |
| 7,703,457 B2 | 4/2010 | Barnett et al. |
| 7,743,767 B2 | 6/2010 | Ging et al. |
| 7,753,051 B2 | 7/2010 | Burrow et al. |
| 7,845,352 B2 | 12/2010 | Sleeper et al. |
| 7,856,982 B2 | 12/2010 | Matula, Jr. et al. |
| 7,874,291 B2 | 1/2011 | Ging et al. |
| 7,874,293 B2 | 1/2011 | Gunaratnam et al. |
| 7,896,003 B2 | 3/2011 | Matula et al. |
| 7,931,023 B2 | 4/2011 | Berthon-Jones et al. |
| 7,975,694 B2 | 7/2011 | Ho |
| 7,997,267 B2 | 8/2011 | Ging et al. |
| 8,042,546 B2 | 10/2011 | Gunaratnam et al. |
| 8,061,355 B2 | 11/2011 | Jaffre et al. |
| 8,100,126 B2 | 1/2012 | McAuley et al. |
| 8,118,027 B2 | 2/2012 | Matula, Jr. et al. |
| 8,127,764 B2 | 3/2012 | Ho et al. |
| 8,127,765 B2 | 3/2012 | Ho et al. |
| 8,132,270 B2 | 3/2012 | Lang et al. |
| 8,161,971 B2 | 4/2012 | Jaffe et al. |
| 8,186,352 B2 | 5/2012 | Gunaratnam et al. |
| 8,291,906 B2 | 10/2012 | Kooij et al. |
| 8,297,285 B2 | 10/2012 | Henry et al. |
| 8,371,302 B2 | 2/2013 | Ging et al. |
| 8,397,728 B2 | 3/2013 | D'Souza et al. |
| 8,505,535 B2 | 8/2013 | Jones et al. |
| 8,550,084 B2 | 10/2013 | Ng et al. |
| 8,573,201 B2 | 11/2013 | Rummery et al. |
| 8,573,212 B2 | 11/2013 | Lynch et al. |
| 8,636,007 B2 | 1/2014 | Rummery et al. |
| 8,701,667 B1 * | 4/2014 | Ho .................... A61M 16/0605 |
| | | 128/207.18 |
| 8,950,404 B2 | 2/2015 | Formica et al. |
| 9,032,955 B2 | 5/2015 | Lubke et al. |
| 9,044,564 B2 | 6/2015 | Dravitzki et al. |
| 9,095,673 B2 | 8/2015 | Barlow et al. |
| 9,149,594 B2 | 10/2015 | Kooij et al. |
| 9,517,320 B2 | 12/2016 | Barlow et al. |
| 9,539,403 B2 | 1/2017 | Eves et al. |
| 10,821,250 B2 | 11/2020 | Siew et al. |
| 2003/0196655 A1 | 10/2003 | Ging et al. |
| 2004/0211427 A1 | 10/2004 | Jones et al. |
| 2004/0226566 A1 | 11/2004 | Gunaratnam et al. |
| 2005/0051171 A1 | 3/2005 | Booth |
| 2005/0076912 A1 | 4/2005 | Eifler et al. |
| 2005/0199242 A1 * | 9/2005 | Matula, Jr. ......... A61M 16/0816 |
| | | 128/207.18 |
| 2006/0042629 A1 | 3/2006 | Geist |
| 2006/0169286 A1 | 8/2006 | Eifler et al. |
| 2007/0062536 A1 | 3/2007 | McAuley et al. |
| 2007/0095350 A1 | 5/2007 | Darkin et al. |
| 2007/0125384 A1 * | 6/2007 | Zollinger ........... A61M 16/0816 |
| | | 128/206.24 |
| 2007/0175479 A1 | 8/2007 | Groll |
| 2007/0175480 A1 | 8/2007 | Gradon et al. |
| 2008/0047560 A1 | 2/2008 | Veliss et al. |
| 2008/0092904 A1 | 4/2008 | Gunaratnam et al. |
| 2008/0092906 A1 | 4/2008 | Gunaratnam et al. |
| 2008/0190432 A1 | 8/2008 | Blochlinger et al. |
| 2008/0196727 A1 | 8/2008 | Ho et al. |
| 2008/0210241 A1 | 9/2008 | Schulz et al. |
| 2009/0044808 A1 | 2/2009 | Guney et al. |
| 2009/0078264 A1 | 3/2009 | Martin et al. |
| 2009/0120442 A1 * | 5/2009 | Ho .................... A61M 16/0616 |
| | | 128/206.24 |
| 2009/0139526 A1 | 6/2009 | Melidis et al. |
| 2009/0151729 A1 | 6/2009 | Judson et al. |
| 2009/0151733 A1 | 6/2009 | Welchel et al. |
| 2009/0199856 A1 | 8/2009 | Berlin |
| 2009/0223519 A1 | 9/2009 | Eifler et al. |
| 2010/0000544 A1 | 1/2010 | Blaszczykiewicz et al. |
| 2010/0006101 A1 | 1/2010 | McAuley et al. |
| 2010/0132717 A1 | 6/2010 | Davidson et al. |
| 2010/0192955 A1 | 8/2010 | Biener et al. |
| 2010/0192957 A1 | 8/2010 | Hobson et al. |
| 2010/0229868 A1 | 9/2010 | Rummery et al. |
| 2010/0294281 A1 * | 11/2010 | Ho .................... A61M 16/0633 |
| | | 128/206.24 |
| 2010/0313891 A1 | 12/2010 | Veliss et al. |
| 2010/0319700 A1 | 12/2010 | Ng et al. |
| 2011/0000492 A1 | 1/2011 | Veliss et al. |
| 2011/0067704 A1 * | 3/2011 | Kooij ................ A61M 16/0858 |
| | | 128/207.18 |
| 2011/0126841 A1 | 6/2011 | Matula, Jr. et al. |
| 2011/0146685 A1 * | 6/2011 | Allan ................ A61M 16/06 |
| | | 128/206.26 |
| 2011/0232649 A1 | 9/2011 | Collazo et al. |
| 2011/0240030 A1 | 10/2011 | Ho et al. |
| 2011/0247627 A1 | 10/2011 | Omura et al. |
| 2011/0265796 A1 | 11/2011 | Amarasinghe et al. |
| 2011/0308526 A1 | 12/2011 | Ho et al. |
| 2011/0315141 A1 | 12/2011 | Lavi et al. |
| 2012/0037161 A1 | 2/2012 | Ging et al. |
| 2012/0067349 A1 * | 3/2012 | Barlow ............. A61M 16/0075 |
| | | 128/205.25 |
| 2012/0132209 A1 | 5/2012 | Rummery et al. |

(56) References Cited

U.S. PATENT DOCUMENTS

| | | |
|---|---|---|
| 2012/0138060 A1 | 6/2012 | Barlow |
| 2012/0152255 A1 | 6/2012 | Barlow et al. |
| 2012/0204880 A1* | 8/2012 | Smith .................. A61M 16/06 128/206.24 |
| 2012/0216812 A1 | 8/2012 | Pastoor et al. |
| 2012/0222680 A1 | 9/2012 | Eves et al. |
| 2012/0266890 A1 | 10/2012 | Baecke et al. |
| 2012/0304999 A1 | 12/2012 | Swift et al. |
| 2012/0318270 A1 | 12/2012 | McAuley et al. |
| 2013/0000648 A1 | 1/2013 | Madaus et al. |
| 2013/0037030 A1 | 2/2013 | Matula, Jr. |
| 2013/0133664 A1* | 5/2013 | Startare ............. A61M 16/0666 128/206.24 |
| 2013/0139822 A1 | 6/2013 | Gibson et al. |
| 2013/0152937 A1 | 6/2013 | Jablonski |
| 2013/0213400 A1* | 8/2013 | Barlow ............. A61M 16/0616 128/205.25 |
| 2013/0220327 A1 | 8/2013 | Barlow et al. |
| 2013/0319422 A1 | 12/2013 | Ho et al. |
| 2014/0026890 A1 | 1/2014 | Haskard et al. |
| 2014/0053844 A1 | 2/2014 | Rummery et al. |
| 2014/0060544 A1 | 3/2014 | Matula, Jr. et al. |
| 2014/0073847 A1 | 3/2014 | Mujwid et al. |
| 2014/0150798 A1 | 6/2014 | Fong et al. |
| 2014/0166018 A1 | 6/2014 | Dravitzki et al. |
| 2014/0174448 A1 | 6/2014 | Dravitzki et al. |
| 2014/0190486 A1 | 7/2014 | Dunn et al. |
| 2014/0209098 A1 | 7/2014 | Dunn et al. |
| 2014/0238402 A1 | 8/2014 | Austin et al. |
| 2015/0090268 A1 | 4/2015 | Madaus et al. |
| 2015/0128953 A1 | 5/2015 | Formica et al. |
| 2015/0151071 A1 | 6/2015 | Moger et al. |
| 2015/0174355 A1 | 6/2015 | Willard et al. |
| 2015/0182719 A1 | 7/2015 | Grashow et al. |
| 2015/0290415 A1 | 10/2015 | Dunn |
| 2015/0328423 A1 | 11/2015 | Siew et al. |
| 2015/0352307 A1 | 12/2015 | Rutan |

FOREIGN PATENT DOCUMENTS

| | | |
|---|---|---|
| AU | 2018211236 | 7/2020 |
| CN | 101861181 | 10/2010 |
| CN | 102648018 | 8/2012 |
| CN | 102665810 A | 9/2012 |
| EP | 1057494 A2 | 12/2000 |
| EP | 1488820 A2 | 12/2004 |
| EP | 1163923 A2 | 12/2011 |
| EP | 2444113 A2 | 4/2012 |
| EP | 2481435 A2 | 8/2012 |
| EP | 2919842 | 9/2015 |
| GB | 377926 A | 8/1932 |
| GB | 823887 A | 11/1959 |
| GB | 826198 A | 12/1959 |
| GB | 880942 A | 10/1961 |
| GB | 974960 A | 11/1964 |
| GB | 1049604 A | 11/1966 |
| GB | 2367757 A | 4/2002 |
| GB | 2522582 | 9/2019 |
| WO | WO 1993/021788 A1 | 11/1993 |
| WO | WO 1997/000092 A1 | 1/1997 |
| WO | WO 1997/048432 A1 | 12/1997 |
| WO | WO 98/04310 A1 | 2/1998 |
| WO | WO 2002/11804 A2 | 2/2002 |
| WO | WO 2004/073778 A1 | 9/2004 |
| WO | WO 2005/094928 A1 | 10/2005 |
| WO | WO 2007/022562 A1 | 3/2007 |
| WO | WO2007/064665 | 6/2007 |
| WO | WO 2008/007985 A1 | 1/2008 |
| WO | WO 2009/026627 A1 | 3/2009 |
| WO | WO 2009/052560 A1 | 4/2009 |
| WO | WO 2009/144695 A1 | 12/2009 |
| WO | WO 2010/131189 A1 | 11/2010 |
| WO | WO 2010/135785 A1 | 12/2010 |
| WO | WO 2010/139014 | 12/2010 |
| WO | WO 2011/062510 A1 | 5/2011 |
| WO | WO 2011/142678 A1 | 11/2011 |
| WO | WO 2012/020359 | 2/2012 |
| WO | 2012025843 A1 | 3/2012 |
| WO | WO 2012/028995 A1 | 3/2012 |
| WO | WO 2012/045127 A1 | 4/2012 |
| WO | WO 2012/052902 A2 | 4/2012 |
| WO | WO 2012/055886 A1 | 5/2012 |
| WO | WO 2013/006065 A1 | 1/2013 |
| WO | WO 2013/071359 A1 | 5/2013 |
| WO | WO 2013/170290 A1 | 11/2013 |
| WO | WO 2014/013371 | 1/2014 |
| WO | WO 2014/015382 A1 | 1/2014 |
| WO | WO 2014/015383 A1 | 1/2014 |
| WO | WO 2014/021722 | 2/2014 |
| WO | WO 2014/110622 A1 | 7/2014 |
| WO | WO 2014/110626 A1 | 7/2014 |
| WO | WO 2014/124323 A1 | 8/2014 |
| WO | WO 2014/181214 A1 | 11/2014 |
| WO | WO 2014/183167 | 11/2014 |
| WO | WO 2014/077708 | 5/2015 |
| WO | WO 2015/070289 A1 | 5/2015 |

OTHER PUBLICATIONS

Written Opinion of the ISA; PCT/NZ2013/000211; dated Apr. 4, 2014; 5 pages.
Australian Examination Report; dated Jun. 29, 2017; 4 pages.
GB Examination Report; GB1508505.3; dated Sep. 26, 2018; 3 pages.
UK Examination Report; Application No. GB1508505.3, dated May 1, 2019; 4 pages.
UK Combined Search and Examination Report, Application No. GB1909174.3, dated Jul. 11, 2019, in 3 pages.
China National Intellectual Property Administration, Notification of the First Office Action, Application No. 201810056771.0, dated Jan. 17, 2020.
European Patent Office, Examination Report, Application No. 13 854 902.7-1122, dated Mar. 10, 2020, in 14 pages.
Chinese Examination Report for Application No. 2018 10056771.0 dated Sep. 25, 2020, 9 pages.

* cited by examiner

NASAL SEAL AND RESPIRATORY INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

FIELD OF THE INVENTION

The invention generally relates to a nasal seal for a respiratory interface, and to an interface including the nasal seal, comprising either a mask or a mask and headgear.

BACKGROUND OF THE INVENTION

Respiratory interfaces are used to provide respiratory gas or gases, such as air in CPAP therapy, to a user under positive pressure. A nasal interface delivers gas to the nose.

The seal of an indirect nasal interface contacts the upper lip, the face on either side of the nose, and the bridge of the nose, and substantially encloses the nose. An indirect nasal interface may be relatively large on the face, may put pressure on the bridge of the nose, and the frame of the interface may include a T-piece connecting to headgear at the wearer's forehead which typically obstructs also wearing spectacles for example.

A direct nasal interface is typically smaller on the face, and does not comprise a T-piece, and is thus less obstructive. However a direct nasal interface typically comprises nasal pillows or similar which enter into the nares of the wearer to ensure an effective seal.

SUMMARY OF THE INVENTION

An object of the invention is to provide a nasal seal and/or interface which is improved in at least one or more respects or at least provides the public or the medical profession with a useful choice.

In broad terms in one aspect the invention comprises a nasal seal for a mask interface, or a mask interface comprising a nasal seal, the seal comprising a face contacting or wearer side comprising a supple lower nose-receiving center part having a concave shape pre-formed to receive and sealingly contact the tip, lower sides, and base of the nose and sealingly contact the upper lip, and position an aperture for gas flow beneath the nares of wearer, the supple center part comprises left and right side wall portions on left and right sides of the aperture to contact the left and right lower sides of the nose of the wearer, wherein the left and right side wall portions or at least upper sections of the left and right side wall portions have an outwardly projecting or convex shape (away from an interior of the seal) on opposite sides of the seal, and wherein the seal comprises an outward side of the seal opposite the wearer side, which outward side of the seal comprises left and right stabilising outer parts which terminate in left and right outer tips adapted to contact the face adjacent the lower flanks of the nose on the left and right sides of the nose when worn, said left and right outer parts of the seal being less flexible or stiff relative to at least the center part of the wearer side of the seal.

The left and right side wall portions of the supple center part of the seal extend from the aperture away from one another. In at least some embodiments the outwardly projecting or convex shape of the left and right side wall portion or the upper sections of the left and right side wall portions are arranged to seal against the crease or recess at the junction between the bottom of the sides of the nose and the face. These outwardly projecting or convex upper sections on opposite sides of the seal are typically above the aperture in a height of the seal.

In at least some embodiments the outward side of the seal connects to upper, lower, and outer tip peripheral parts of the wearer side of the seal with a wall thickness which reduces from that of the external side of the seal to the wearer side of the seal. In at least some embodiments left and right peripheral parts of the seal at left and right outer tips of the seal which contact the face when worn include an approximately straight part bridging upper and lower peripheral parts of the seal.

Typically a lower edge of the aperture is spaced rearwardly in a depth of the seal relative to an upper edge of the aperture.

In at least some embodiments the seal has a hollow interior which is filled with air under positive pressure in use, at least on an internal side of the supple lower-nose-receiving concave center part of the wearer side of the seal.

Typically the supple lower-nose-receiving concave center part has resilience or memory towards said pre-formed shape.

In at least some embodiments the center part comprises an upper wall portion above the aperture to contact the tip of the nose of the wearer, and a lower wall portion below the aperture and rearward of the upper wall portion to contact the upper lip below the nose of the wearer.

In at least some embodiments the upper wall portion, the lower wall portion, and the left and right side wall portions may have complex curved shapes (and to the extent each has an approximate major plane these are not coplanar).

The supple upper wall, lower wall, and side wall portions of the center of the wearer side of the seal have a shape pre-formed to receive and sealingly contact the tip, lower sides, and underside of the nose of the wearer. The supple center part of the wearer side of the seal may have this pre-formed shape when not under positive air pressure from within the seal. While supple and thus flexibly conformable, in at least preferred embodiments it also has resilience or memory towards this pre-formed shape. In other words the seal has 'structure' because it maintains this pre-formed shape. Thus for many wearers the seal will naturally fit, or conform with only a relatively small amount of shape alteration or deformation, to the shape of these parts of the nose of the wearer, even before internal gas flow through the seal creates a positive pressure within the seal. Internal gas flow pressure within the seal will press the seal against these parts of the nose of the wearer. For other wearers internal gas flow pressure within the seal will also cause the seal to alter shape to a greater extent to conform against the shape of the nose of the wearer.

The seal does not seal against the bridge of the nose. The seal preferably does not extend, at least to any significant extent such as more than about 1 cm for example, over any flat part of ridge cartilage of the nose between the tip and the bridge.

In at least some embodiments the upper wall portion of the supple center part of the wearer side of the seal includes an upper concave section (within the greater general concavity of the supple central part of the wearer side of the seal) to receive specifically the tip of the nose, which is concave in both a height and a width of the seal. This upper concave section may have an intermediate wall thickness greater than the balance of the center part of the wearer side of the seal but less than left and right outer stabilising parts of the wearer side of the seal or less than an outward side of the seal. It may extend from an upper edge of the seal outlet aperture to at or towards an upper periphery of the seal.

In at least some embodiments the wearer side of the seal also comprises left and right outer stabilising parts outward of the left and right side wall portions of the supple center part, to contact the wearer's face adjacent the lower flanks of the nose on the left and right sides of the nose, and which are flexible or supple but relatively less so (or are relatively stiffer) than the more supple lower-nose-receiving center part of the wearer side of the seal. For example these left and right outer stabilising parts may have a thicker wall section than a wall section of the lower-nose-receiving center part.

The seal may be proportioned so that a junction or change in wall thickness on either side of the seal between an inner edge of these left and right outer stabilising parts and the supple center part of the seal sits at or adjacent the junction between the lower sides of the nose and the face adjacent the nose.

The left and right outer parts of the outward side of the seal may be relatively less flexible than both the lower-nose-receiving center part and the left and right outer stabilising parts of the wearer side of the seal. For example the left and right outer parts of the external side of the seal may have a greater wall thickness than both the center part and the left and right stabilising parts of the wearer side of the seal. The hollow interior of the seal may extend to between the left and right outer or side parts of the outward and wearer sides of the seal.

An interface of which the seal may comprise a part may include a frame to which the seal is attached. In at least some embodiments the seal and the frame together form an enclosure having a gas flow inlet opening to the respiratory system and an aperture through the seal to the wearer In a preferred embodiment the frame comprises side arms which extend outwardly (away from each other) and rearwardly past left and right extremities of the seal, to extend upwardly at a shallow angle and along the left and right cheeks and in particular cheekbones of a wearer, to connect to headgear for holding the seal on the face of a wearer. Such side arms may be longer than they are deep or thick and may be resiliently flexibly connected to a central part of the frame and/or resiliently flexible along their length, and may extend to a location between the ears and eyes of the wearer and/or to approximately the temple of the wearer, where the side arms connect to headgear. The shape of the frame side arms and/or angle between the frame side arms is such that the side arms rest on the left and right cheeks and in particular cheekbones of a wearer to assist in stabilising the interface against rotation about a horizontal axis when worn.

At their outer ends the side arms comprise connector parts for detachably connecting the frame to headgear. In a preferred form the end of each frame side arm comprises a hook and in particular an upwardly open hook part, for entering into a loop of the headgear.

In preferred embodiments the interface does not comprise a T-piece from the frame upwardly (when worn) to connect to headgear at the wearer's forehead.

In one embodiment headgear suitable for use with an interface assembly of the invention comprises a rear strap to extend around a rear part of the head of a wearer and a top strap to extend over the top of a head of a wearer. The rear strap may extend around a lower rear part of the head of the wearer and in particular over a lower part of the occipital bone. The top strap may be a crown strap or a forehead strap.

The seal of the invention comprises less flexible left and right stabilising outer parts adapted to contact the face adjacent the lower flanks of the nose on the left and right sides of the nose when worn. The seal has enhanced stability against rotation on the face due for example to tube drag forces, which can break the seal and cause leakage, as do preferred embodiments of interfaces comprising the seal and with side arms as described, even though the seal does not seal against the sensitive bridge of the nose or extend, at least to any significant extent such as more than about 1 cm for example, over any flat part of ridge cartilage of the nose between the tip and the bridge. The seal also enables a nasal interface to be smaller than an indirect nasal interface which substantially encloses the nose and may be relatively large on the face, and also does not require the pillows or similar of a conventional direct nasal interface which protrude into the nares of the wearer. The center of the wearer side of the seal has a shape pre-formed to receive and sealingly contact the tip, lower sides, and underside of the nose of the wearer, and sealingly contact the upper lip of the wearer below the nose. At the same time this center part of the seal is supple so that internal gas pressure will press the seal against these parts of the nose to enhance the seal, and so that the seal will further conform to the shape of these parts of the nose (for many wearers with only a relatively small amount of shape alteration or deformation). Despite being supple the seal also has resilience or memory towards, so as to hold, this preformed shape. Also, because the seal has this preformed shape to receive and contact the lower parts of the nose of the wearer and the upper lip the seal may be effective at relatively low gas flow rates through the mask which create only a relatively low internal gas pressure within the seal against the nose, such as flow rates below about 4 cm H2O for example. The left and right side wall portions, or at least upper sections of the left and right side wall portions of the supple center of the wearer side, have an outwardly projecting or convex shape (away from an interior of the seal) on opposite sides of the seal. These outwardly projecting or convex upper sections on opposite sides of the seal contact the crease or recess at the junction between the bottom of the sides of the nose and the face, and assist in avoiding upward leakage of air pressure, towards the eyes, in this area. Under gas pressure within the seal they deform (push) outwardly against the face in this area to enhance this seal.

Also, because the seal in at least preferred embodiments maintains its shape or structure even when not worn or under internal gas pressure, it is relatively visually apparent to a user how to place or position the mask on the face when a user first begins use of a mask comprising the seal of the invention. It is relatively apparent from its shape how to position an indirect nasal mask on the face, and also for a direct nasal interface which comprises nasal pillows or similar which enter into the nares of the wearer, but it may not be immediately apparent at least to some new users, for a mask with a seal which engages only the lower part of the nose but without covering the nose and without parts that enter the nose, and the pre-formed shape of the seal of the invention makes how the seal and thus mask should be positioned on the face more apparent for a mask of this type. Thus the mask may be more intuitive to use.

Other

The seals may be useful in respiratory interfaces particularly for CPAP therapy, at air pressures in the range about 0.5 to about 30 cm H2O for example.

DEFINITIONS

In this specification the terms "wearer" or "user" means persons of or in a range of average adult size(s).

In this specification the terms "height", "width", and "depth" in relation to the interface, mask, or seal mean approximately vertical, transversely horizontal, and front to back horizontal through or in relation to the interface, mask, or seal when worn by a user standing upright.

In this specification the term "concave" means a recess (or recessed) of any shape and not solely mathematically convex, and "convex" has a similar meaning.

In this specification the term "comprising" means "consisting at least in part of". When interpreting a statement in this specification and claims that includes "comprising", features other than that or those prefaced by the term may also be present. Related terms such as "comprise" and "comprises" are to be interpreted similarly.

Reference to any prior art in this specification is not, and should not be taken as, an acknowledgement or any form of suggestion that that prior art forms part of the common general knowledge in the field of endeavour in any country in the world.

BRIEF DESCRIPTION OF THE DRAWINGS

Embodiments of the invention are described with reference to the accompanying drawings, by way of example and without intending to be limiting, in which.

DETAILED DESCRIPTION OF EMBODIMENTS

Overview

Figure 1:
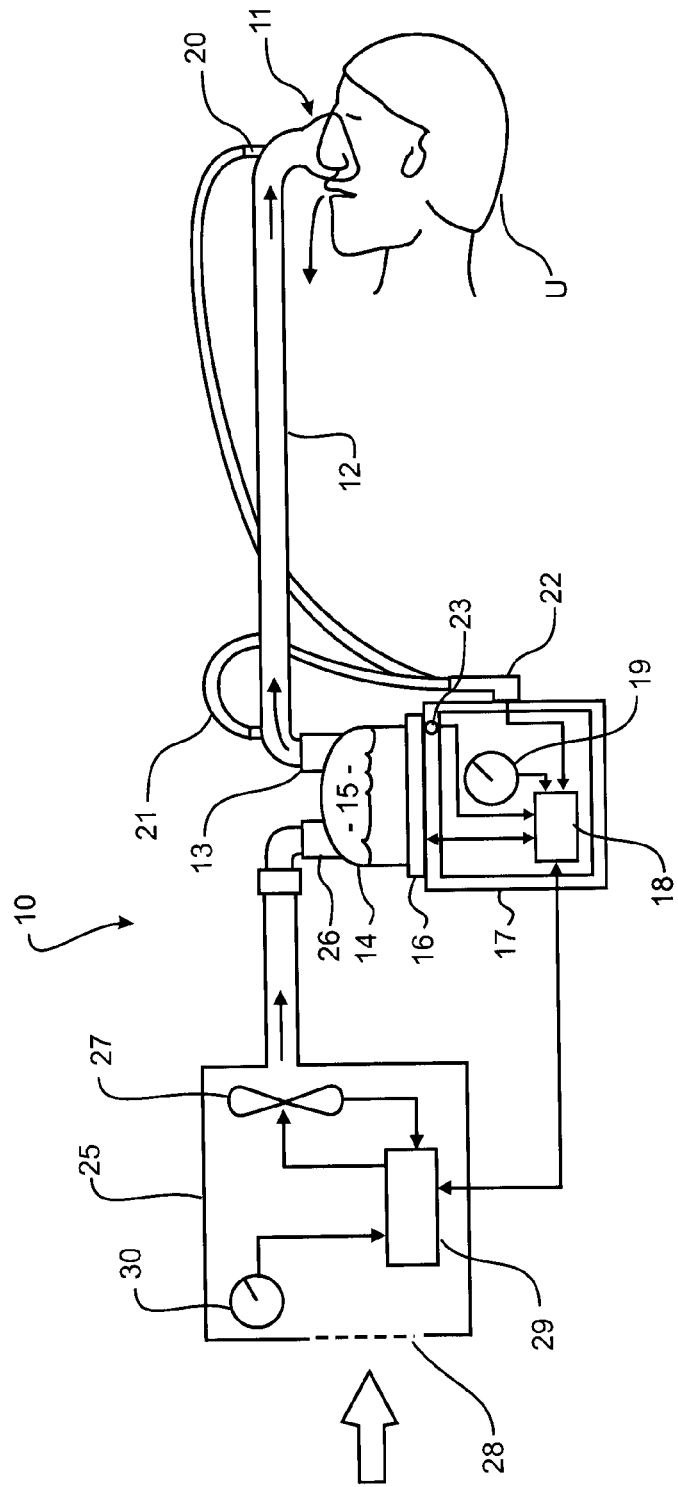
FIG. 1 is a schematic diagram of a system for providing a heated humidified gases stream to a user, such as a continuous positive airway pressure system.

FIG. 1 is a schematic diagram of a continuous positive airway pressure (CPAP) system 10 for providing a heated and humidified air stream to a user U through an interface 11 worn by the user, and which is connected to CPAP system 10 by a conduit or tube 12.

A humidification chamber 14 has a heat conductive base in contact with a heater plate 16 of humidifier 17 to humidify the air stream. Conduit 12 is connected to an outlet 13 of humidification chamber 14 to convey humidified air to the user interface 11. The humidifier 17 comprises a controller 18, such as a microprocessor-based controller that executes computer software commands stored in an associated memory, for example but without limitation. The controller 18 receives input commands from multiple sources, including a user input interface 19 such as a dial or touch screen, which enables the setting of a predetermined value of humidity, temperature, or other characteristic of the humidified air supplied to the user U. The controller 18 also may receive input from one or more other sources, such as for example temperature and/or flow velocity sensors 20 and 21, which are connected through a connector 22 to communicate with controller 18, and/or a heater plate temperature sensor 23. In response to the user set humidity or temperature value the controller 19 determines when and/or to what level the heater plate 16 should be energized to suitably heat the water contained in the humidification chamber 14.

As the volume of water in the chamber is heated, water vapour begins to fill the volume of the chamber above a surface of the water. The water vapour passes out of the outlet 13 of the humidification chamber with a flow of air that is provided from a supply 25 such as a blower 27, which enters the humidification chamber 30 through an inlet 26. The blower 27 can be variable in speed fan, or can include a variable pressure regulator. The blower 27 draws air through an inlet 28. The blower can be controlled by controller 29 or controller 18 for example. The controller may control blower speed, regulated pressure, or the like according to any suitable criteria. For example, the controller may respond to inputs from controller 18 and a user set value (e.g., a preset value) of pressure and/or fan speed, which can be set with a user interface 30 (e.g., a dial).

The conduit 12 may comprise a heater such as a heater wire for example, to heat the walls of the conduit to reduce condensation of humidified gases within the conduit.

The seal and interfaces of the invention can be used in such a CPAP system as described whether humidified or not, or alternatively in other forms of respiratory systems, such as for example VPAP (Variable Positive Airway Pressure) systems, BiPAP (Bi level Positive Airway Pressure) systems, or with a ventilator, and are described herein generally with reference to CPAP therapy by way of example only.

Figure 2:
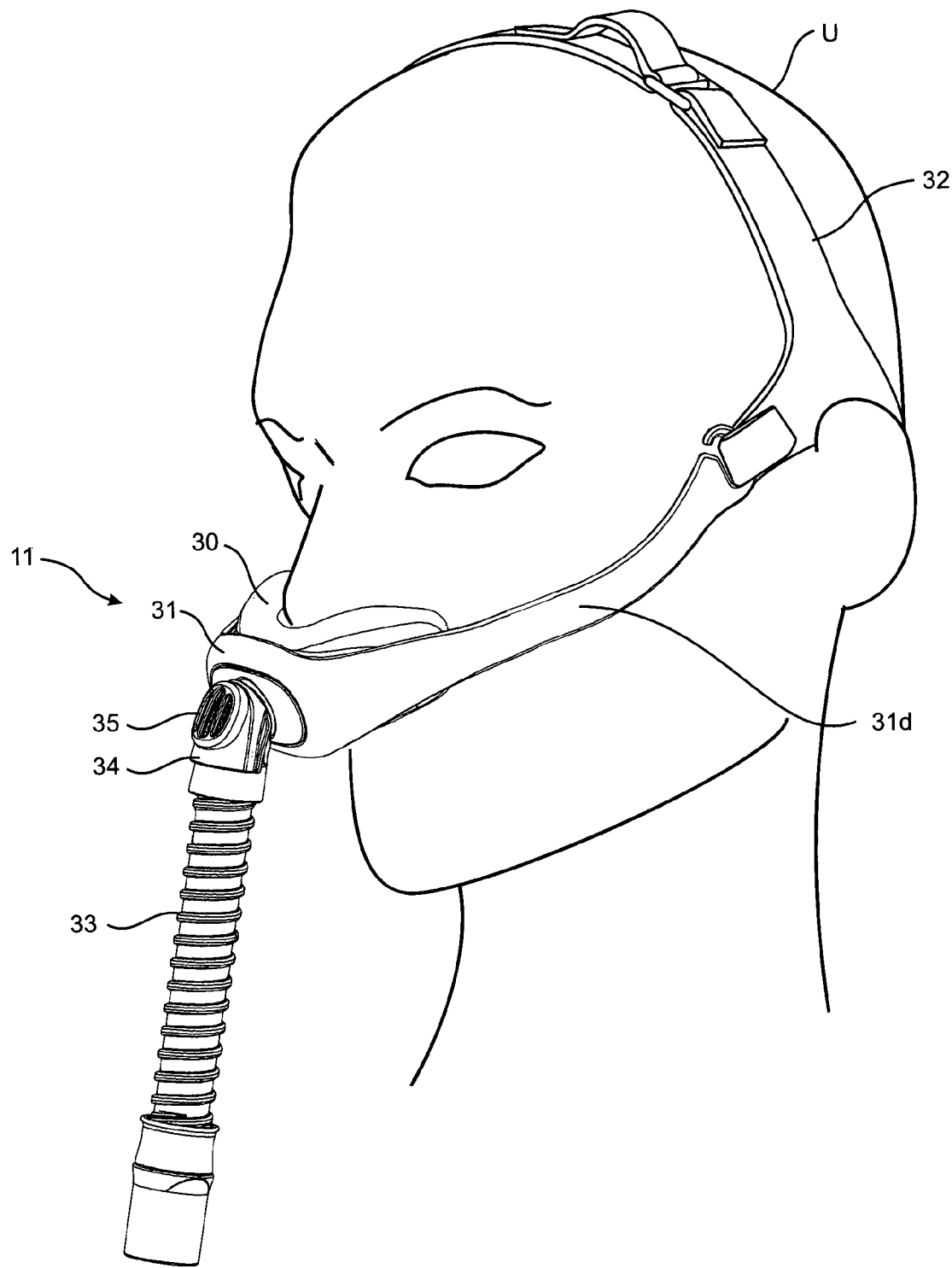
FIG. 2 is a perspective view of a person wearing a patient interface of an embodiment of the invention.
Figure 3:
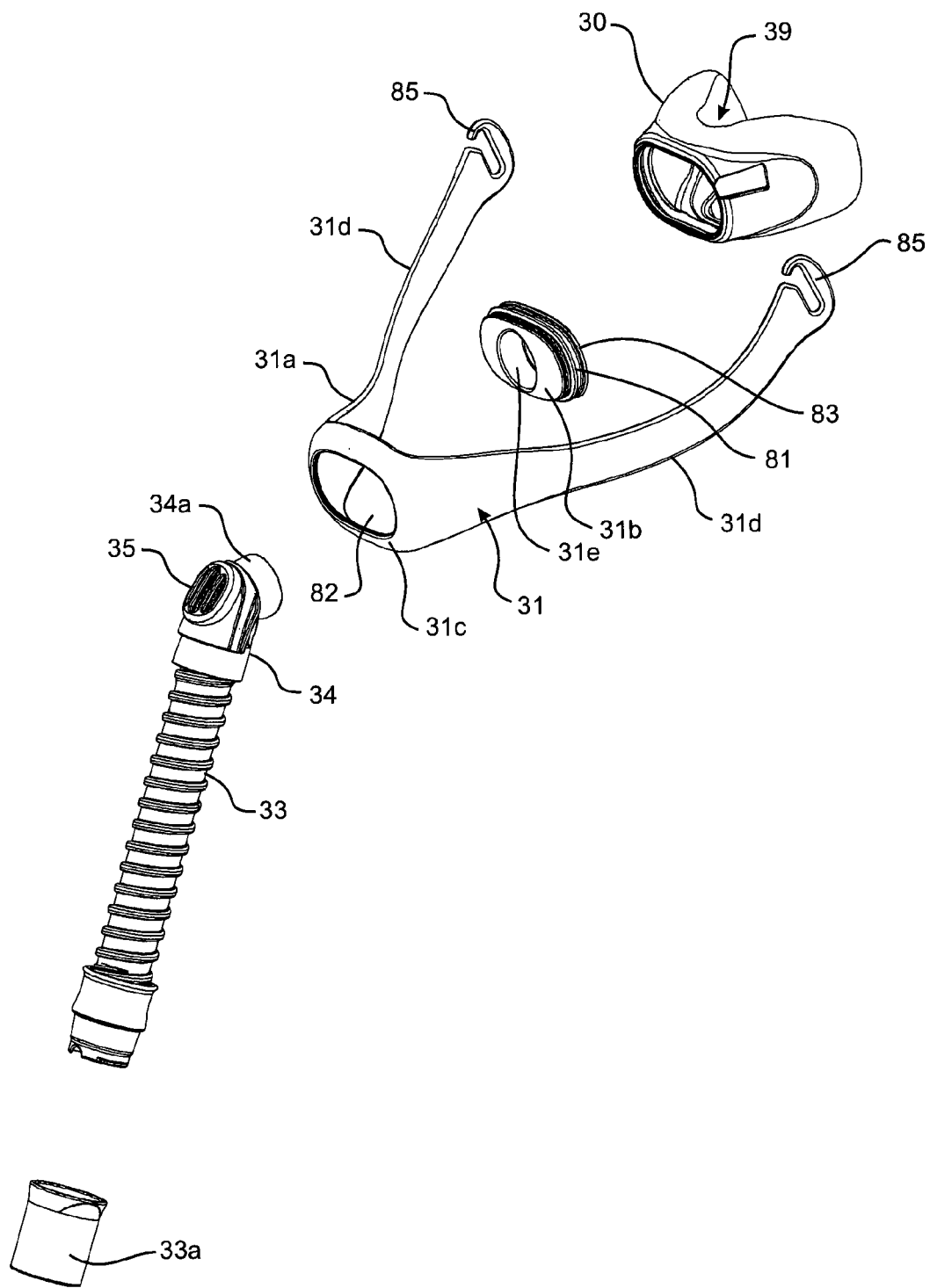
FIG. 3 is an exploded view illustrating the components making up the interface of FIG. 2.

FIG. 2 is a perspective view of user U wearing an interface 11 of an embodiment of the invention, and FIG. 3 is an exploded view illustrating the components of the interface. The interface comprises a mask including a seal 30 and a frame 31. The interface also includes headgear 32 for securing the mask to the wearer. Typically the interface also comprises a short flexible supply conduit or tube 33 from the mask such as from a central connection at the front of the mask, which connects to the supply conduit 12 of the CPAP or other respiratory system. The conduit 33 may connect to the mask via a hollow elbow 34, which may swivel relative to the frame so that the path of the conduit relative to the positioning of the mask on the face of the patient can adapt to the sleeping position of the patient.

The mask may include a limited flow outlet (or bias flow outlet) 35 for providing gas washout from the interface. The outlet 35 may be in the form of a collection of small apertures. The outlet may be provided in the elbow 34 as shown, in the frame, or elsewhere on the interface.

Seal

FIGS. 5 to 12 show an embodiment of a seal. As stated a face contacting or wearer side of the seal comprises a supple lower-nose-receiving concave center part 39 (see particularly FIG. 5) pre-formed in shape to form a seal on the face of the wearer by receiving and sealingly contacting the tip, lower sides, and base of the nose and sealingly contacting the upper lip, and position an aperture 40 for gas flow beneath the nares of wearer. The lower-nose-receiving supple center part comprises an upper wall portion 41 to contact the tip of the nose of the wearer, an inwardly spaced lower wall portion 42 to contact the upper lip below the nose of the wearer, and left and right side wall portions 43 and 44 to contact the left and right lower sides of the nose of the wearer.

Figure 5:
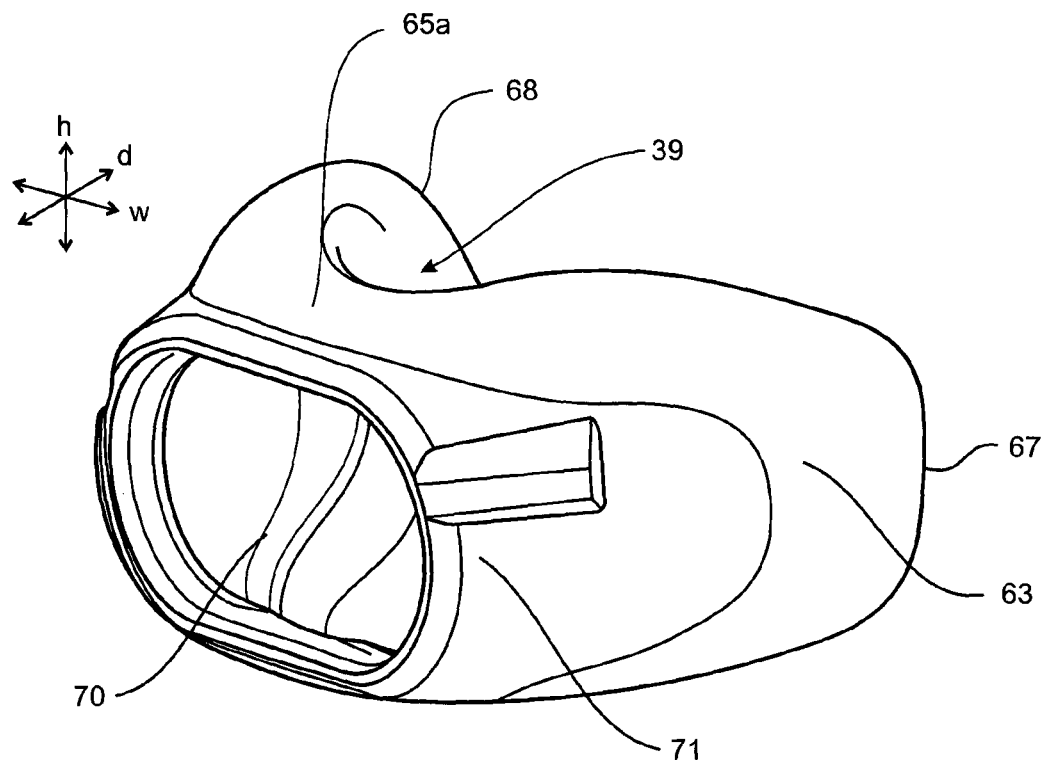
FIG. 5 is a perspective view of an embodiment of a seal.
Figure 6:
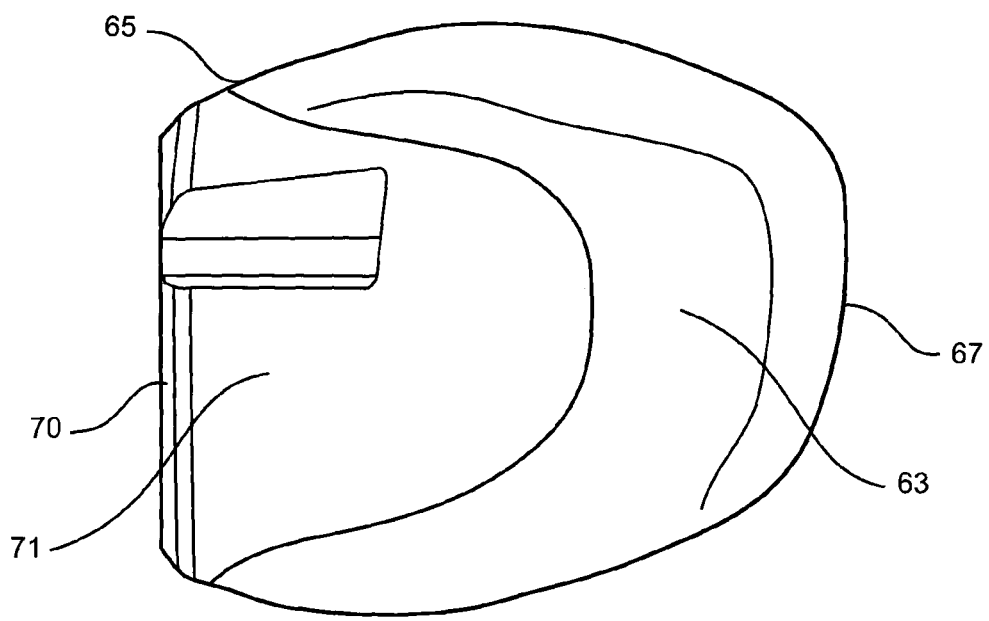
FIG. 6 is a side view of the seal.
Figure 7:
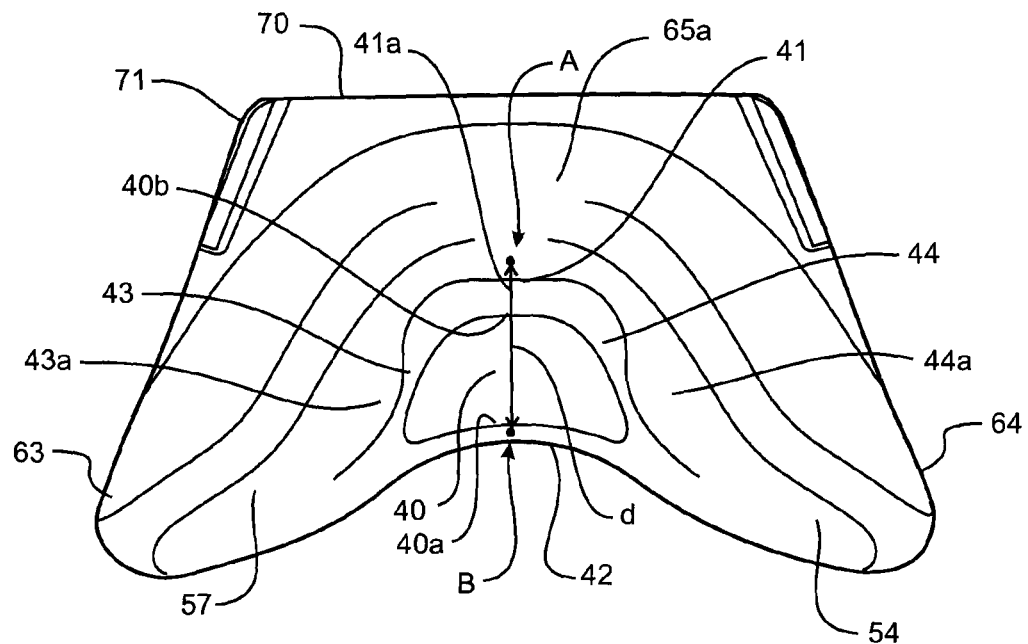
FIG. 7 is a top view of the seal.
Figure 8:
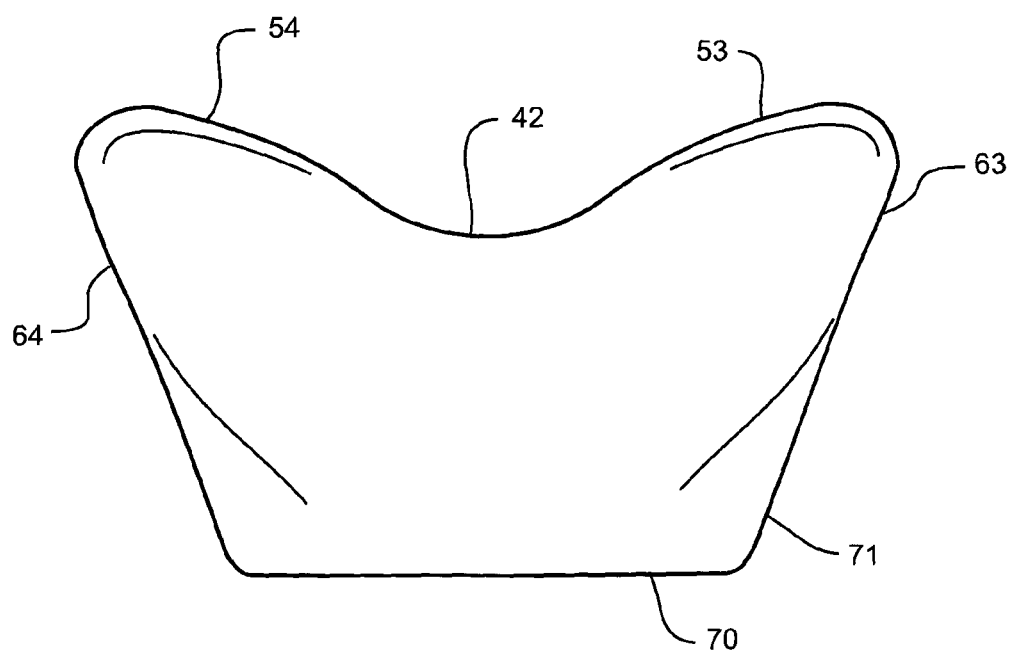
FIG. 8 is an underside view of the seal.
Figure 9:
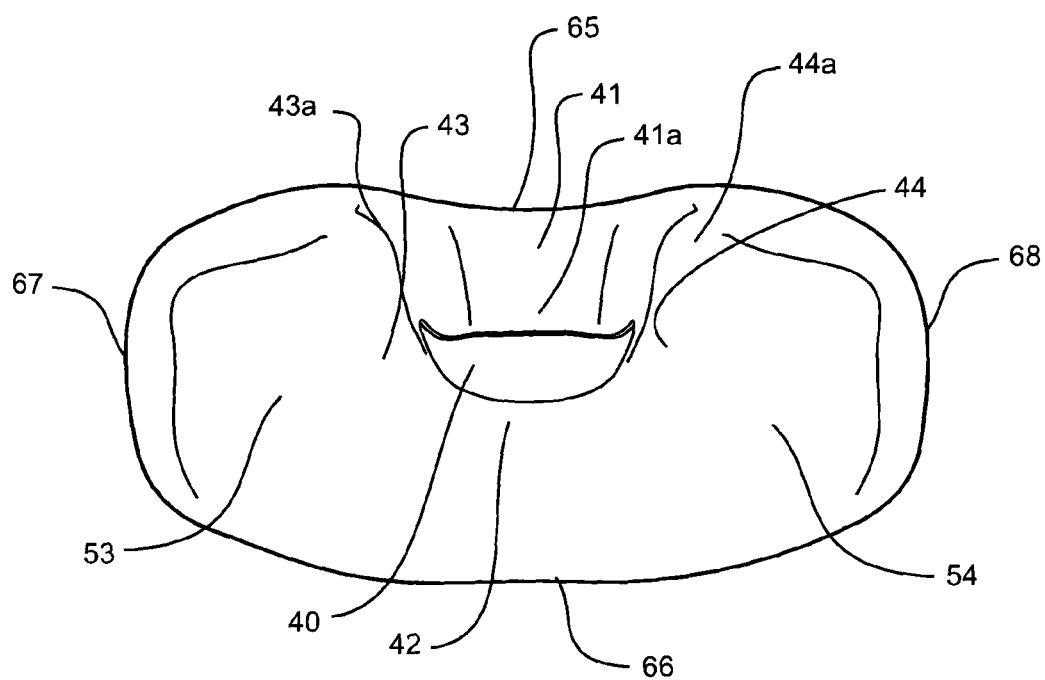
FIG. 9 is a view of the wearer side of the seal.
Figure 10:
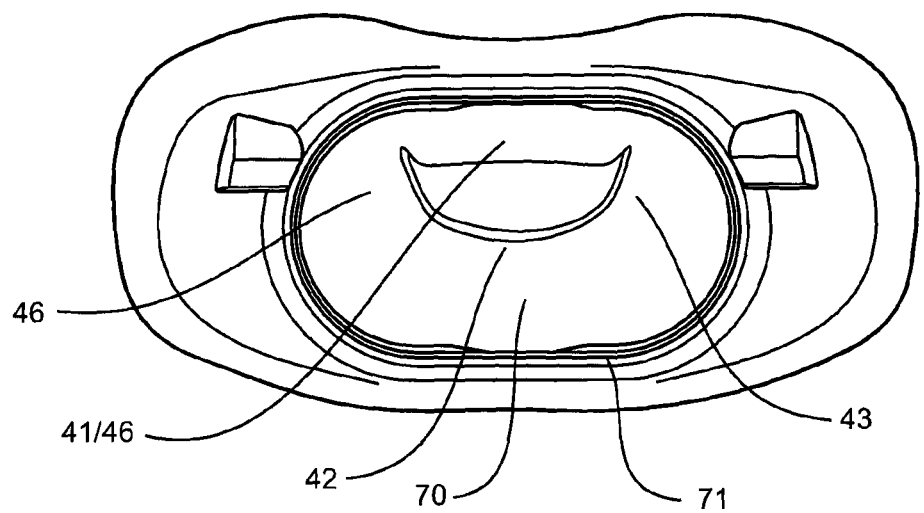
FIG. 10 is a view of the external side of the seal.

The upper and lower wall portions 41 and 42 are each symmetrical about separate axes A and B (see FIG. 6) in a height h of the seal (see FIG. 5). These axes A and B spaced from each other in a depth d of the seal by for example between about 1 to about 3 cm or about 1.5 to about 2.5 cm. Alternatively stated the lower wall portion 42 below the outlet aperture is closer to the left and right rearward-most extremities of the seal than is the upper wall portion 41. The left and right side wall portions 43 and 44 extend from the aperture 40 away from one another. An angle between the left and right side wall portions 43 and 44 may be between about 20 and about 60 degrees or about 30 and about 50 degrees for example.

A lower edge 40a of the aperture 40 is spaced rearwardly in the depth of the seal relative to an upper edge 40b of the aperture.

In at least preferred embodiments the seal has a hollow interior which is filled with air under positive pressure in use.

The supple lower-nose-receiving concave center part even has a thin wall thickness such as a wall thickness in the range about 0.1 to about 0.5 mm, or about 0.1 to about 0.3 mm, or about 0.2 to about 0.3 mm, for example. At the same time and while supple and flexibly conformable, in at least preferred embodiments it also has resilience or memory towards this shape so that it has or maintains this pre-formed shape even when not under positive air pressure from within the seal.

The material from which at least the thin-walled supple center portion of the seal is formed may be a soft stretchable material such as a silicone material, or alternatively a TPE (thermoplastic elastomer) for example. In preferred forms the seal is a one piece component all of the described parts and portions of which are integrally formed, for example from such a material, by injection moulding for example. In an alternative embodiment however only a wearer side of the seal may be formed of such a material, and may be bonded to a more rigid shell which couples to or is integrally formed with a frame of the interface. Alternatively the seal may be a foam or gel-filled seal.

Typically the seal is wider in a width of the seal than it is higher in a height of the seal. In at least some embodiments the seal may have an overall width of between about 5 and about 10 cm, or about 6 cm and about 8 cm. In at least some embodiments the seal may have an overall height of less than about 5 cm, or less than about 4.5 cm.

The aperture 40 may be elongate in a width of the seal. The aperture 40 may be approximately trapezium-shaped in plan view (viewed from above). In at least some embodiments at least a part of a periphery of the aperture comprises a rim thickened on the interior of the seal.

Figure 4A:
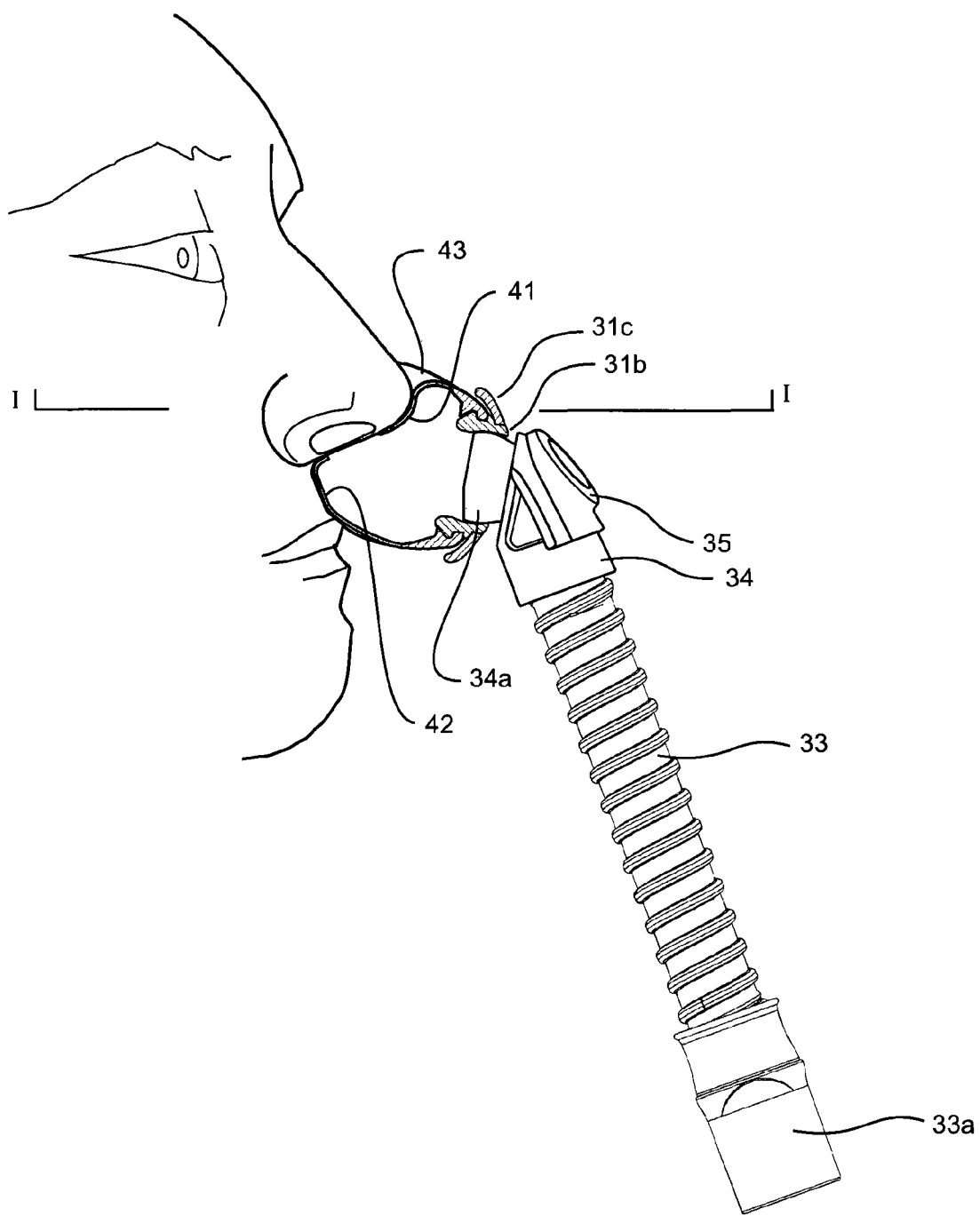
FIG. 4A is a vertical cross-section view.
Figure 4B:
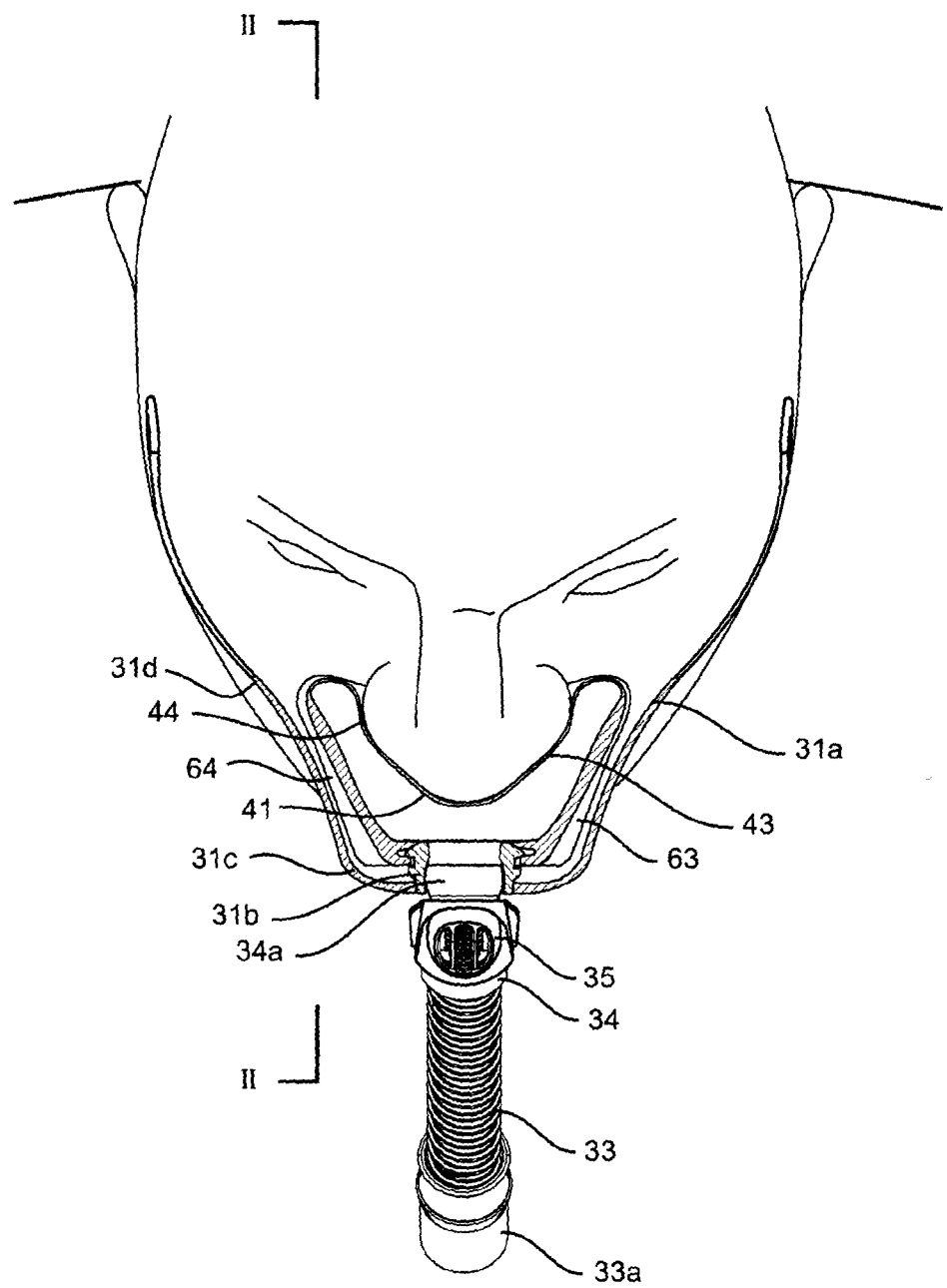
FIG. 4B is a horizontal cross-section view along line I-I of FIG. 4A.
Figure 4C:
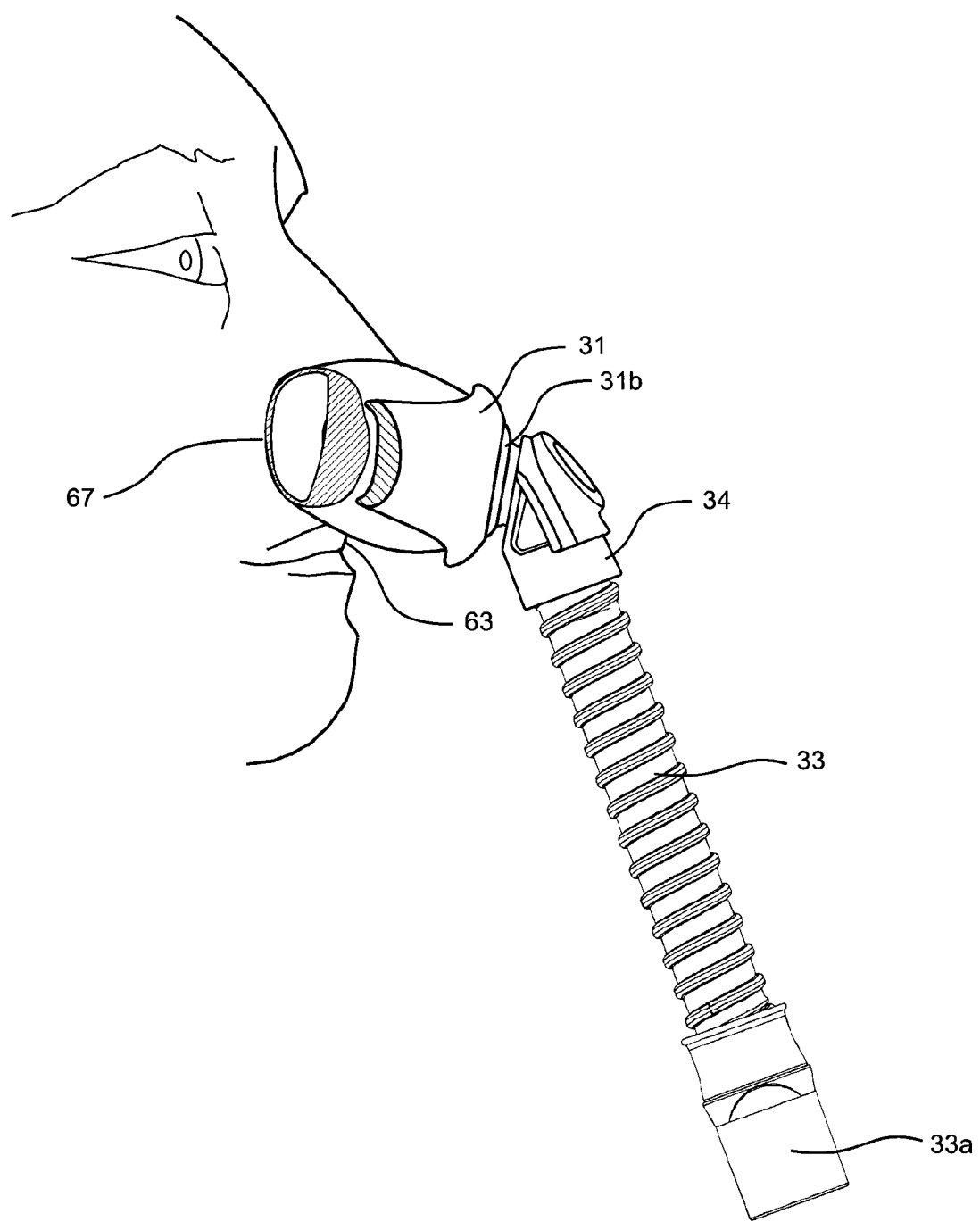
FIG. 4C is a vertical cross-section view along line II-II of FIG. 4B, and of the interface of FIGS. 2 and 3 worn by a patient and with a positive pressure airflow through the interface.

FIG. 4A is a vertical cross-section view, FIG. 4B is a horizontal cross-section view along line I-I of FIG. 4A, and FIG. 4C is a vertical cross-section view along line II-II of FIG. 4B, of an interface (the interface of FIGS. 2 and 3) comprising the seal thus described, worn by a user and with a positive pressure airflow through the interface. The pre-formed shape defined between supple upper wall, lower wall, and side wall portions 41-44 of the center of the wearer side of the seal receives and sealingly contacts the tip, lower sides, and underside of the nose of the wearer (see particularly FIGS. 4A & B). For many wearers the seal will naturally fit or conform with only a relatively small amount of shape alteration or deformation to the shape of these parts of the nose of the wearer, without or before internal gas flow positive pressure. Internal gas flow pressure within the seal will press the seal against these parts of the nose of the wearer. For other wearers internal gas flow pressure within the seal will cause the seal to alter shape to a greater extent to conform against the shape of the nose of the wearer.

As can be seen, the seal does not seal against the bridge of the nose or any flat part of ridge cartilage of the nose between the tip and the bridge.

In at least the embodiment shown the upper wall portion 41 above the aperture 40 includes an upper concave section 41a (see especially FIG. 9) within the greater general concavity of the supple center part of the wearer side of the seal, to receive specifically the tip of the nose, which is concave in both a height and a width of the seal. This upper concave section 41a may have an intermediate wall thickness greater than the balance of the center part of the wearer side of the seal but less than left and right outer stabilising parts of the wearer side of the seal as are described subsequently, or less than an external side of the seal. It may have a wall thickness in the range about 0.4 or 0.5 mm to about 1 or 2 mm for example. Upper concave section 41a may extend from upper edge 40b of the seal outlet aperture to at or towards an upper periphery of the seal. It may have symmetry about the height axis of the seal. Above this slightly thicker wall thickness section 41a the thickness of the upper wall section 41 at 41b preferably reduces, for example with a tapering wall section, for example to return to the same thinner wall thickness as the lower wall and side wall portions 42-44 of the center of the wearer side of the seal.

Figure 11:
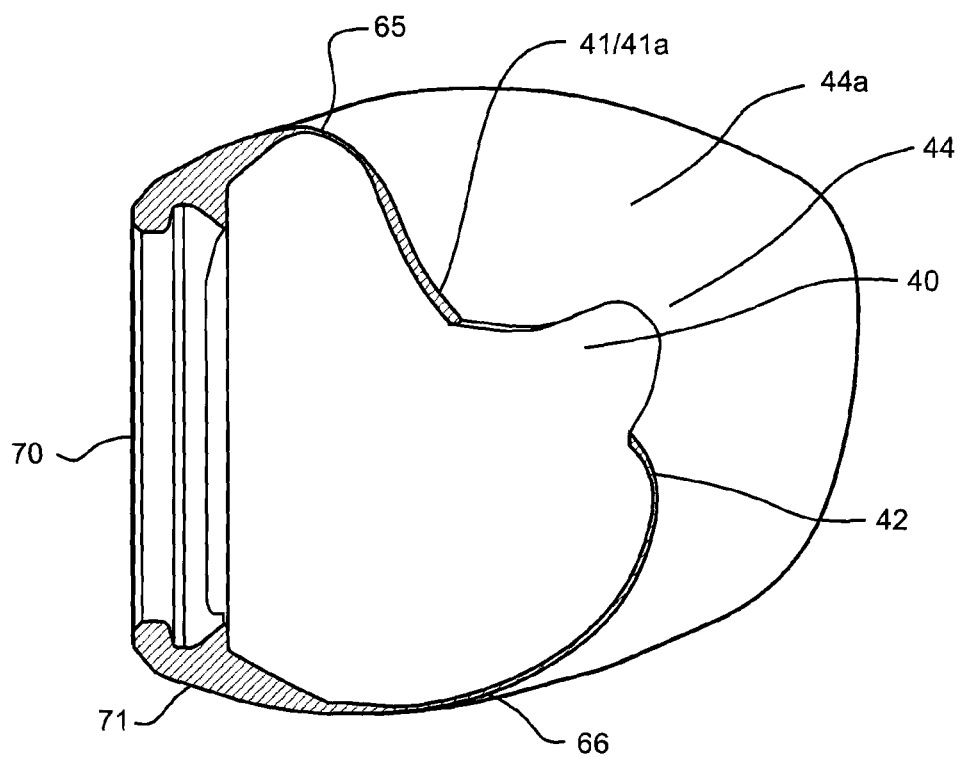
FIG. 11 is a vertical cross-section view of the seal.
Figure 12:
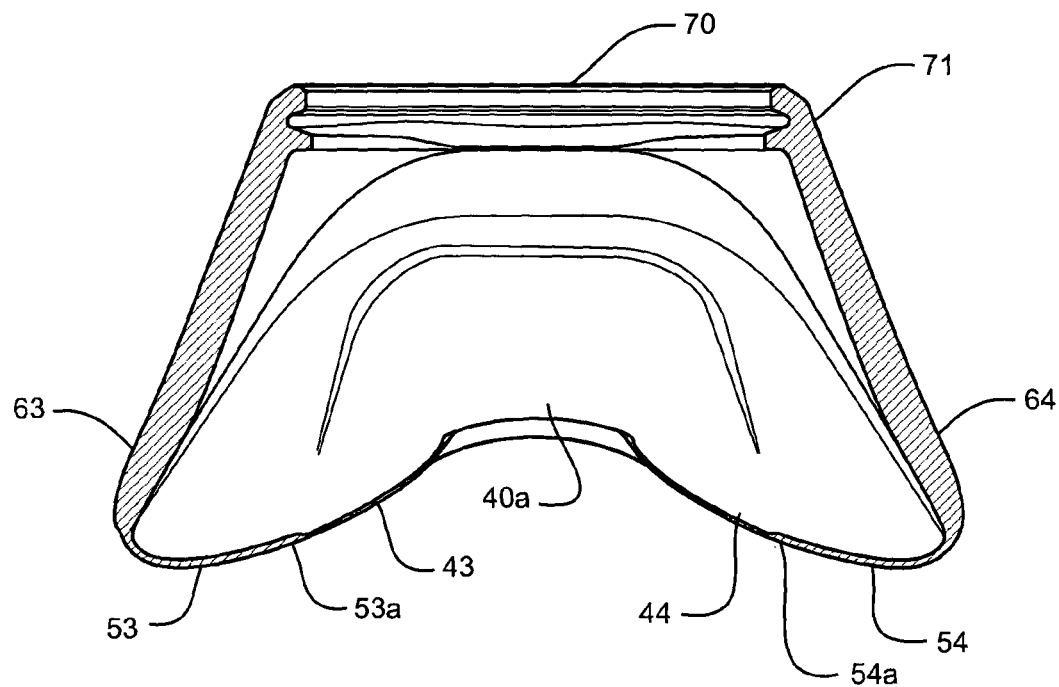
FIG. 12 is a horizontal cross-section view of the seal.

Thus the wearer side wall of the preferred embodiment seal thus described has a pre-formed (before being worn) approximate S-shape in central vertical cross-section-see FIG. 11. That is, the upper wall portion 41 is concave, especially at 41a, to receive the tip of the nose of the wearer, and the lower wall portion 42 is convex, to cushion-contact the upper lip below the nose of the wearer, and these upper and lower portions are joined by the aperture. In the preferred embodiment the S-shape may be considered top truncated in that the upper wall portion 41 is less convex than is the lower wall portion concave). Also the seal has an approximate U-shape when considered in horizontal cross-section-see FIG. 7.

In at least the embodiment shown the left and right side wall portions 43 and 44, or at least upper sections 43a and 44a of the left and right side wall portions 43 and 44, have an outwardly projecting or convex shape or bump (away from an interior of the seal) on opposite sides of the seal. These outwardly projecting or convex upper sections 43a and 44a on opposite sides of the seal are typically above the aperture in the height of the seal as shown. They may contact the corners of the nose or the crease or recess at the junction between the bottom of the sides of the nose and the face, and assist in avoiding upward leakage of air pressure, towards the eyes, in this area. Under gas pressure within the seal they may deform (push) outwardly and/or inflate against the corners of the nose to enhance this seal. The outwardly projecting or convex sections 43a and 44a may locate between the left and right outer stabilising parts 53 and 54 (described in further detail below) and the upper concave section 41a of the supple center part of the wearer side of the seal. The seal may be preformed with the outwardly projecting or convex sections 43a and 44a on the wearer side. The convex sections 43a and 44a are preferably convex in both a height and a width of the seal. This convex section 43a and 44a may have a wall similar to the balance of the center part of the wearer side of the seal but less than left and right outer stabilising parts of the wearer side of the seal as are described subsequently, or less than an external side of the seal. It may have a wall thickness in the range about 0.1 to about 0.5 mm, or about 0.1 to about 0.3 mm, or about 0.2 to about 0.3 mm, for example.

In an alternative embodiment the single aperture 40 may be replaced by two smaller apertures (separated by a bridge between them which may be slightly thickened for example) the rim around the edge of each of which is upturned to seat against the entry to the nares of the wearer ie slightly enter the nares, by for example about 0.1 to about 3 mm.

In at least some embodiments the wearer side of the seal comprises left and right outer stabilising parts 53 and 54 beyond or connecting to the left and right side wall portions 42 and 44 of the supple center part, to contact the wearer's face adjacent the lower flanks of the nose on the left and right sides of the nose (see in particular FIG. 4C). These outer stabilising parts 53 and 54 are flexible or supple but relatively less so (or are relatively stiffer) than the more supple lower-nose-receiving center part of the seal. For example these left and right outer stabilising parts 53 and 54 may have a thicker wall section than a wall section of the lower-nose-receiving center part (see FIG. 12). Their wall thickness may be in the range about 0.5 mm to about 1 or 2 mm for example. An angle between these left and right outer stabilising parts may be between about 30 and about 180 degrees or about 70 and about 150 degrees for example. The left and right outer stabilising parts 53 and 54 assist in stabilising or positioning the seal on the face of the wearer and in particular may assist in stabilising the seal or interface against rotation about a horizontal axis when worn.

The seal may be proportioned so that a junction or change in wall thickness on either side of the seal between an inner edge 53a and 53b (see FIG. 12) of these left and right outer stabilising parts 53 and 54 and the more supple walls 43 and 44 center part of the seal is sits at or adjacent the junction between the lower sides of the nose and the face adjacent the nose when the interface is worn.

The seal comprises an outward side opposite the wearer side which is less flexible or is stiff relative to at least the center part of the wearer side of the seal, and may be less flexible or stiffer than both the center part and the left and right outer stabilising parts of the wearer side of the seal. For example the left and right outer parts of the external side of the seal may have a greater wall thickness than the central part or both the central part and the left and right stabilising parts of the patient contacting side of the seal.

The outward side of the seal comprises less flexible left and right stabilising parts 63 and 64 adapted to contact the face adjacent the lower flanks of the nose on the left and right sides of the nose when worn. The hollow interior of the seal may extend to between these left and right side parts 63 and 64 of the outward side of the seal and the left and right parts 53 and 54 of the wearer side of the seal. An angle between the left and right parts 63 and 64 of the outward side of the seal may be between greater than about 20 to about 90 degrees or about 30 to about 60 degrees for example. These left and right parts may be formed of the same material as the wearer side of the seal such as a silicone material may have a wall thickness of about 3 mm to about 5 mm for example. These integral left and right stabilising parts 63 and 64 provide the seal with enhanced stability against rotation on the face due for example to tube drag forces.

In some embodiments the outward side of the seal connects to upper, lower, and outer tip peripheral parts 65-68 of the wearer side of the seal with a wall thickness which reduces, for example with a tapering wall section, from that of the outward side of the seal to the wearer side of the seal. In particular, in the embodiment shown bridging portion 65a (see FIGS. 5 & 7) between the outward side of the seal and the top of the upper wall section 41 has a thin wall section so that it is also flexible or accommodating in a depth of the seal to assist in accommodating different nose depths (face to tip). It may have a wall thickness similar to that of supple lower wall and side wall portions 42-44 of the center of the wearer side of the seal for example.

In at least some embodiments left and right peripheral parts 67 and 68 of the seal at left and right outer tips of the seal which contact the face when worn include an approximately straight part bridging upper and lower peripheral parts 65 and 66 of the seal.

In the embodiment shown the outward side of the seal includes an opening 70 to pass gas flow to and from the hollow interior of the seal. Typically, the rim and seal wall 71 around the opening 70 is substantially thicker and relatively stiffer than the supple sealing portions of the seal.

Frame

FIGS. 13 to 16 show an interface of an embodiment of the invention. The interface comprises the seal of FIGS. 5 to 12. The frame (and the elbow) may be formed to be stiffer than the seal.

In the embodiment shown the seal 30 attaches to the frame 31 by the resiliently flexible and stretchable rim 71 around aperture 70 in the outward side of the seal engaging over a complementary formation such as a rim on the wearer side of the frame 31, around a passage through the frame from the interior of elbow 34. Thus the seal 30 and the frame 31 together form an enclosure having a gas flow inlet from the CPAP system and aperture 40 through the seal to the wearer.

In the embodiment shown the seal 30 attaches to a subsidiary frame part or boss 31b having a rim 81 which engages, for example in a snap fit, into a matching aperture 82 in a center part 31c of primary frame part 31 as shown. On the seal side the boss 31b has a peripheral flange 83 of slightly larger diameter. Also the depth of the rim 81 of the boss is greater than that of its receiving aperture 82 in center frame part 31c such that when the boss 31b is home in the frame part 31a an annular space is defined between the inside or wearer side of the center part 31c of primary frame part 31a and the boss flange 83 around the boss, into which the rim 71 of the seal is fitted to attach the seal to the frame, by stretching the seal rim 71 over the flange (see FIGS. 3, 15, and 16). The inside surface of the rim 71 of the seal may include features such as lips and/or channels to engage with features such as channels and/or lips on the frame to detachably secure the seal to the frame. Alternatively the seal may attach to the frame by clip parts, or over-moulding to a rim which in turn attaches to the frame, for example. In the embodiment shown the plane of the rim 71 of the seal is approximately vertical when the mask is worn by a user standing upright, but in another embodiment the seal may be formed so that the plane of the seal rim is at an acute angle to the horizontal, such as an angle in the range 45 to 90 degrees for example, while the body of the seal is still oriented relative to the frame including side arms, and the users face when worn, as shown in FIGS. 13 to 17.

Figure 13:
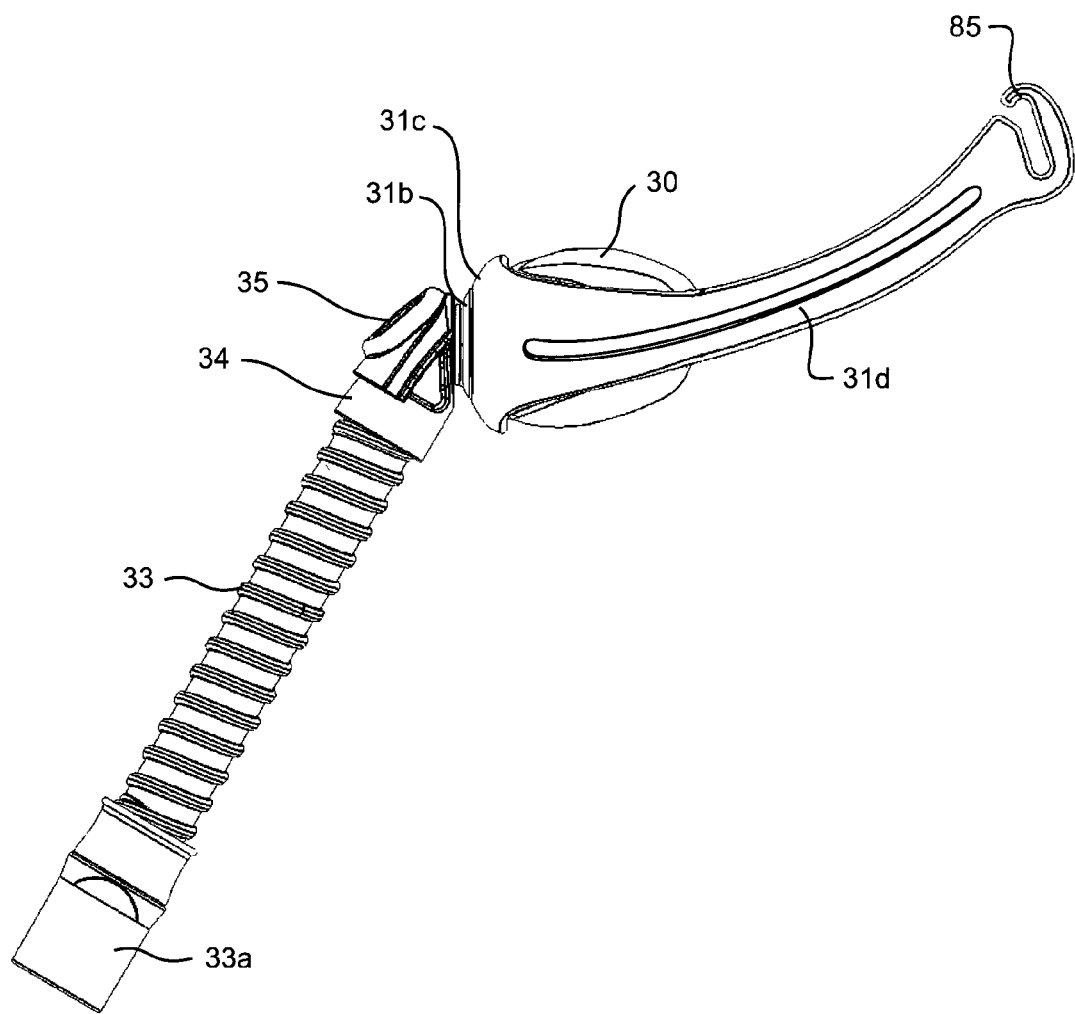
FIG. 13 is a side view of the interface.
Figure 14:
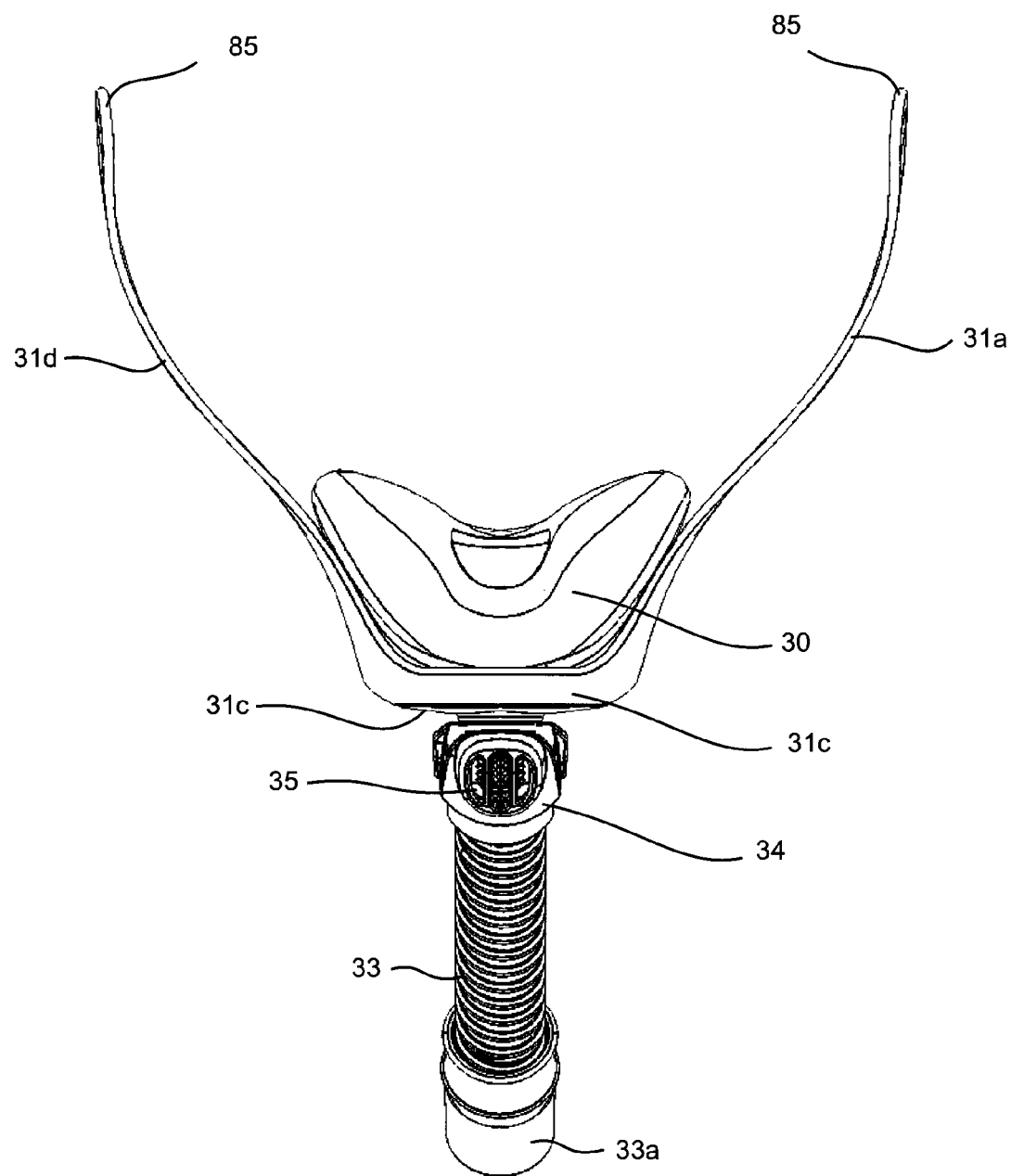
FIG. 14 is a top view of the interface.
Figure 15:
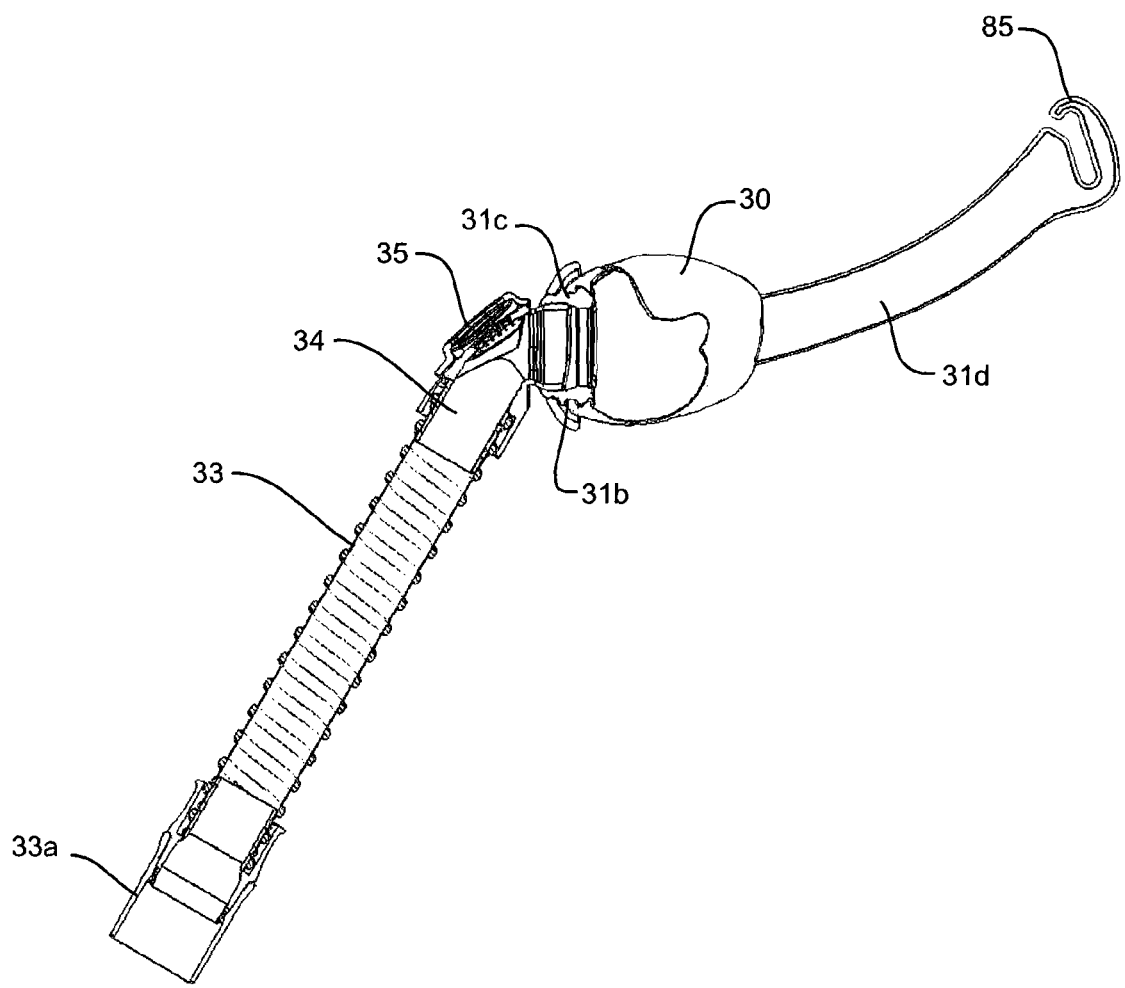
FIG. 15 is a vertical cross-section view through the interface.
Figure 16:
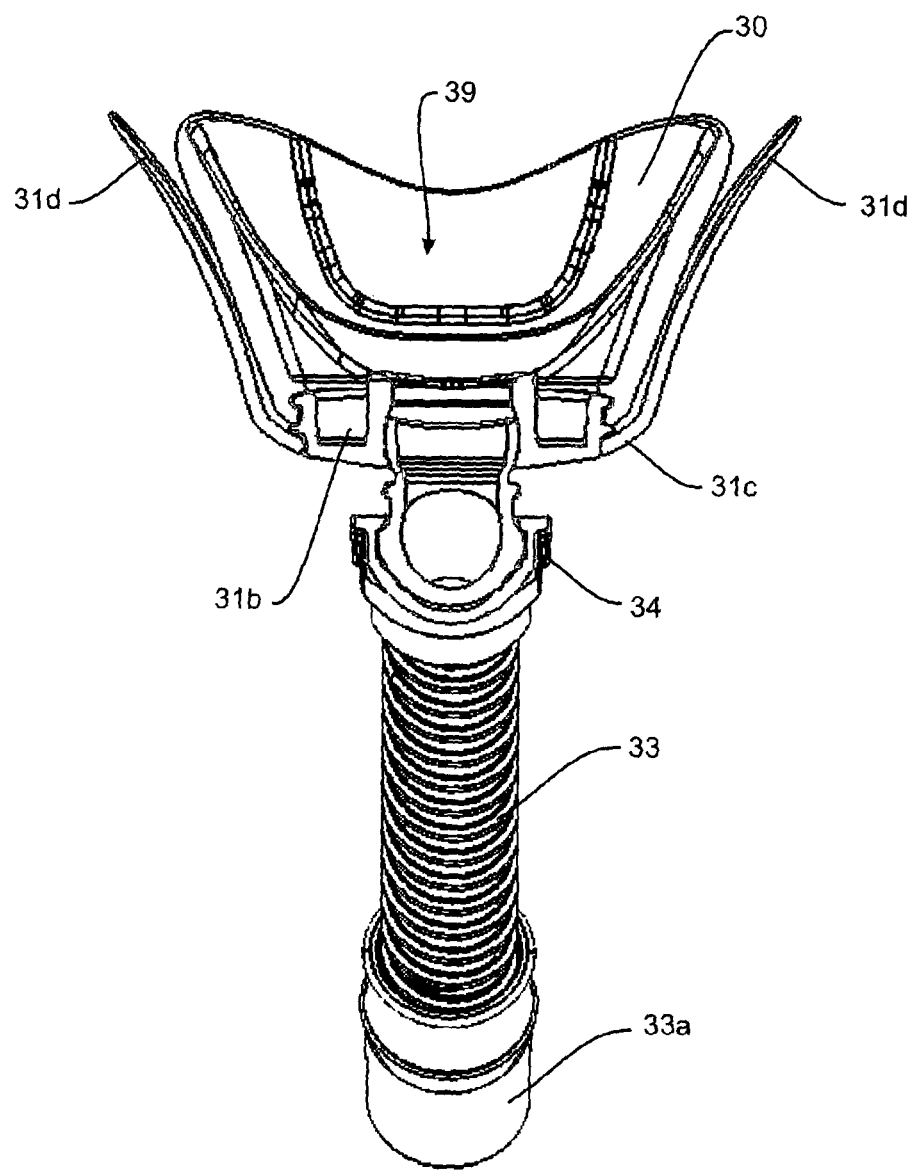
FIG. 16 is a horizontal cross-section view through the interface.

The frame 31 may comprise side arms 31d which extend outwardly (away from each other) and rearwardly and upwardly at a shallow angle, past left and right extremities of the seal and along the left and right cheeks and in particular cheekbones of a wearer, as shown in FIG. 2, to connect to headgear for holding the seal on the face of a wearer. Such side arms 31d may be longer than they are deep or thick and may be resiliently flexibly connected to the frame and/or resiliently flexible along their length (widthwise but not heightwise), and may extend to a location between the ears and eyes of the wearer and/or to approximately the temple of the wearer, where the side arms connect to headgear. In a preferred embodiment the length of the side arms is between about 100 mm and about 150 mm. The shape of the side arms 31d and/or angle between them is such that the side arms rest on the left and right cheeks and in particular cheekbones of a wearer to assist in stabilising the interface against rotation about a horizontal axis when worn. The side arms 31d may be integrally formed with the frame by injection moulding from a plastics material for example. The side arms may be resiliently flexible towards and away from the face of a wearer in an approximately horizontal plane (when worn), to accommodate different face sizes, but are relatively inflexible in an approximately vertical plane. As shown in FIG. 13 (only) the side arms may comprise an aperture or cut-out extending lengthwise of the side arms, preferably lengthwise of a major part of the length of the side arms, to increase this resilient flexibility of the side arms towards and away from the face of a wearer, but to retain relative inflexibility in an approximately vertical plane (when worn).

Preferably the side arms 31d comprise a softer material at least on wearer facing surfaces of the side arms, or fully around the side arms, for softening contact of the side arms with the face of a wearer, which may be removable for cleaning.

At their outer ends the side arms 31d comprise connector parts for detachably connecting the side arms to headgear. In a preferred form the end of each side arm comprises a hook 85 and in particular an upwardly open hook part, for entering into a loop 95 of the headgear.

In preferred embodiments the interface does not comprise a T-piece from the frame upwardly (when worn) to connect to headgear at the wearer's forehead.

Instead of the side arms as shown (or with shorter side arms) the ends of headgear straps may attach to the mask frame (or shorter side arms) on either (left and right) sides via stiffer strap ends, which terminate at the mask by an attachment mechanism which allows movement in an approximately horizontal plane but not in an approximately vertical plane, such as a hook which engages into a vertical upright slot on the mask frame.

As stated the frame may comprise elbow 34 connected to the opening through the frame. The elbow may be a swivelling elbow. In preferred forms the connection of the elbow to the frame provides for both rotation and pivoting of the elbow relative to the frame. For example the connection may comprise a ball joint connection to the frame so that the elbow can pivot about axes parallel to and perpendicular to its connection with the mask. The elbow may include a part ball end 34a (see FIG. 3) which snap fits in a socket opening 31e in frame part 31b.

Elbow 34 is connected to the end of a length of flexible tubing 33. The other end of flexible tubing 33 is terminates with a connector 33a. The elbow 34 preferably defines an angle between flow in the conduit 33, and flow through the connection to the mask of between 0° and about 90°, or about 30° and about 60°.

As stated the elbow may include a gas washout vent 35 which may comprise a plurality of holes through the elbow from interior to exterior. The vent apertures are preferably located on the outside of the bend of the elbow, substantially in the line of the flow path of gases leaving the mask. Alternatively gas washout vent(s) may be provided on the frame for example.

Headgear

Figure 17:
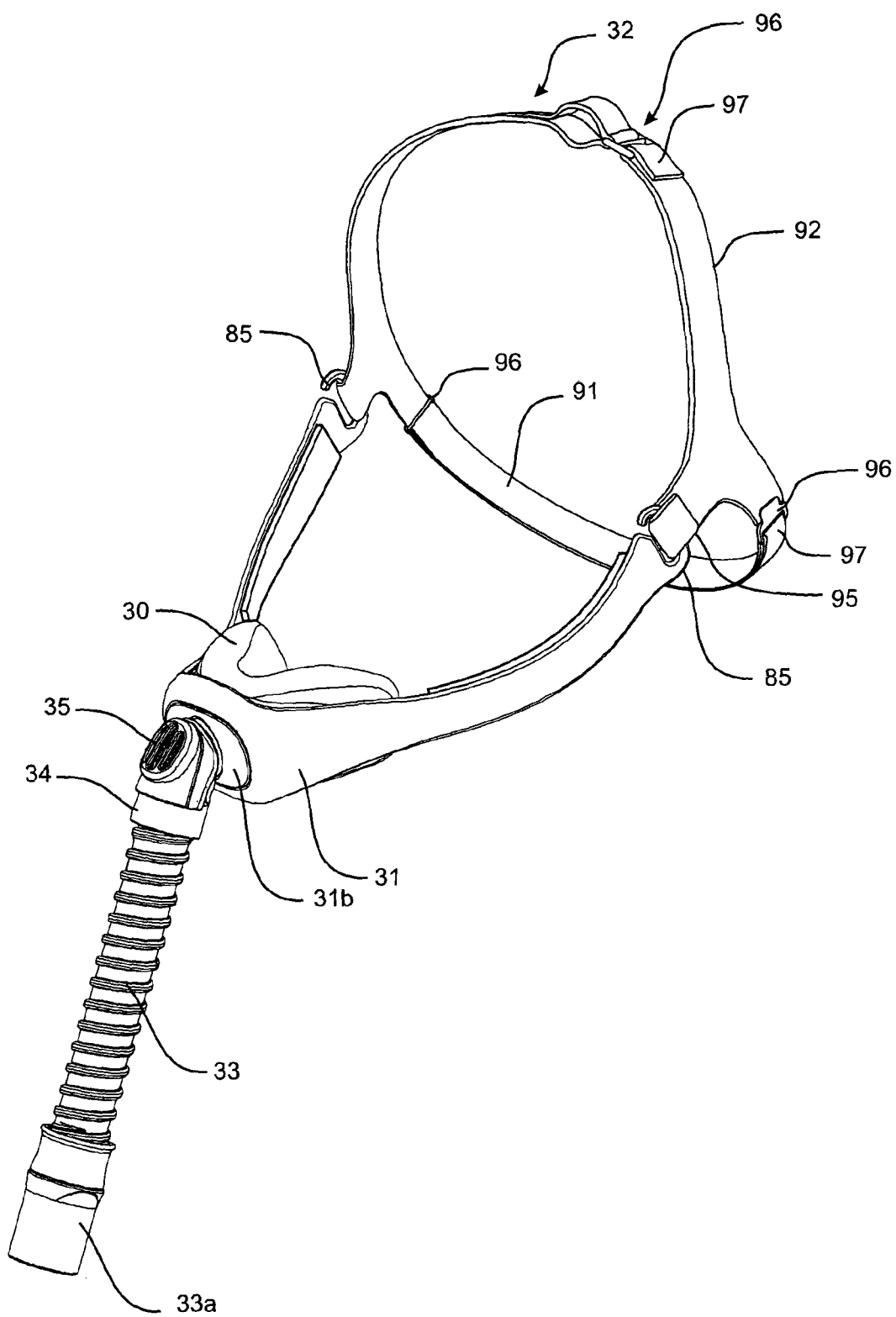
FIG. 17 shows the interface with an embodiment of headgear.

FIG. 17 shows the interface with an embodiment of headgear suitable for use with an interface mask of the invention. The headgear comprises a rear strap 91 to extend around a rear part of the head of a wearer and a top strap 92 to extend over the top of a head of a wearer. The rear strap 91 may extend around a lower rear part of the head of the wearer and in particular over a lower part of the occipital bone. The top strap 92 may be a crown strap or a forehead strap.

The headgear may be formed at least in part from a soft flexible material such as a cloth covered foam material such a BREATH-O-PRENE material for example. The headgear may be formed by cutting out the headgear to shape from the sheet material by blade cutting or radio frequency cutting for example. In one embodiment the edges of the headgear are thermoformed ie compressing under heat, to form rounded edges. That is, heat and pressure are applied along the headgear edges to compress the opposite outer surfaces of the headgear material towards one another at the edges and heat bond them together. This may be done simultaneously with cutting the headgear to shape for example, by cutting an outline of the headgear shape in the sheet material and thermoforming to define the rounded headgear edges in one operation, or instead by first cutting the headgear to shape and then rounding the edges in a second operation. The rounded edges or any joints in the headgear may alternatively be formed by ultrasonic or radio frequency welding, for example.

Figure 18A:
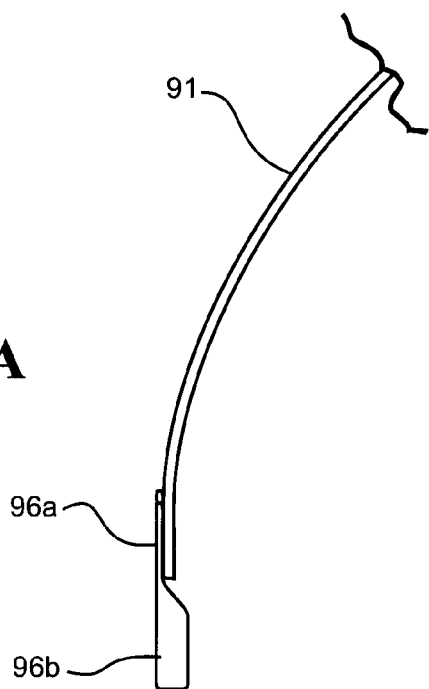
FIG. 18A is an enlarged edge-on view of a loop or buckle end of a strap and FIG. 18B is an enlarged side view of the loop or buckle strap end, of the headgear of FIG. 17.
Figure 18B:
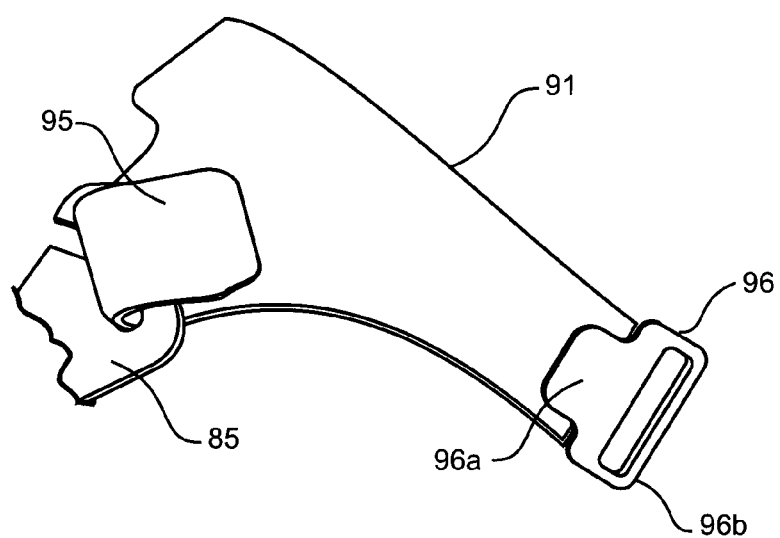
Figure 19:
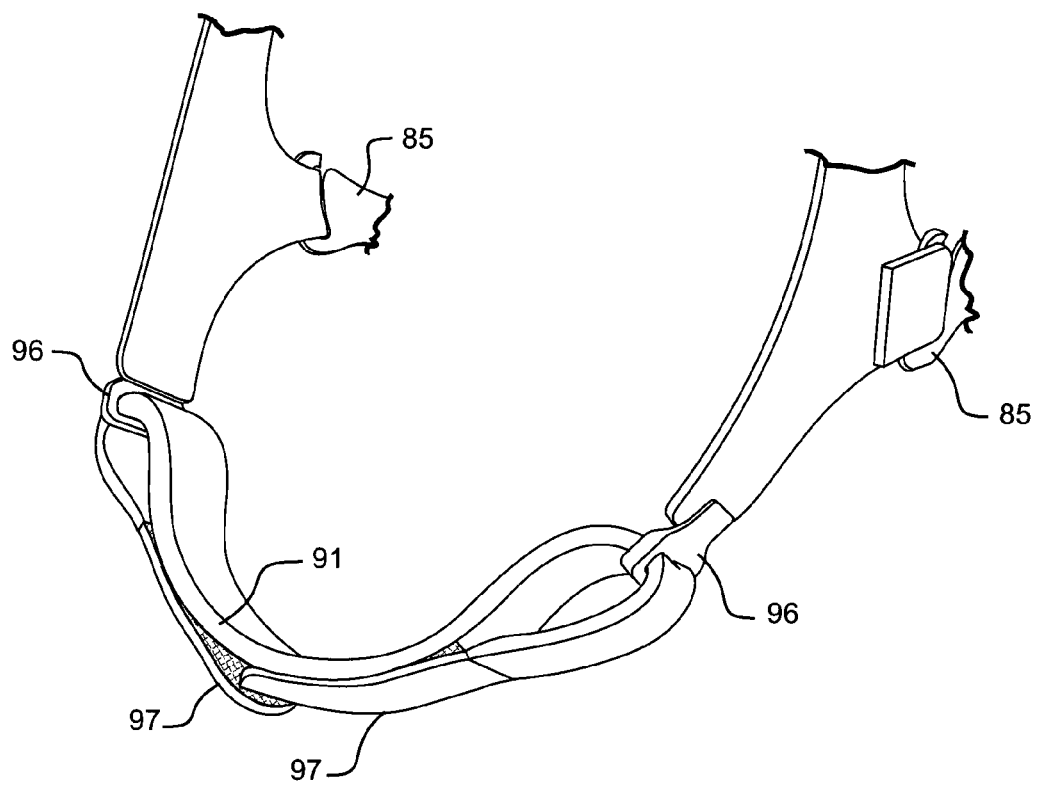
FIG. 19 is a view of the rear of the headgear of FIG. 17 showing two buckles of FIGS. 18A & B each with a tongue strap end passing through the buckle.

In at least some embodiments the length of the rear strap 91 and/or the top strap 92 is adjustable. For example the top strap may be formed in two parts one of which terminates in a loop 96 and the other of which terminates in a tongue 97 which can pass through the loop and be secured back upon the strap part to fix the length of the top strap, by a hook or loop fastener panel on or tab from the end of the tongue and a loop or hook panel on the strap or to a cloth covering of the tab (loop and tongue adjustment). The rear strap may have a buckle 96 and tongue 97 on left and right sides as shown for length adjustment as shown in FIG. 19, or alternatively on one side or centrally. In preferred forms the buckles 96 are formed separately from a different and relatively more rigid material, such as a plastics material for example by injection moulding for example, and are attached to the end of a soft strap by welding such as ultrasonic welding for example, or other suitable means. FIG. 18A is an enlarged edge-on view and FIG. 18B is an enlarged side view of a buckle 96 end of a headgear part or strap. Each buckle (or fastener part) comprises a first portion 96a attached to the soft flexible material of the headgear and a free second portion 96b which comprises an open loop for receiving therethrough the tongue end of a strap.

In a preferred form the headgear comprises a loop 95 on each of the left side and a right side of the headgear as referred to previously, at a location positioned between the eyes and ears when the headgear is worn, for receiving a hook end 85 of side arms of the interface as described above. The hook end of the side arms attaches directly to the headband comprised of the rear and top straps, without a side strap from the headband towards the mask. In this or other embodiments the side arms may alternatively attach to the headgear by releasable clips or hooks or hook and loop attachment, for example.

Figure 20:
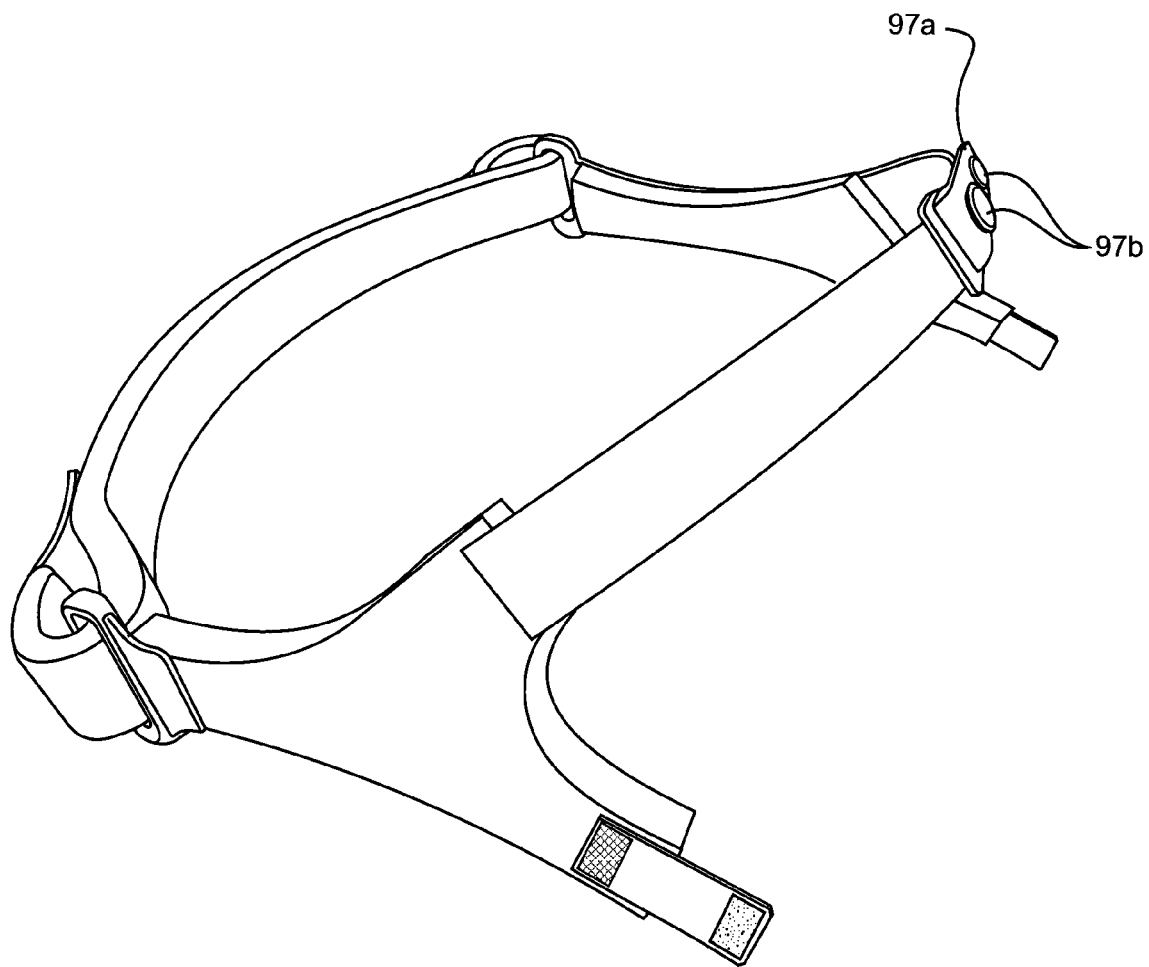
FIG. 20 is a view similar to FIG. 17 including a headgear embodiment similar to that of FIGS. 17 to 19 but with in this embodiment an alternate top strap construction.

FIG. 20 is a view similar to FIG. 17 including a headgear embodiment similar to that of FIGS. 17 to 19 but with in this embodiment an alternate top strap construction. In this embodiment the top strap is not formed of the same material as the balance of the headgear such as soft flexible material such as a cloth covered foam material, but is formed of a non-foam plastics material such as plastic strap which may be relatively inextensible lengthwise (but is flexible otherwise, for accommodating the headshape). Again the top strap may be formed in two parts, one of which terminates in a tongue with apertures 97a and the other of which terminates in a buckle with buttons 96a into which the tongue 97a can adjustably pass and over which buttons the tongue apertures may be fitted, with a snap fit, to fix the adjustment and thus the length of the top strap. Optionally a soft material may be provided on the user side of the top strap or part thereof for user comfort.

In embodiments in which frame side arms attach directly to the headgear, such as to a headband as shown comprised of the rear and top straps, without a side strap from the headband towards the frame, as shown, and the edges of the headgear are thermoformed ie compressing under heat to form rounded edges as described above which tends to reduce the 'floppiness' of the soft headgear and cause it to tend to maintain its headband shape, the headgear can be donned ('like a cap') by holding the frame at the seal or near the seal (as one would hold a cap at its peak when lifting or flipping it onto the head). The headgear may be removed or doffed in a reverse similar action. Other aspects of the headgear and frame which help to reduce the 'floppiness' of the soft headgear and cause it to tend to maintain its headband shape include, the relatively high density of the foam used to form the headgear, the relatively long side arms of the frame that extend substantially towards or adjacent the wearer's cheeks when worn, and/or the stiffness of the connections (the tight tolerances or tight connections of the headgear about the connectors) between the side arms and the headband (tight loops 59 about the hooks 85) and/or the connections of the top and rear straps of the headgear (tight loops about buckles 96). Such aspects of the headgear enable the headgear to be donned ('like a cap') by holding the frame at the seal or near the seal (as one would hold a cap at its peak when lifting or flipping it onto the head). The headgear may be removed or doffed in a reverse similar action.

Seals and masks of the invention may be used with headgear in other forms such as headgear with two straps which attach to the mask on either side ie headgear which comprises left and right side upper and lower straps. The frame of such an interface embodiment may or may not comprise side arms as described above. Left and right upper straps may pass downwardly (when the headgear is worn) between the eyes and ears of the wearer and left and right lower straps may extend from the lower rear of the head and beneath the ears to the mask (and attach to the mask each side below the upper straps). Alternatively upper and lower straps may join for example in a stiffer yoke before attaching to the mask frame, or which is integral with the mask frame. Such a headgear may have buckle and tongue, loop and tongue (as described above) or other adjustment in the upper or lower straps or both sides, part way along their length(s) or at the connection of the straps to the mask. In less preferred embodiments the upper straps may attach to the top of a T-piece extending upwardly from the frame to the wearer's forehead. In another embodiment again the headgear may comprise a single strap which passes or loops from the mask on one side around the rear of the head and back to the mask on the other side. Such a headgear strap may be elastic or resiliently stretchable and/or may have a length adjustment device (eg buckle and tongue, loop and tongue, etc) in the rear or at the sides or at the connection of the headgear to the mask on one or both sides. Variant of such headgear may also comprise a crown strap.

Side Hinges in Seal

FIGS. 21 and 22 and 23 and 24 show two embodiments of masks of the invention in which the left and right outer parts of the outward side of the seal each comprise a higher flexibility portion intermediate of their length. These higher flexibility portions enable transverse movement of the balance of the seal relative to the part of the seal including the rim 71 which connects to a frame of an interface. Thus they may enable some movement of the frame of the mask, due to side force on the mask when a wearer is sleeping on their side with their one side of their face against a pillow for example, which may tend to push the frame sideways, with less tendency to also move the seal itself sideways, particularly the face contacting or wearer side of the seal, which may break the seal to face contact and lead to air leakage.

Figure 21:
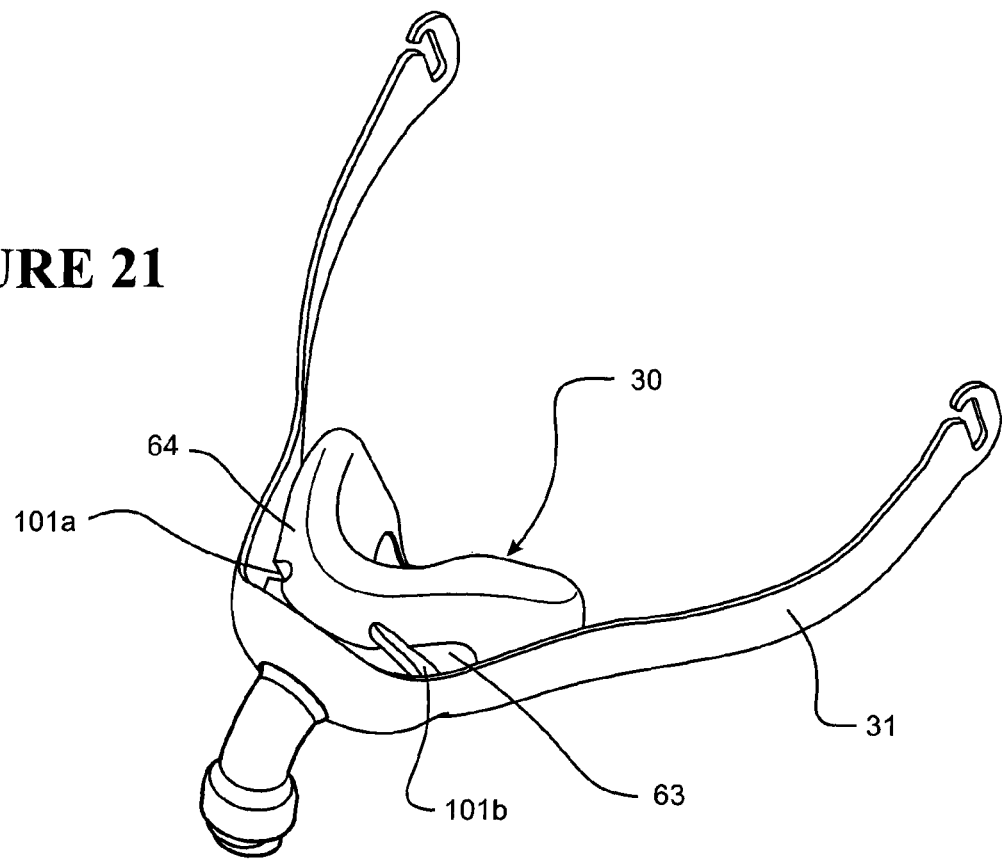
FIG. 21 is a perspective view of an interface (excluding headgear) of an embodiment of the invention in which the seal comprises side hinges.
Figure 22:
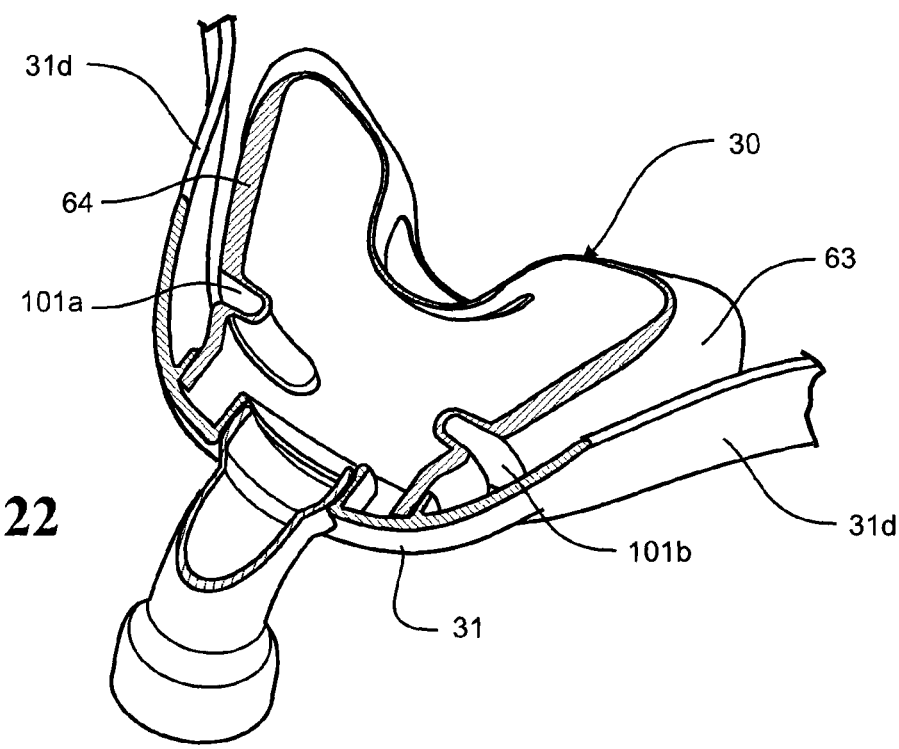
FIG. 22 is horizontal cross-section view of the interface of FIG. 21.
Figure 23:
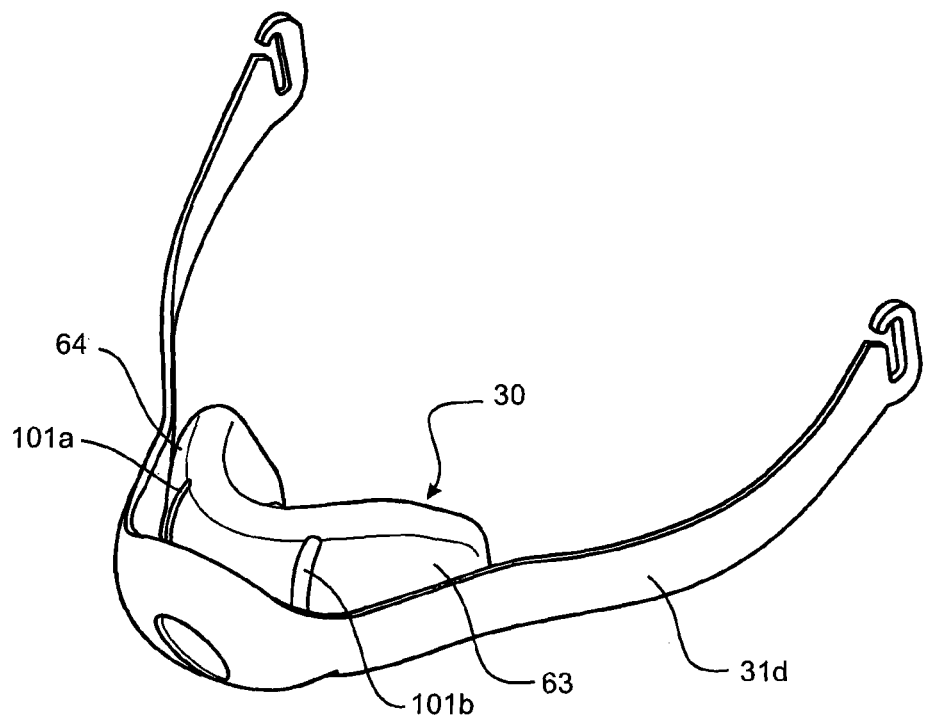
FIG. 23 is a perspective view of an interface (excluding headgear) of another embodiment of the invention in which the seal comprises side hinges.
Figure 24:
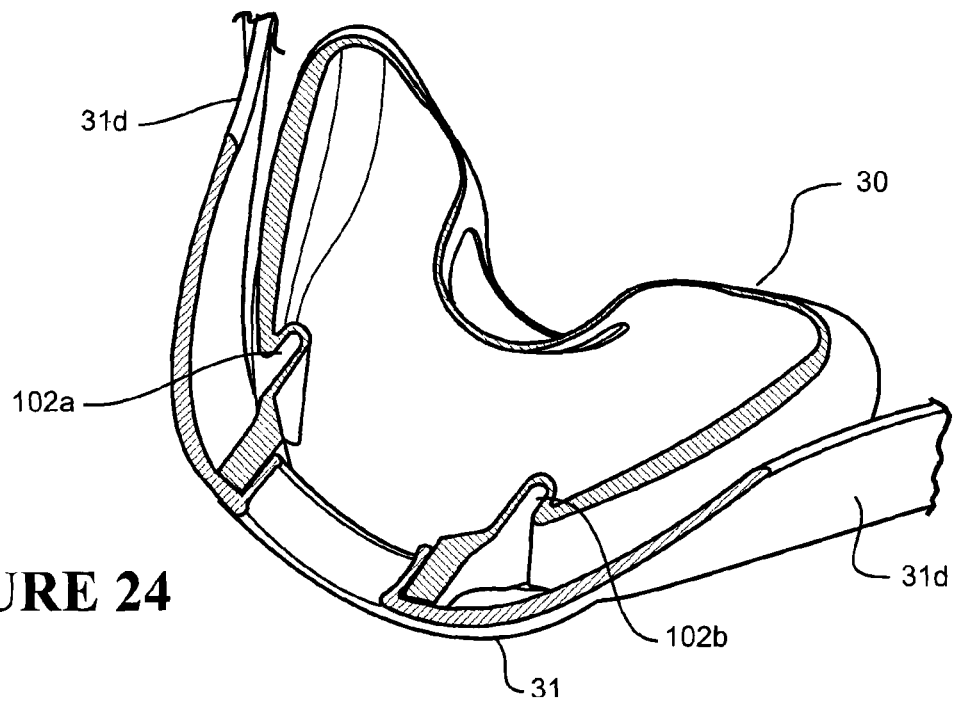
FIG. 24 is horizontal cross-section view of the interface of FIG. 23, FIGS. 25 to 29A and B illustrate headgear embodiments that cover the ears of the user and can include at least two sections having different material characteristics.
Figure 25:
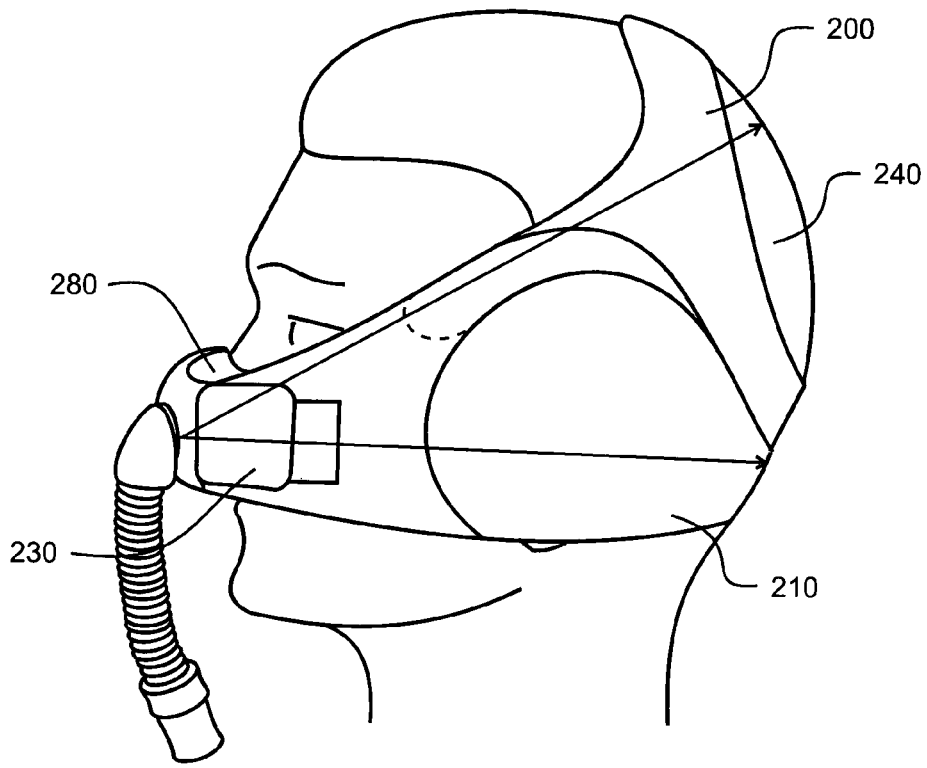
Figure 26:
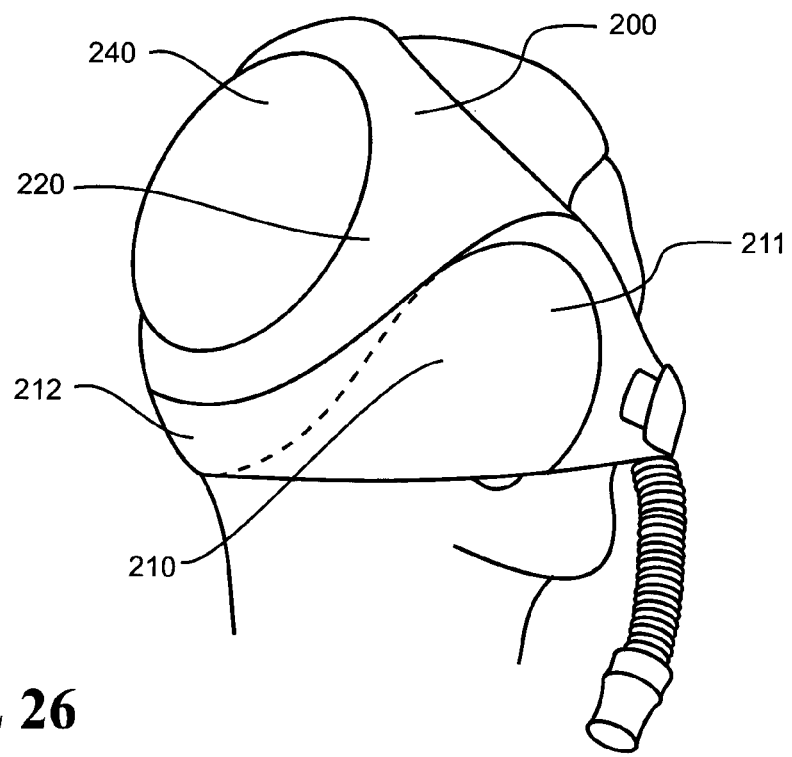
Figure 27:
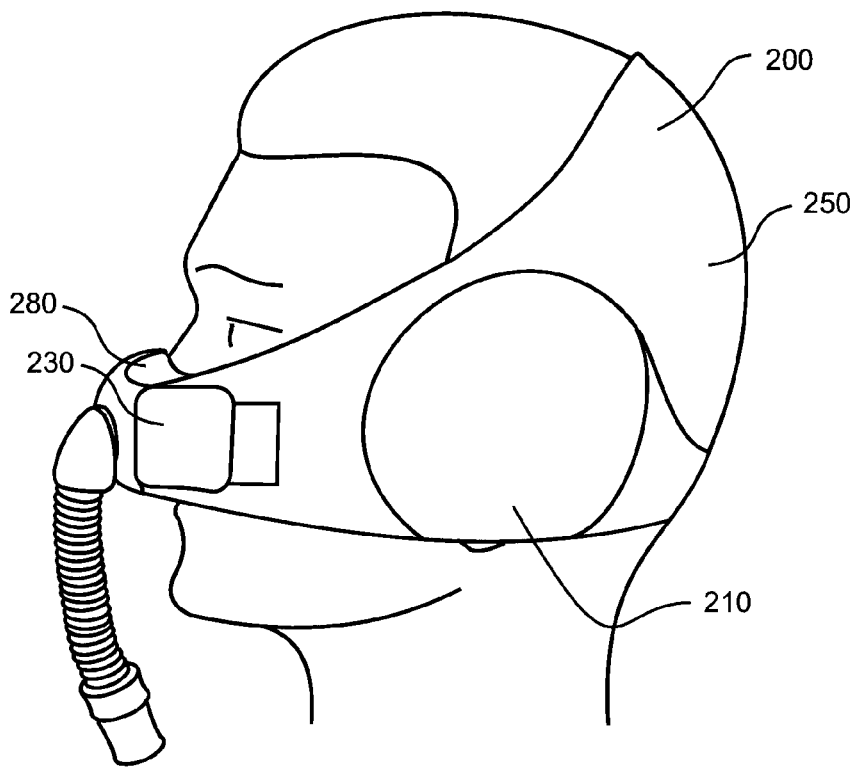
Figure 28:
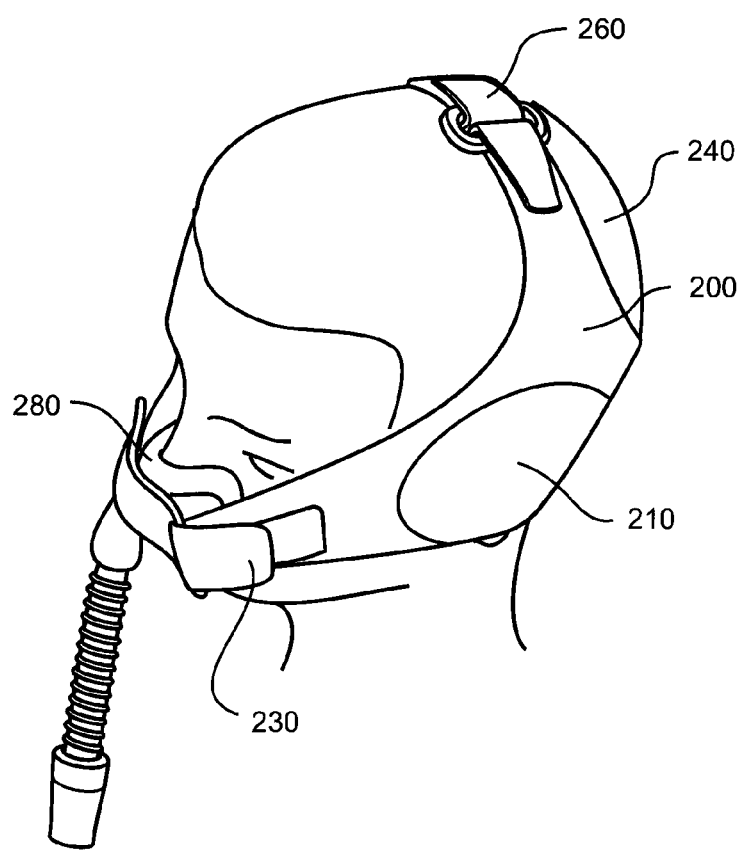
Figure 29:
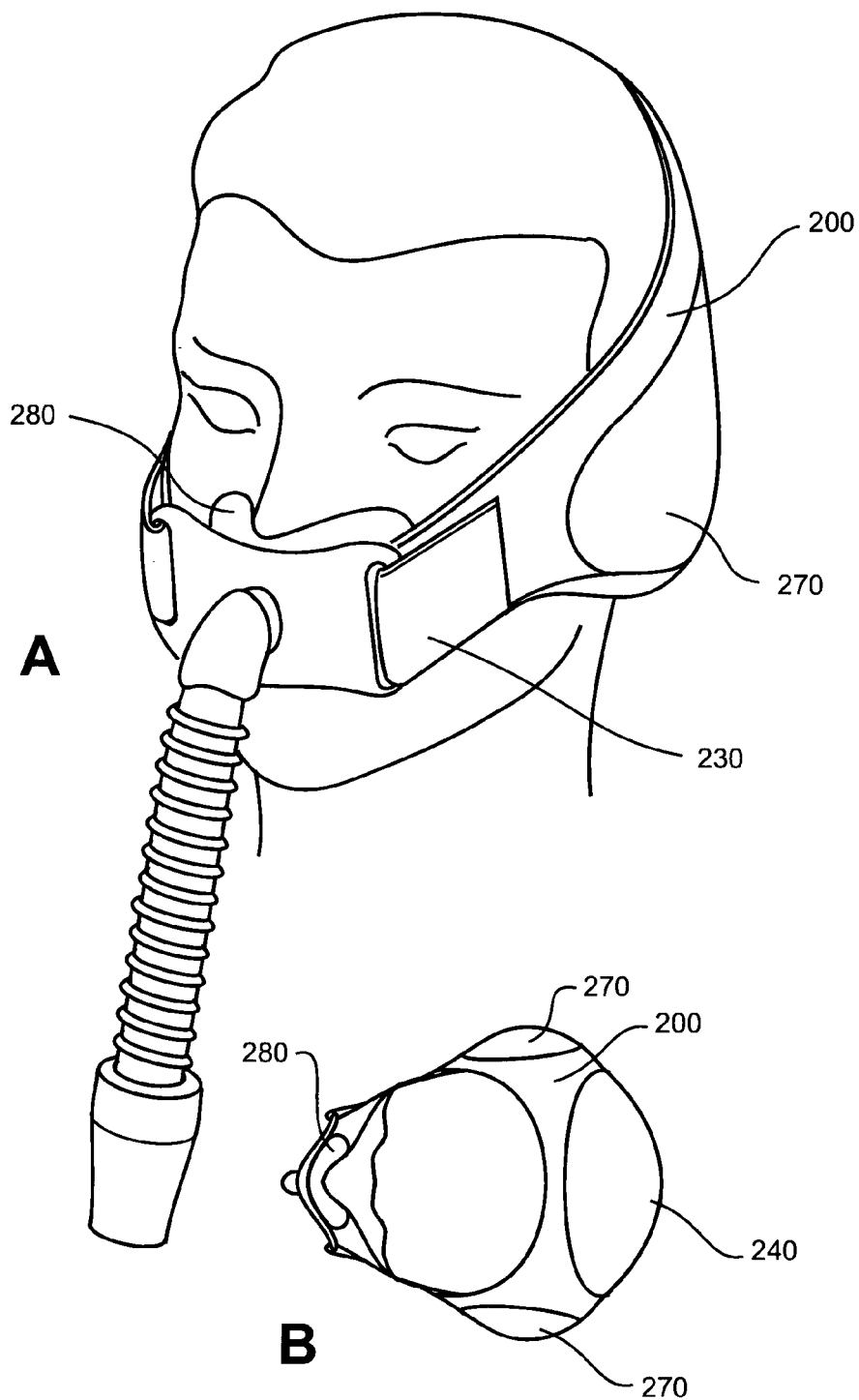
Figure 30:
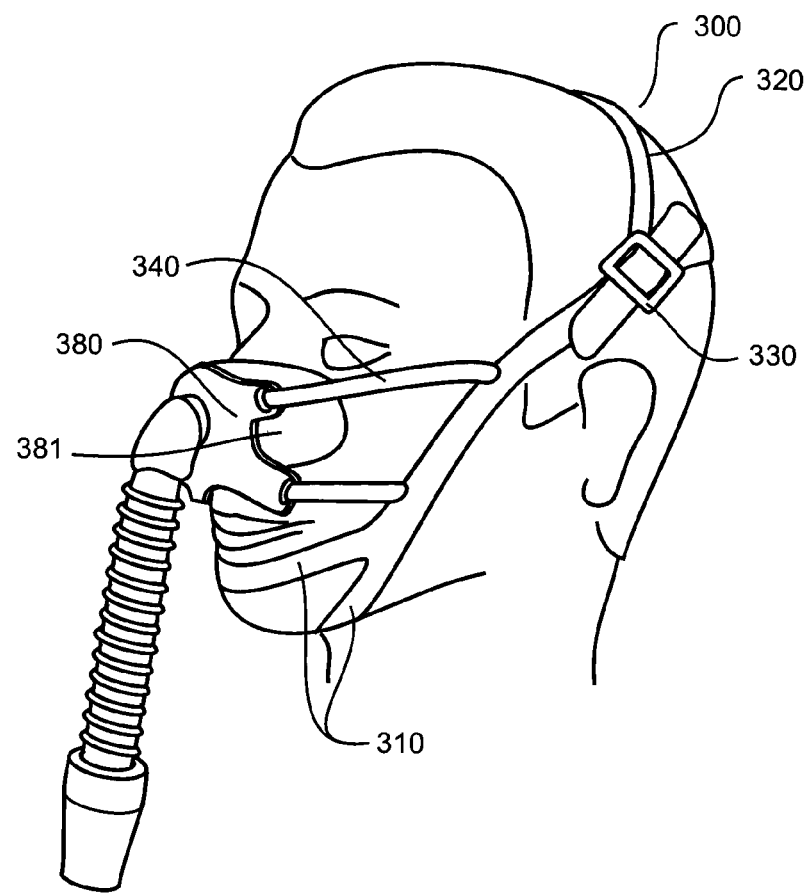
FIGS. 30 to 35 illustrate stretch headgear embodiments that use the chin and parietal region of the head as anchoring points.
Figure 31:
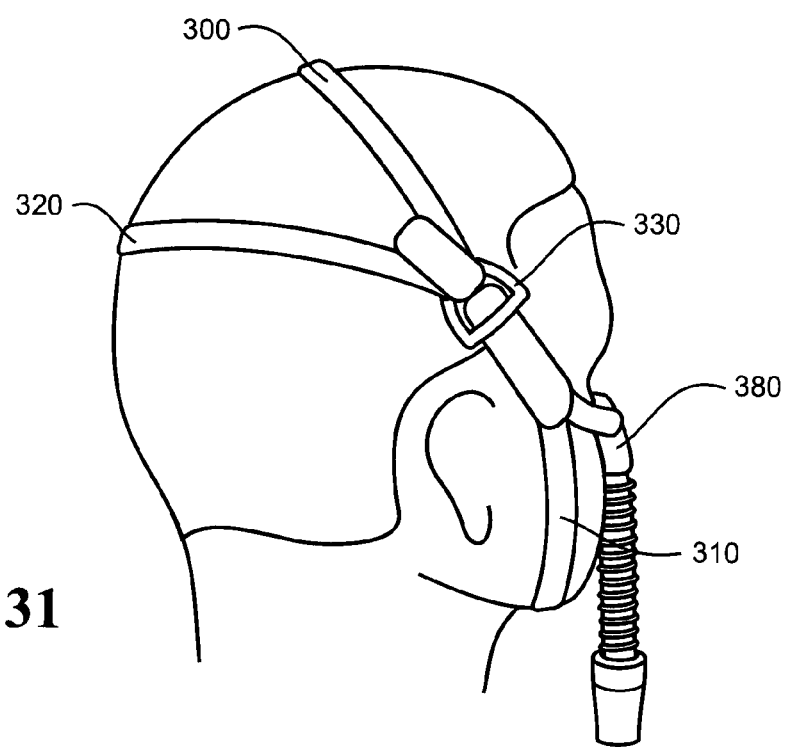

In the embodiments shown the higher flexibility portions comprise folds 101/102 in a side wall of the outward side of the seal, inward directed into the interior of the seal. The folds have a thinner wall section than the outward side of the seal on either side of the folds. In the embodiment of FIGS. 21 and 22 inward directed folds 101a and 101b extend partially across a width of a hollow interior of the seal. In the embodiment of FIGS. 23 and 24 inward directed folds 102 a and 102b extend partially in a depth of a hollow interior of the seal. The embodiments of FIGS. 21 to 24 are otherwise the same as the embodiment of FIGS. 2 to 17.

SUMMARY

The seal of the invention comprises less flexible left and right stabilising outer parts adapted to contact the face adjacent the lower flanks of the nose on the left and right sides of the nose when worn. The seal has enhanced stability against rotation on the face, and in particular about a width axis of the seal, due for example to tube drag forces, which can break the seal and cause leakage, as do preferred embodiments of interfaces comprising the seal and with side arms as described, even though the seal does not seal against the sensitive bridge of the nose or extend, at least to any significant extent such as more than about 1 cm for example, over any flat part of ridge cartilage of the nose between the tip and the bridge. The left and right side wall portions, or at least upper sections of the left and right side wall portions of the supple center of the wearer side, have an outwardly projecting or convex shape (away from an interior of the seal) on opposite sides of the seal. These outwardly projecting or convex upper sections on opposite sides of the seal contact the crease or recess at the junction between the bottom of the sides of the nose and the face, and assist in avoiding upward leakage of air pressure, towards the eyes, in this area. Under gas pressure within the seal they deform (push) outwardly against the face in this area to enhance this seal. The pre-formed or structured but still supple conformable shape of the seal of the invention provides a seal which for many wearers will naturally fit or conform with only a relatively small amount of shape alteration or deformation, and internal gas flow positive pressure may enhance the seal. An effective seal with minimum or no leakage in a small size or low profile mask may be achieved for many wearers, without also requiring that the mask comprise pillows or similar of a conventional direct nasal interface which protrude into the nares of the wearer. An effective seal may be achieved at relatively low gas flow rates through the mask creating a relatively low internal gas pressure within the seal against the nose. Also, because the seal in at least preferred embodiments maintains its shape or structure even when not worn or under internal gas pressure, it may be more intuitive to a user how to place or position the mask on the face.

Other Headgears

FIGS. 25 to 29 illustrate headgear arrangements that provide an advantageous force vector for a patient interface or respiratory mask, such as an obstructive sleep apnea (OSA) mask, by sitting on the back of the head and partially or completely covering the ears. See, for example, FIG. 25.

The headgear 200 can comprise a lightweight stretch fabric, such as Lycra or a similar material, with a more substantial fabric providing support. See, for example, FIG. 28.

In some configurations, the section 210 which covers the ears can be made of very fine, lightweight, stretch fabric to maximise comfort for the wearer. In some such configurations, the more substantial fabric 220 (which can be heavier weight and/or less stretchable) is used to construct a portion or all of the remainder of the headgear. See, for example, FIG. 26.

Layering of fabrics 211 and 212 having different properties or characteristics (e.g., different levels of stretch) in some regions can provide more structure for stability and ease of fitting. See, for example, FIG. 26.

In one or more embodiments, there are wider attachment points 230 (e.g., wider than comparable conventional masks/headgear) at the front to keep the mask seal stable and inhibit or prevent rocking on the face. The attachment points 230 can be as wide as a significant or substantial portion of the height of the mask seal 280. See, for example, FIG. 25.

There can be a generally circular or halo cut out 240 in some embodiments to encircle the parietal region for stability and reduced bulk. See, for example, FIG. 26.

In some configurations, the more substantial fabric can extend beyond the front of the ear to provide more structure to the headgear and prevent it from bunching over the ear. See, for example, FIG. 26.

In some configurations, the headgear 200 (or a main body of the headgear) can be comprised only of lightweight stretch fabric that widens at a region 250 towards the back of the head. See, for example, FIG. 27.

In some configurations, the headgear 200 can be comprised of lightweight stretch fabric that widens towards the back of the head and includes sections of more substantial material around the back 250 to provide structure. See, for example, FIG. 27.

In some configurations, the headgear could be adjustable at the top 260 of the halo. See, for example, FIG. 28.

In some configurations, the headgear 200 could have a thermoformed section that holds the ear covering 270 out from the ear a desirable distance, which can be a relatively small distance in some embodiments. See, for example, FIG. 29.

In some such configurations, the headgear 200 could have a curved plastic piece 270 that sits out from the ear a desirable distance allowing the headgear to be slipped on over the ears more easily. See, for example, FIG. 29.

FIGS. 30 to 36 illustrate stretch headgear arrangements 300 that use the chin and parietal region of the head as anchoring points.

In some configurations, the main structure 300 is comprised of elastic straps, preferably circular knitted, which widen around the chin 310 and back of the head 320. The wider sections can be comprised of stretch fabrics such as Lycra or a similar fabric. See, for example, FIGS. 30 and 31.

In some configurations, there can be adjustment points 330 which sit above the ears. See, for example, FIGS. 30 and 31.

Some benefits of such an arrangement are that the headgear 300 is lightweight, doesn't go under the ears, which aids fitting, and is less bulky than conventional headgear.

In some configurations, additional straps 340 connect the mask 380 to the headgear 300. These could also be adjustable to provide improved customization of the fit. See, for example, FIGS. 30 and 31.

Figure 32:
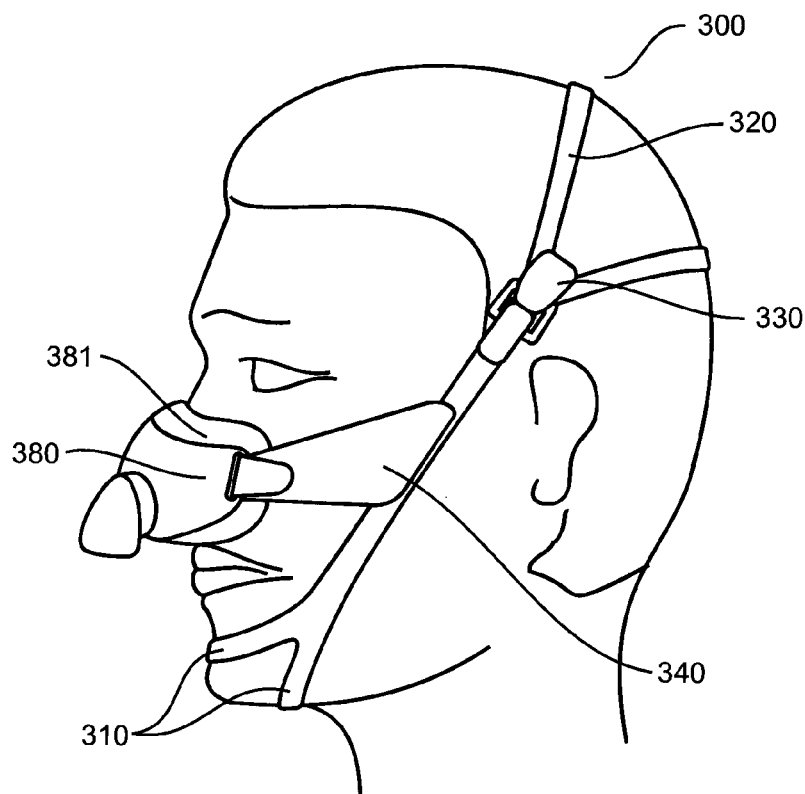
Figure 33:
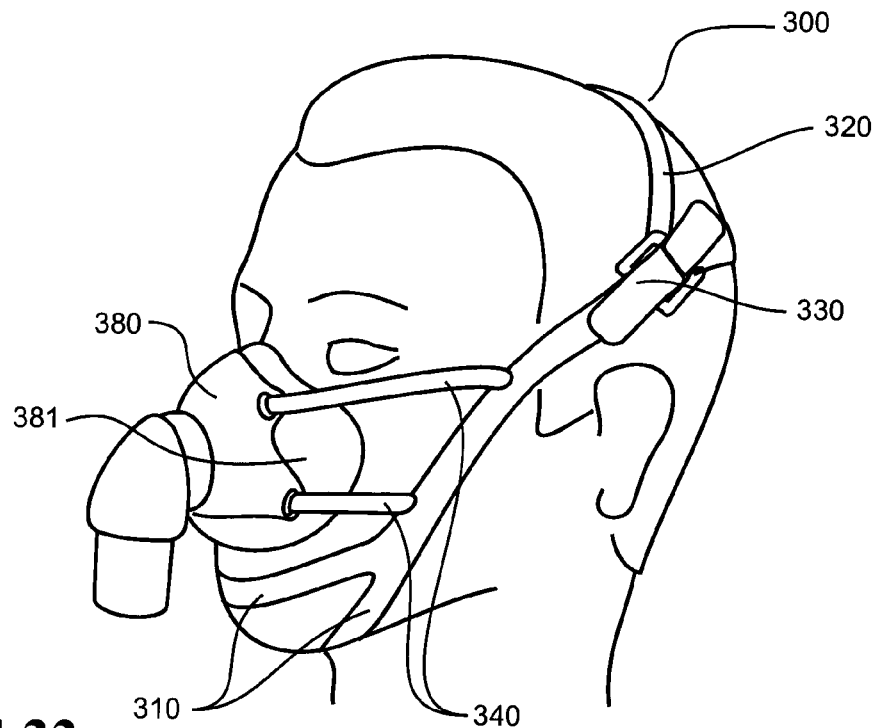
Figure 34:
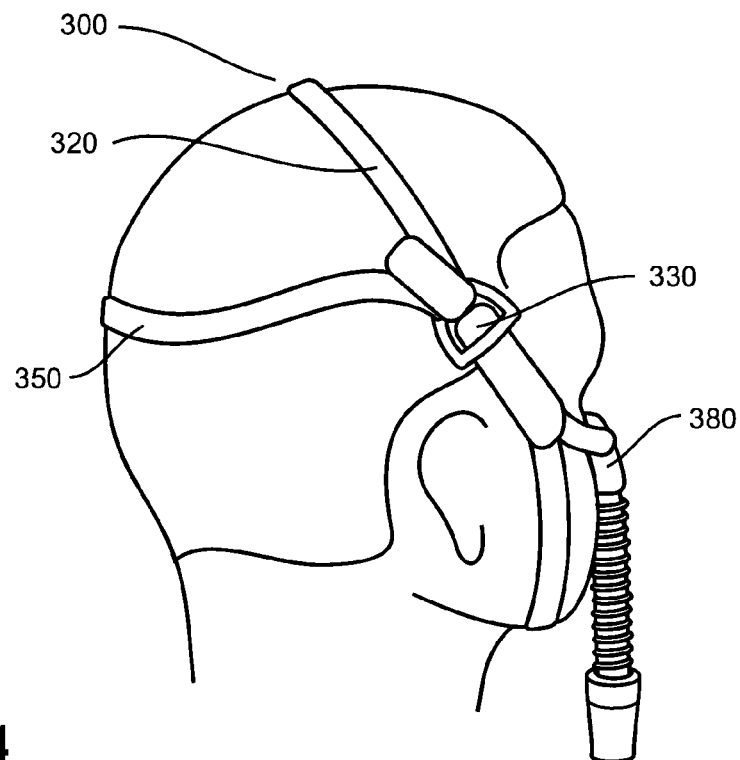
Figure 35:
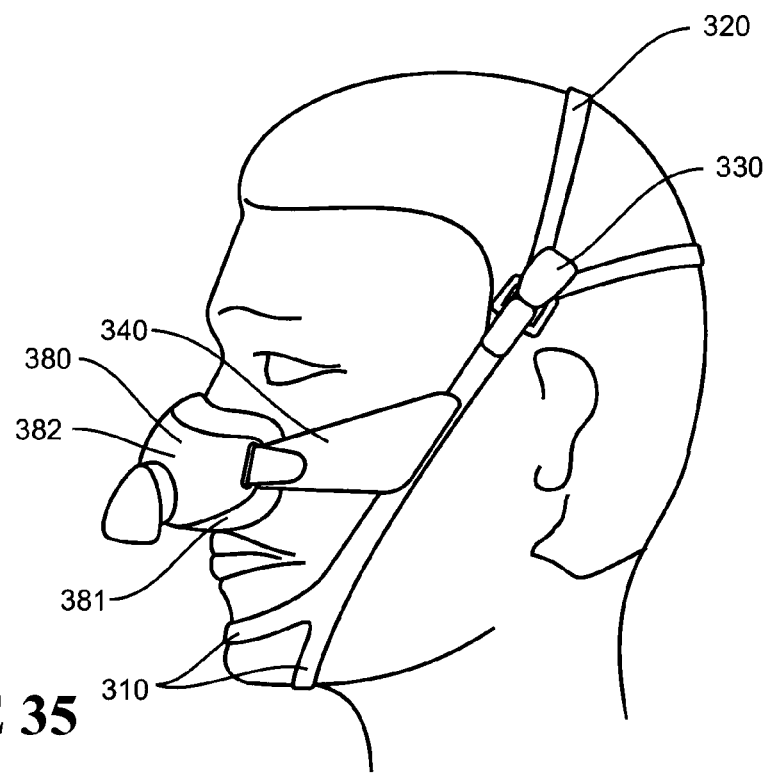
Figure 36:
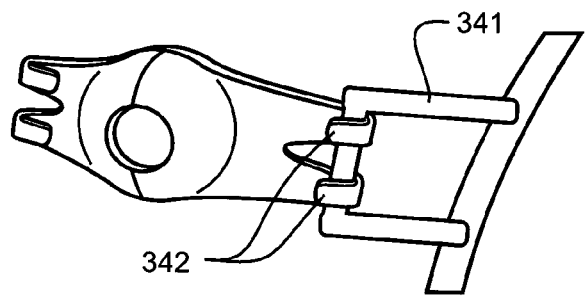
FIG. 36 illustrates an attachment structure for connecting a mask frame to stretch straps of any one of the embodiments of FIGS. 30 to 35, FIGS. 37 to 47A illustrate headgear embodiments comprising preferably a single elastic strap which loops around the top of the head and has a rigid or flexible plastic strap that is attached to the elastic strap above the ear and goes around the lower portion of the back of the head.
Figure 37:
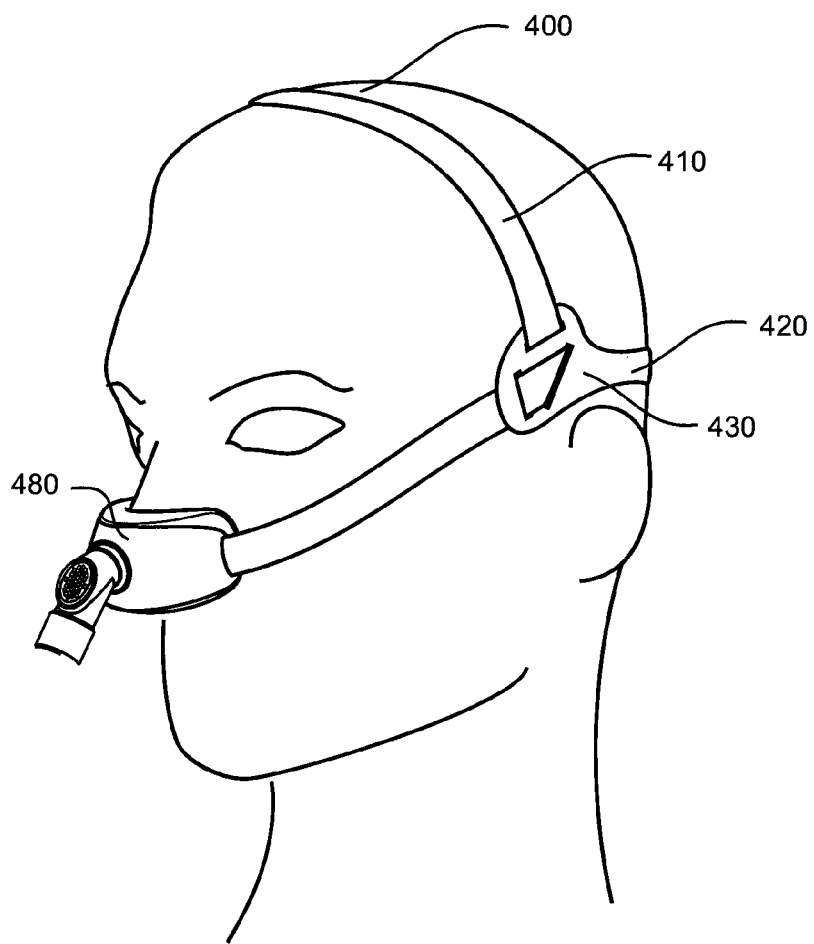
Figure 38:
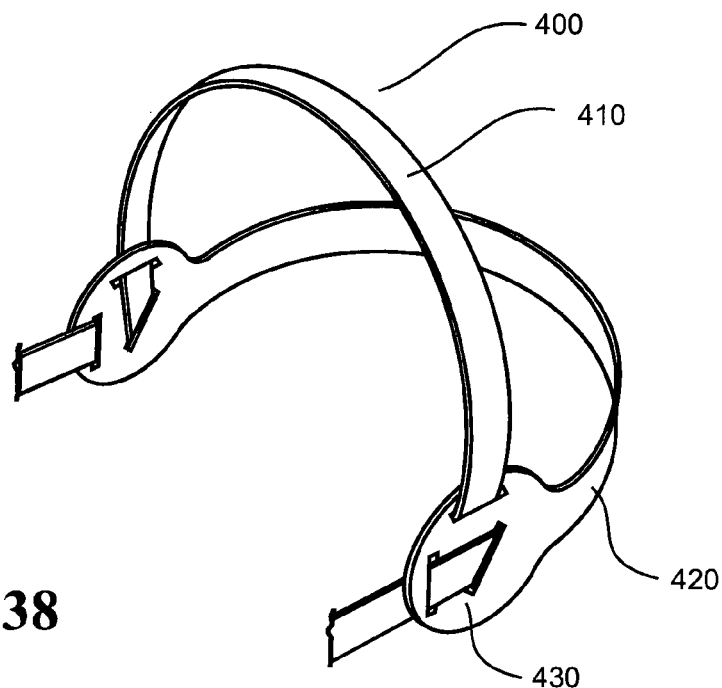
Figure 39:
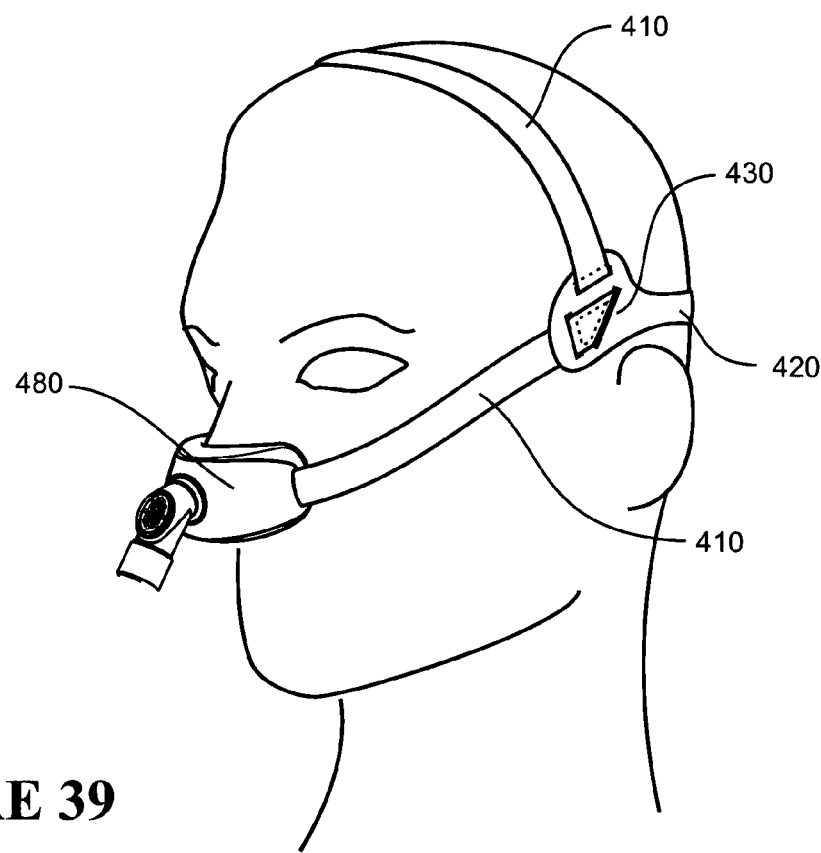
Figure 40:
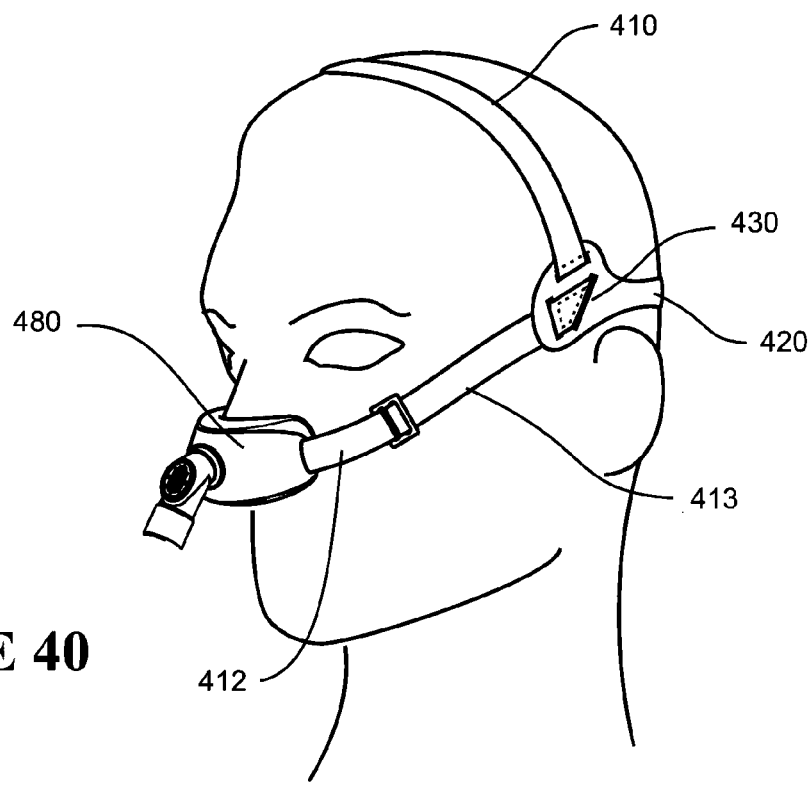
Figure 41:
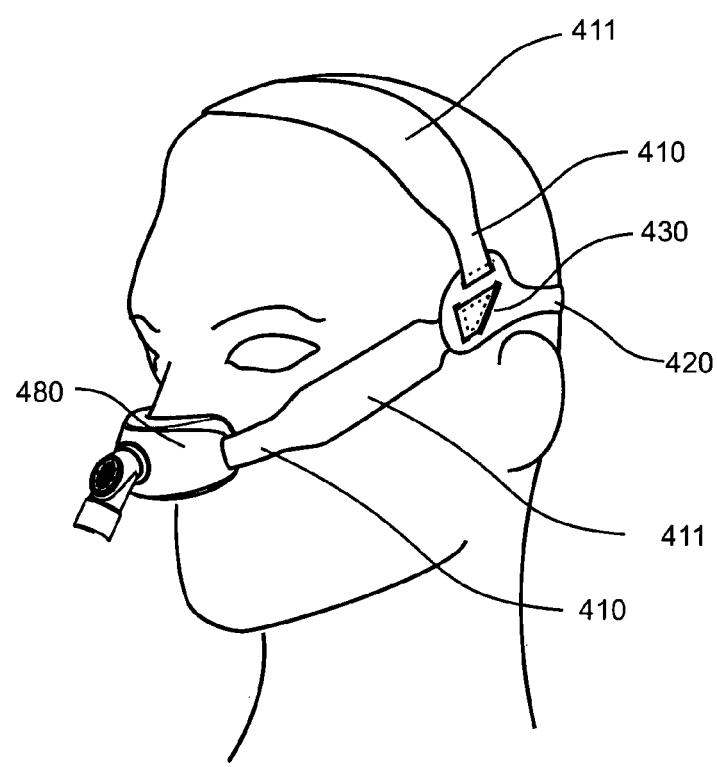
Figure 42:
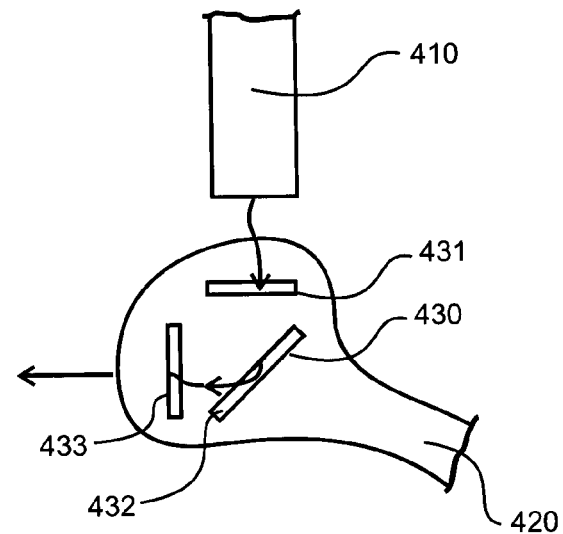
Figure 43:
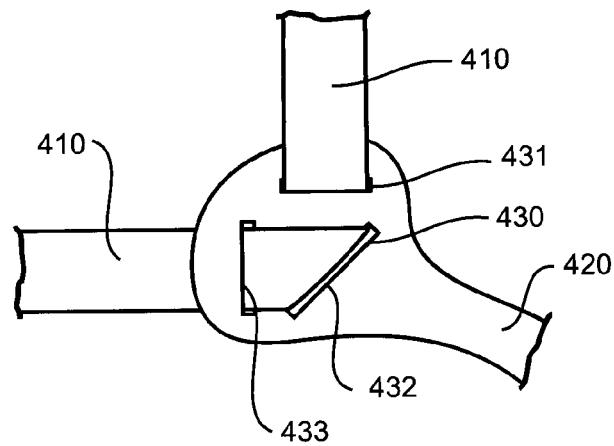
Figure 44:
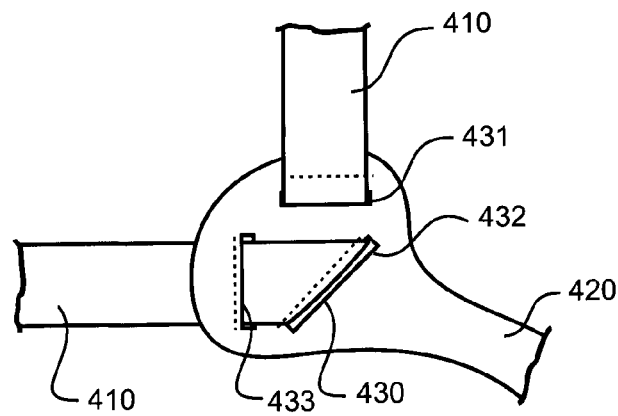
Figure 45:
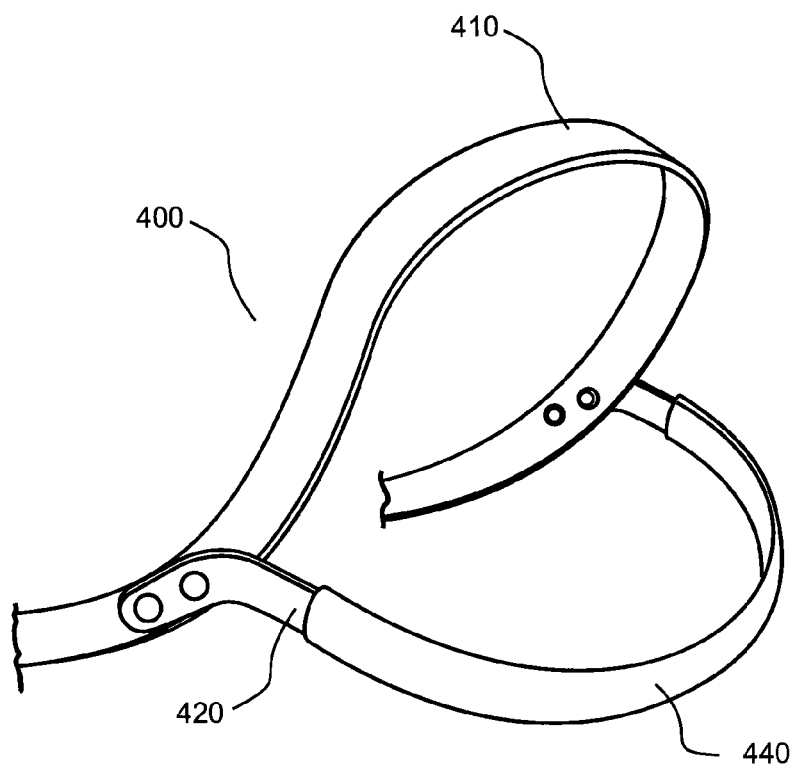
Figure 46:
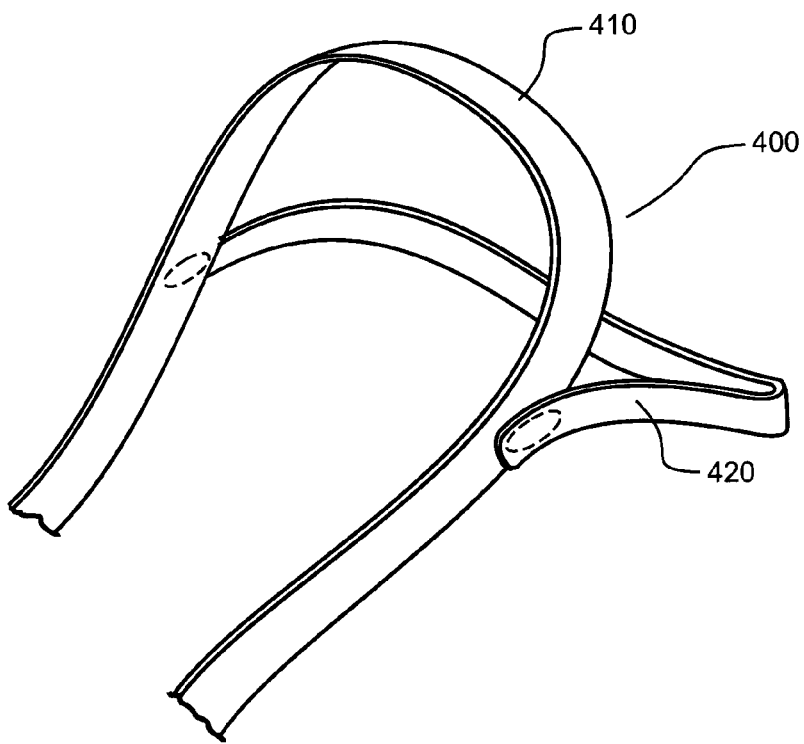
Figure 47A:
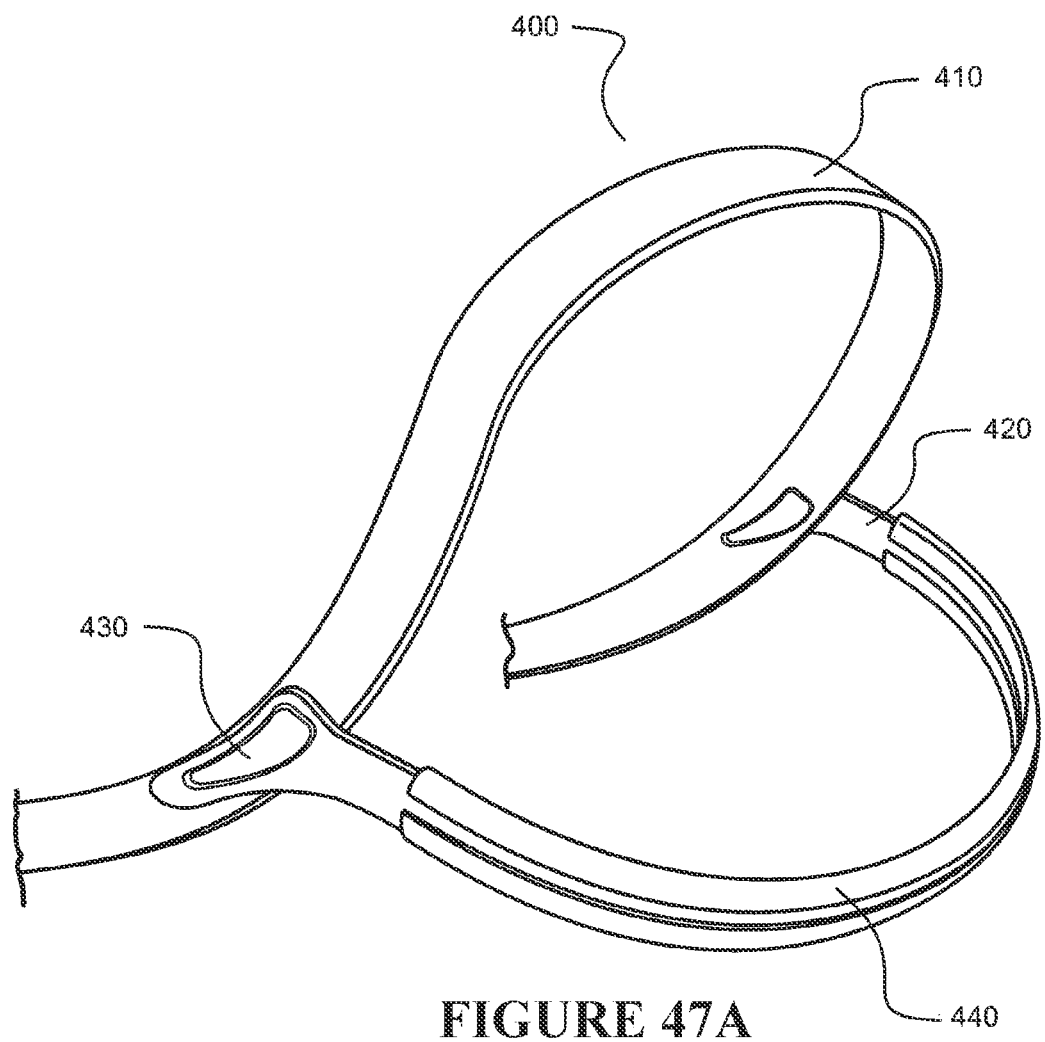
FIG. 47B is a cross-section of the plastic strap of FIG. 47A, FIGS. 48 to 62 illustrate nasal seal embodiments which have stabilising flaps to transfer the load of the sealing surface on to the cheeks instead of the lip and bridge of the nose.
Figure 47B:
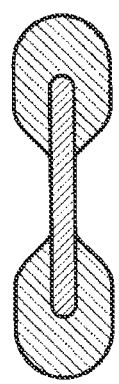
Figure 48:
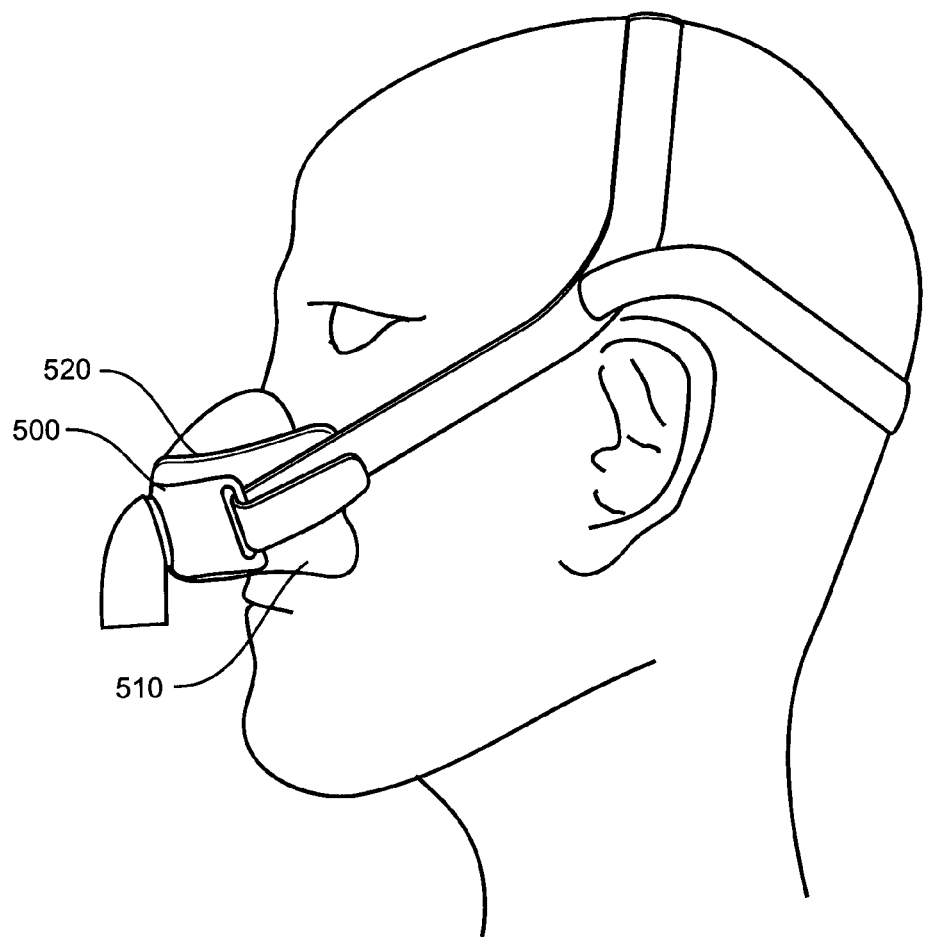
Figure 49:
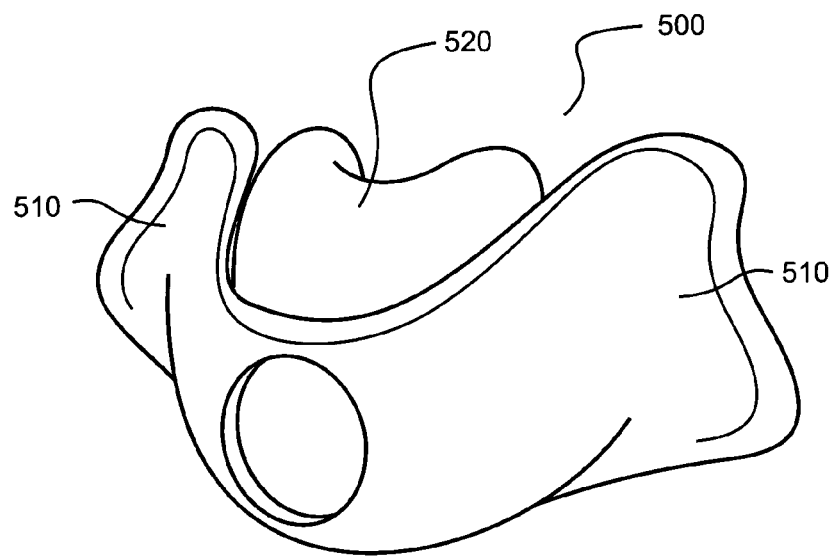
Figure 50:
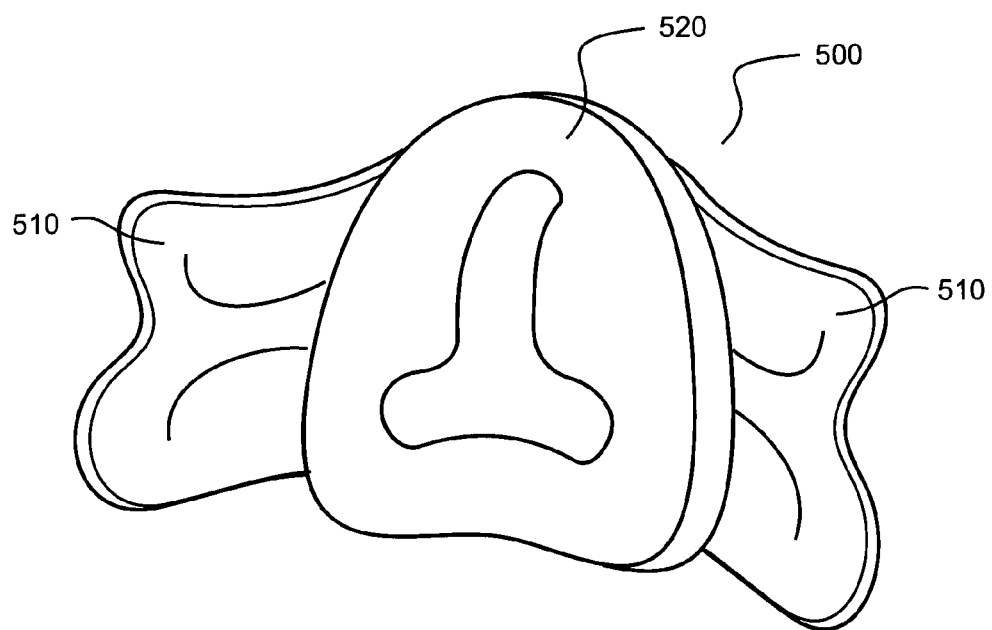
Figure 51:
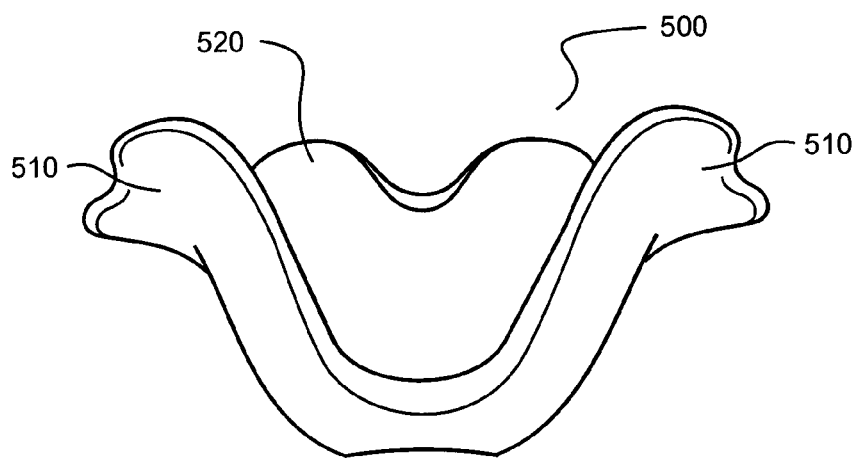
Figure 52:
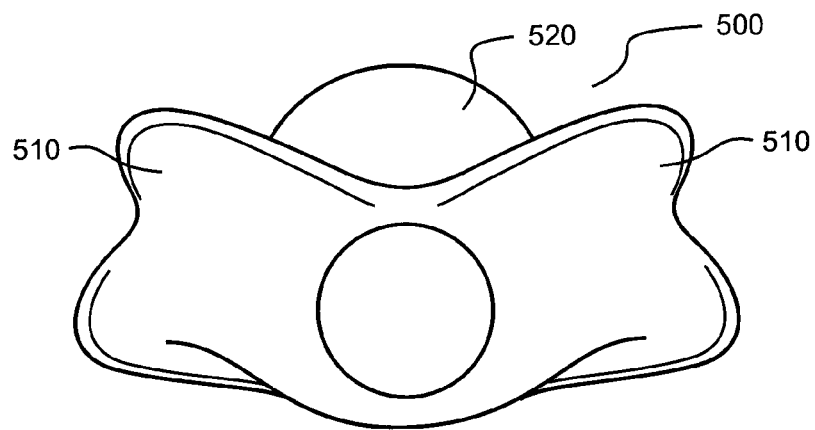
Figure 53:
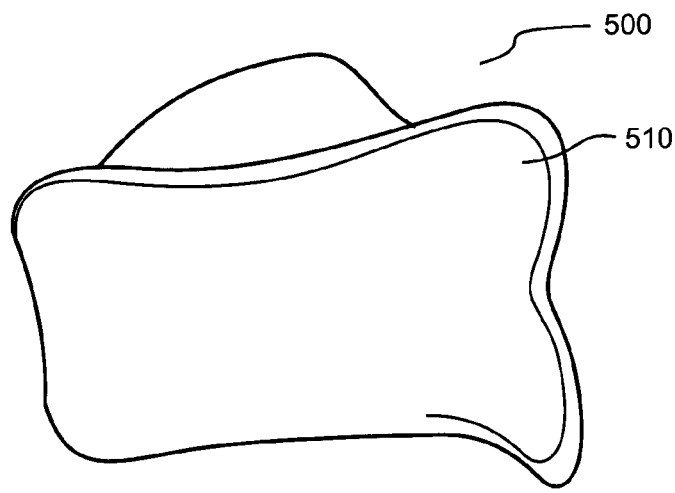
Figure 54:
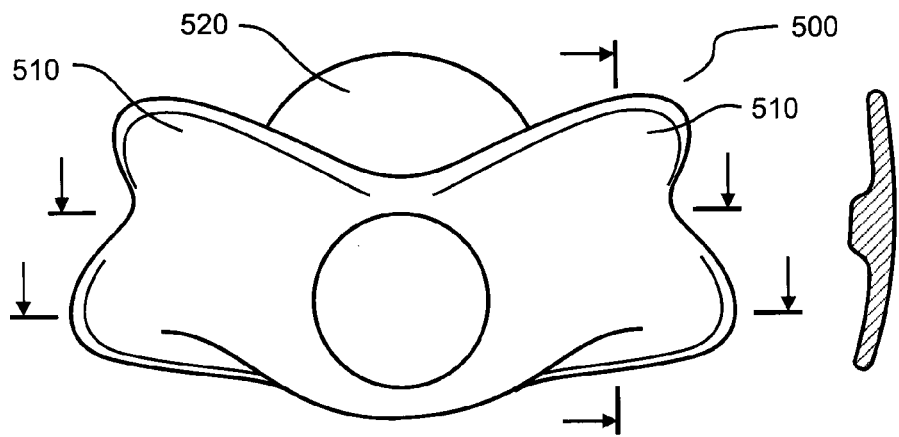
Figure 55:
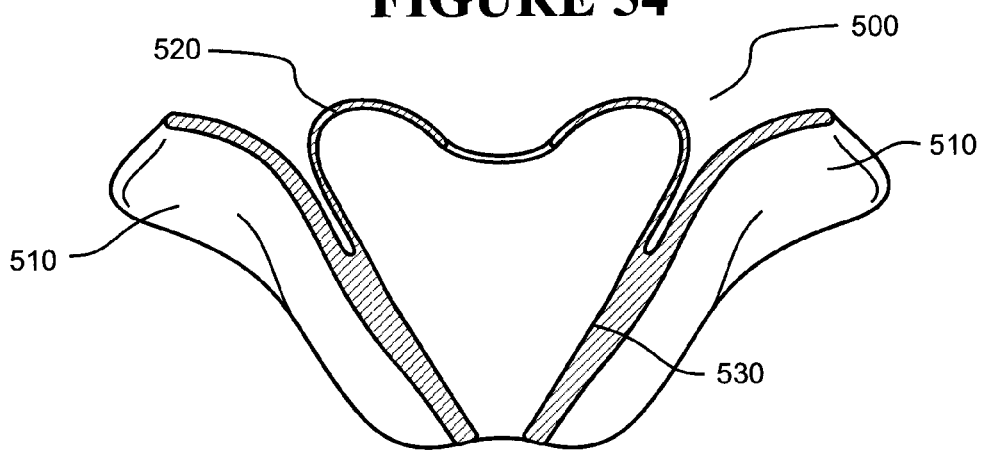
Figure 56:
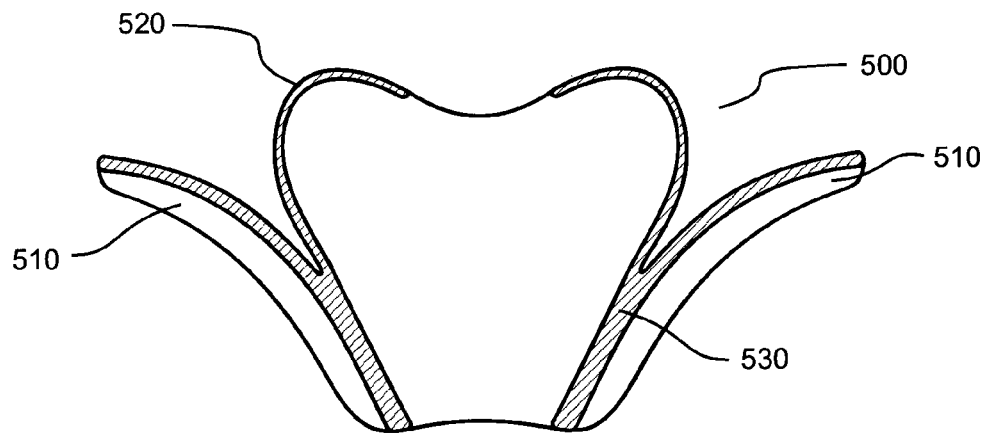
Figure 57:
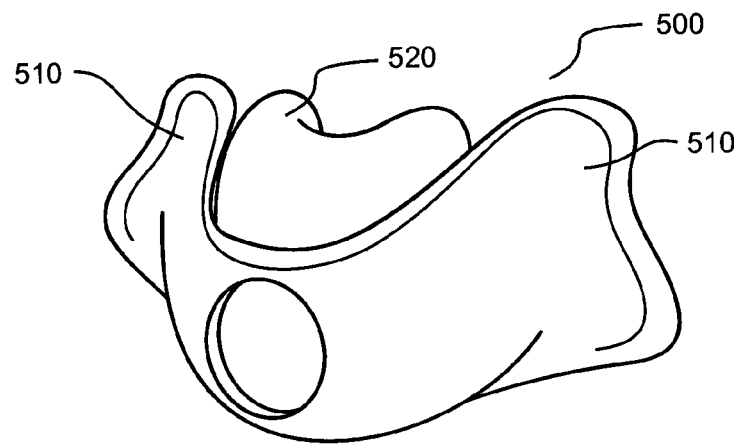
Figure 58:
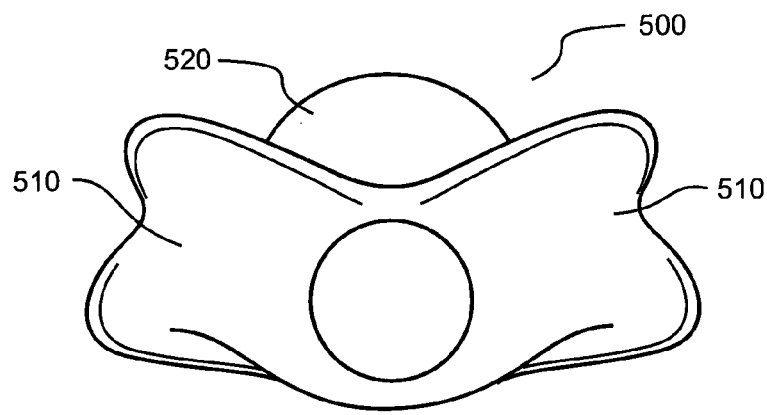
Figure 59:
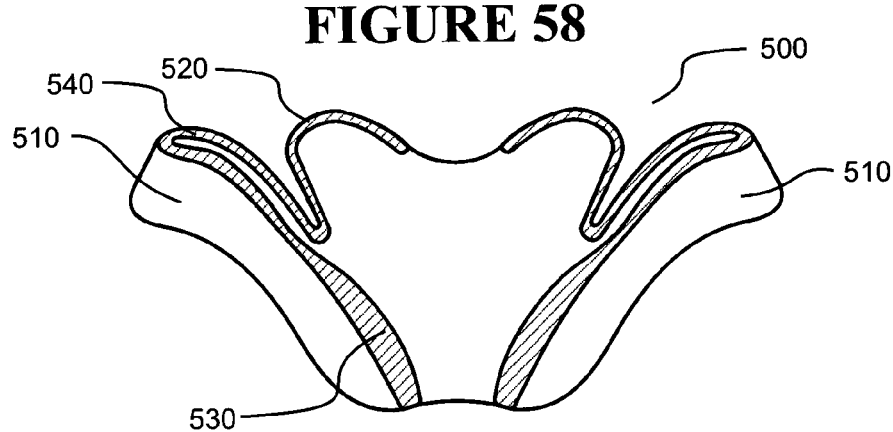
Figure 60:
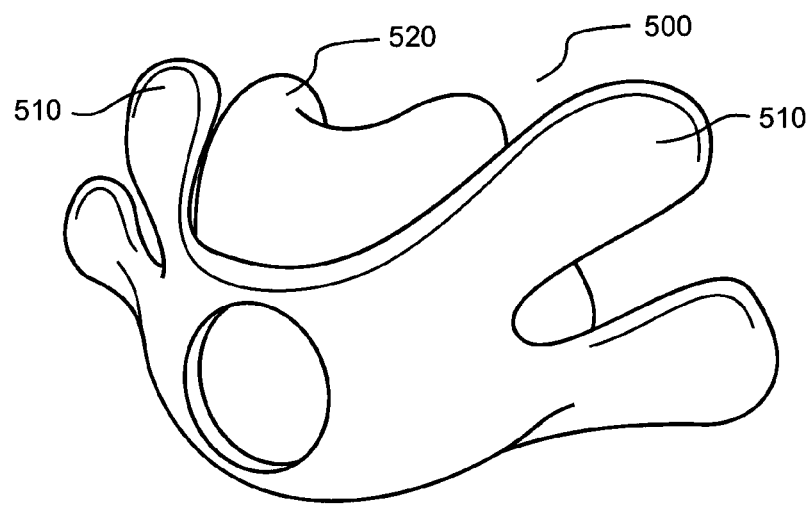
Figure 61:
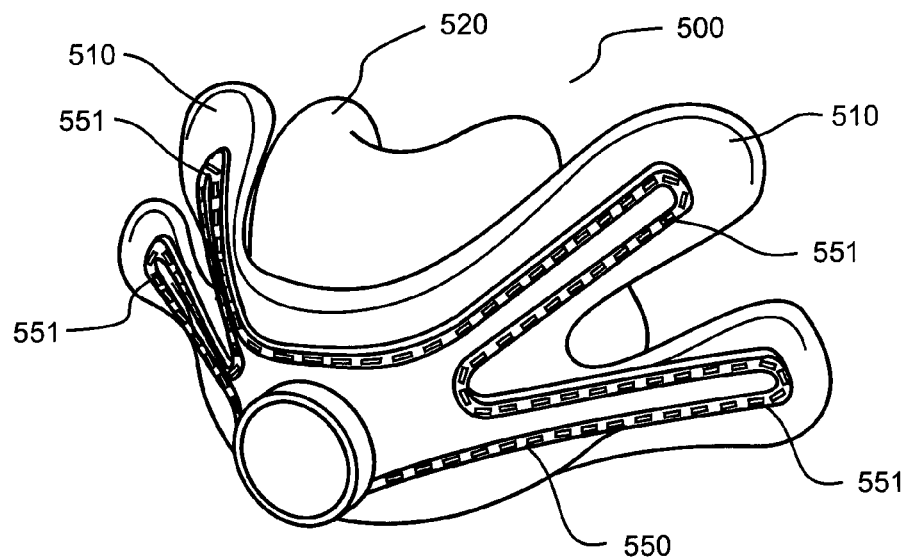
Figure 62:
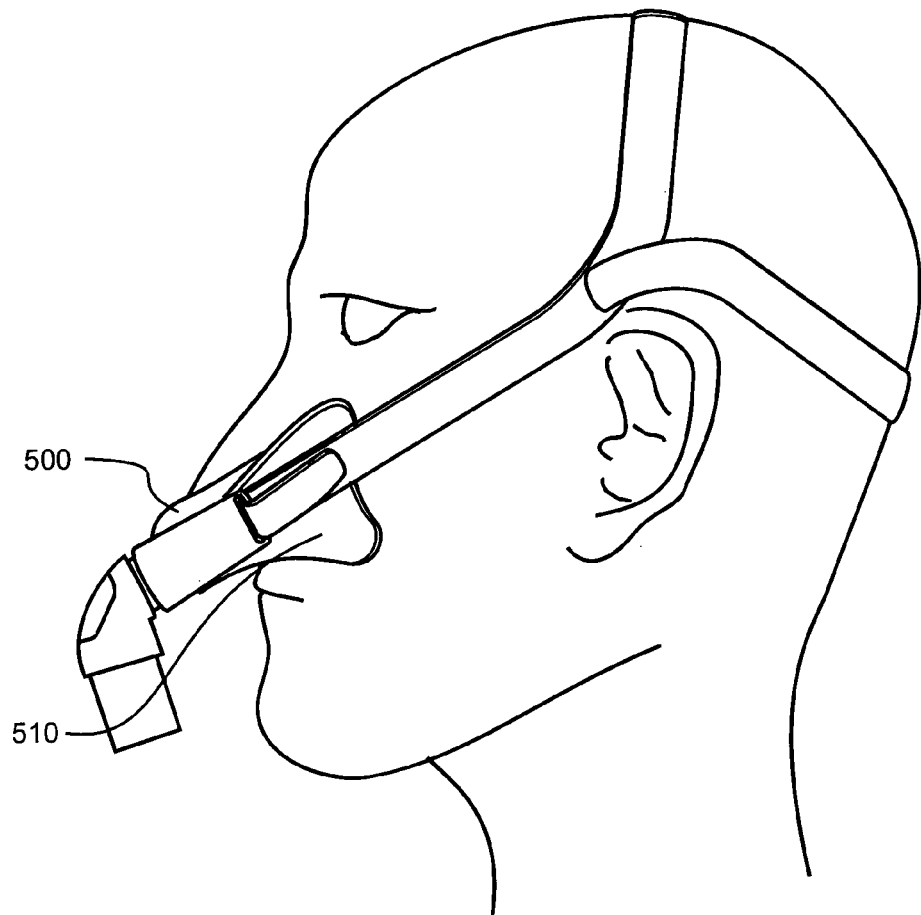

There could be a single or multiple mask attachment straps 340 on each side. FIG. 32 illustrates a single strap option.

In some configurations, the headgear 300 could be tightened so that it acts as a chinstrap, which would aid people who breathe through their mouth. See, for example, FIG. 32.

The headgear 300 is secure around the head and preferably doesn't rely on the mask seal 381 as an anchoring point. That is, the headgear 300 can stay on without a seal 381 attached. Advantageously, such an arrangement isolates the force of the seal from the force that keeps the headgear 300 on. This arrangement represents an advantageous difference relative to conventional headgear.

Such configurations could work well in combination with a full face mask 380 (FIG. 33) or a nasal mask 380 (see FIGS. 30, 32, 35 and 37). See, for example, FIG. 33.

In at least one embodiment, the strap 320 at the back could be split. In some such arrangements, the split portion of the strap 320 could comprise a rigid component 350. See, for example, FIG. 34.

In some configurations, the mask attachment straps 340 can comprise a loop 341 that sits over one or more hooks 342 or other retention structures on each side of the mask frame 382. See, for example, FIGS. 35 & 36.

FIGS. 37 to 47 illustrate headgear arrangements 400 comprising preferably a single elastic strap 410 which loops around the top of the head and has a rigid or flexible plastic strap 420 that is attached to the elastic strap above the ear and goes around the lower portion of the back of the head.

In some configurations, the rigid or flexible plastic strap 420 terminates at the attachment point 430 to the elastic strap above the ears. See, for example, FIGS. 37 and 46.

The rigid or flexible plastic strap 420 may be permanently attached by sewing, welding, rivets, crimping, or clipping, etc or a combination of these methods. In one preferred configuration, the rigid or flexible plastic strap 420 is attached by sewing. See, for example, FIGS. 44-41 and FIG. 46.

The elastic strap 410 may also be made up of a number of straps connected at the termination point 430 of the rigid or flexible strap 440 above the ears.

In at least one embodiment, a single elastic strap 410 may be attached or fed through a number of loop holes 431 to direct the strap to the desired angle, so that the strap sits on the top of the head and is redirected towards the hole 431 to provide the optimal position for attachment to the mask 480.

The strap 410 may be left unattached through the loop holes 431-433 in the attachment point to allow adjustability. See, for example, FIGS. 42 & 43.

The rigid or flexible plastic strap 420 may be covered by fabric or foam 440 etc. See, for example, FIGS. 45 & 47.

The plastic component 420 may be die cut or injection moulded etc. In one preferred embodiment, the plastic component or strap 420 is injection moulded.

The plastic component 420 may be textured to be pleasant/soft to the touch.

In one configuration, the elastic strap 410, which preferably is circular knitted, may be all the same width or diameter or wider in portions 411 for comfort. See, for example, FIG. 41.

In some configurations, the elastic strap 410 can have stretch 412 and non-stretch 413 areas. See, for example, FIG. 40.

Other Seals

FIGS. 48 to 62 illustrate nasal seals 500 which have stabilising flaps 510 to transfer the load of the sealing surface on to the cheeks instead of the lip and bridge of the nose. This allows the seal 500 to be thin (for example, 0.1 mm-0.5 mm) and, in some configurations, inflatable to conform around the nose and create a leak free and comfortable seal. There can be supporting sections 530 in the silicone seal 500 which are thicker (e.g., portions of a greater wall thickness or other structures to provide increased stiffness relative to other portions of the seal 520).

The stabilising flaps 510 can be more rigid and structured than the seal, but still flexible enough to conform to the facial features without causing pressure sores. See, for example, FIG. 51.

The flaps 510 can be sized and shaped to sit on the side of the nose and preferably within the cheek area. See, for example, FIG. 48.

Preferably, the stabilising flaps 510 disperse the loading force of the seal evenly or more evenly on the face relative to existing nasal masks, so that there is not a single point or small area of pressure or loading.

Preferably, the flaps 510 are wide enough to minimise upwards movement of the seal into the eyes as well as providing lateral stability on the nose. See, for example, FIG. 49.

In some configurations, the internal seal 520 can sit like a conventional nasal seal over the bridge of the nose and around the sides of the nose and over the top lip. See, for example, FIG. 48.

The flaps 510 can be integrated with the sealing surface 520 in at least one embodiment, and be made of the same material. In such an embodiment, each of the flaps 510 has one or more thicker sections 530 to provide stiffness as well as thin sections 540 for flexibility for a desired or optimum balance between stability and weight.

In some configurations, the sealing surface 520 can avoid contact with the bridge of the nose. This could be in combination with integral stabilising flaps 510, or with separate stabilising flaps 510. See, for example, FIG. 62.

In some configurations, the flaps 510 can be split to fit better on the face or fit better on certain facial geometries. See, for example, FIG. 61.

In some configurations, the flaps 510 can be hollow to conform better to a variety of facial geometries. See, for example, FIGS. 57-59.

In at least one embodiment, the seal 500 can be overmoulded onto a plastic component 550 which has arms 551 that add stiffness to the flaps, instead of or in addition to using thick wall sections of soft elastomeric material. In such an arrangement, the plastic component 550 can be a stiffening member. See, for example, FIG. 61.

In some configurations, the flaps 510 can be separate from the sealing portion 520. The flaps 510 may be different materials, such as breathoprene, thermoformed breathoprene or foam, or foamed silicone, etc.

The seals of FIGS. 48-62 work well in combination with any 2 point headgear, for example, the headgear arrangements 200 and 400 described herein with respect to FIGS. 25 to 29 and FIGS. 37 to 47 respectively.

Figure 63:
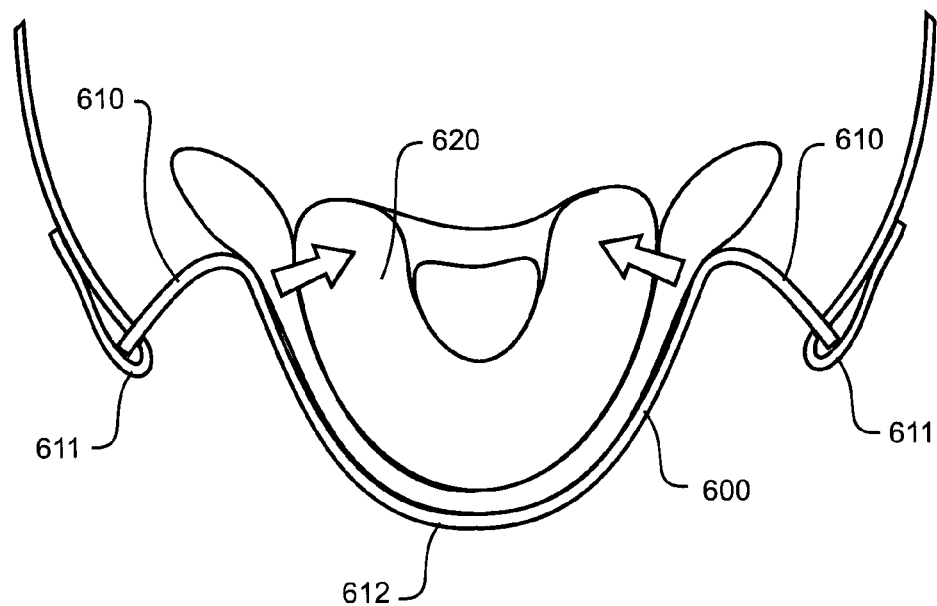
FIG. 63 illustrates a flexible mask frame embodiments for OSA masks with arms that cause the frame to pinch inwards against the seal when the headgear is tightened.
Figure 64:
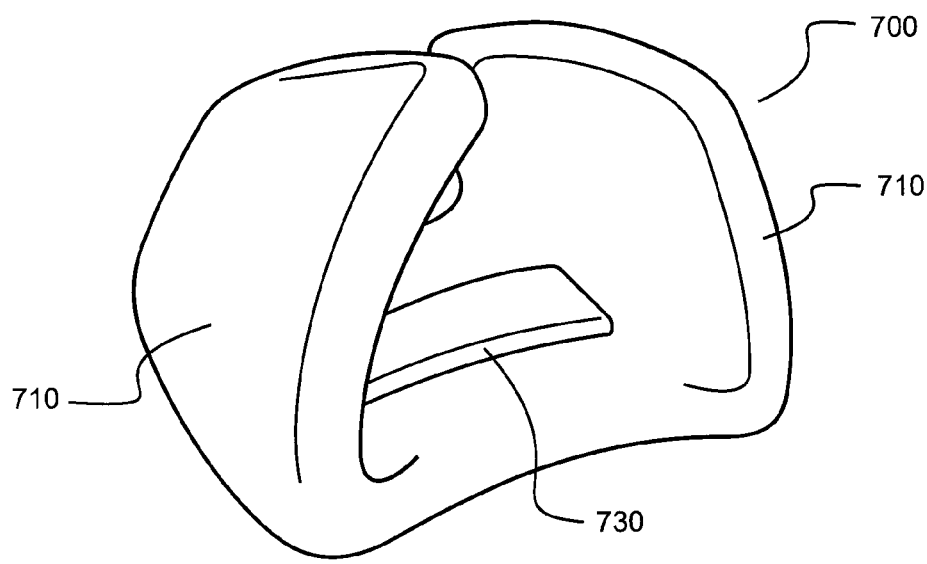
FIGS. 64 to 82 illustrate inflating nasal seal embodiments that sit under the nose and comprises wings which extend around the sides of the nose, preferably below the eyes and avoiding the bridge of the nose.
Figure 65:
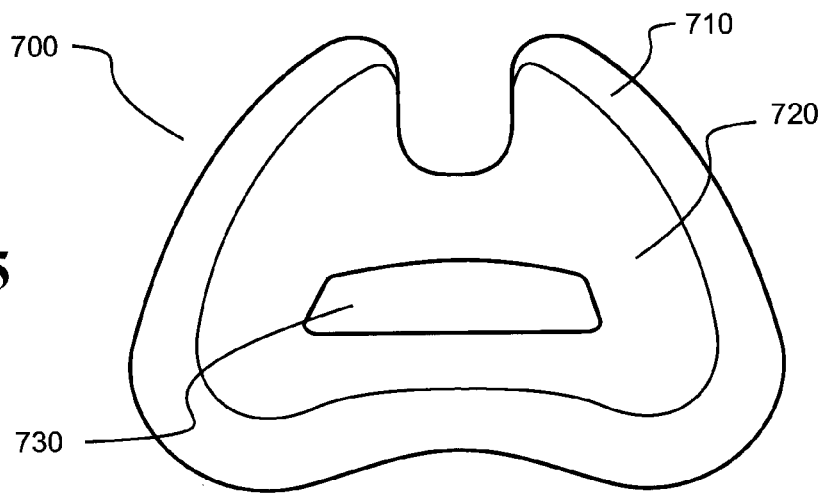
Figure 66:
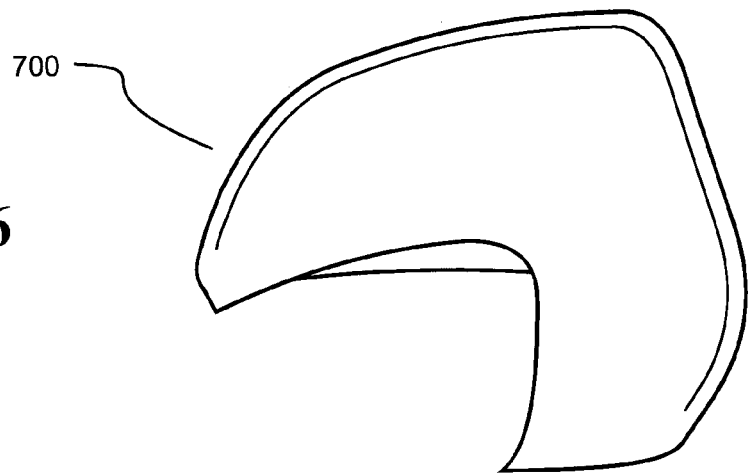
Figure 67:
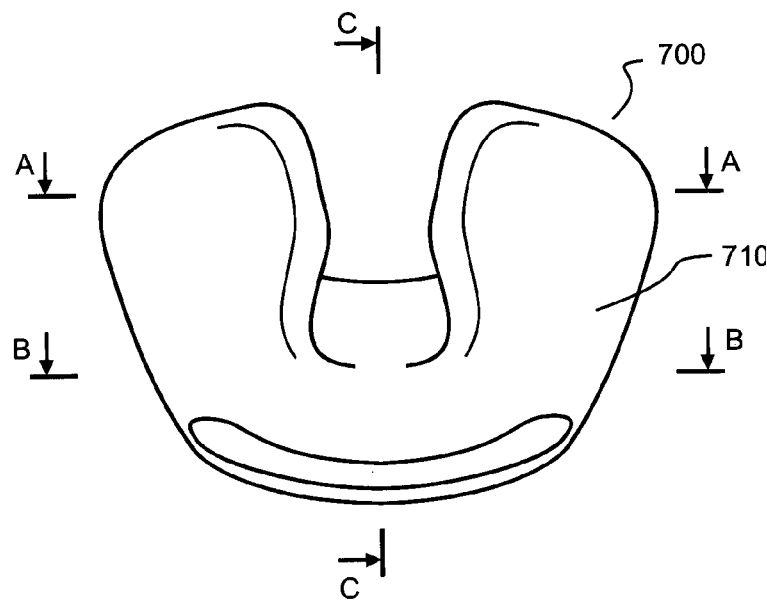
Figure 68:
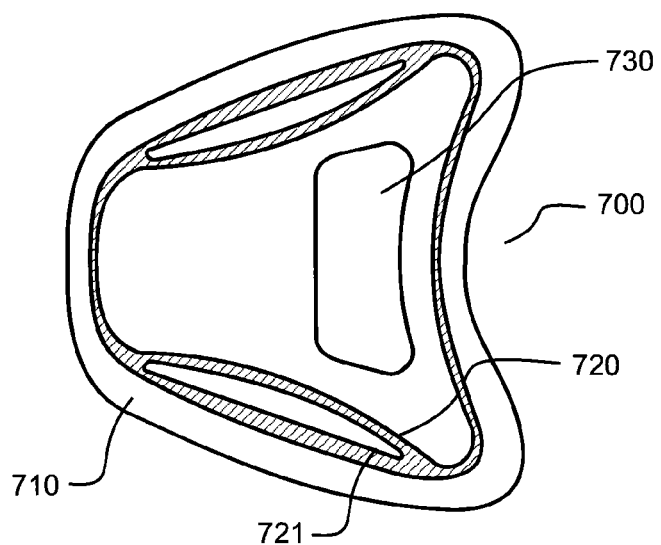
Figure 69:
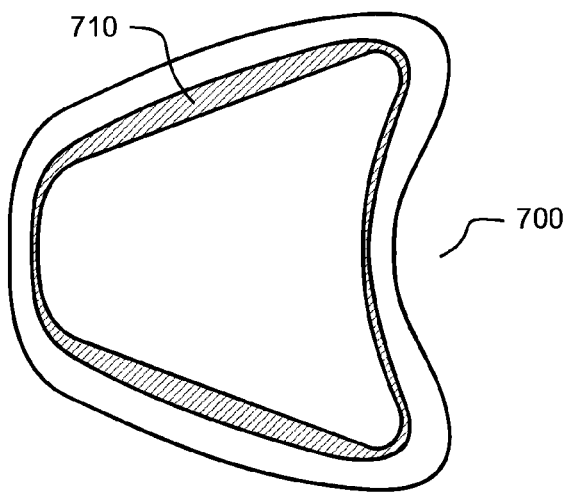
Figure 70:
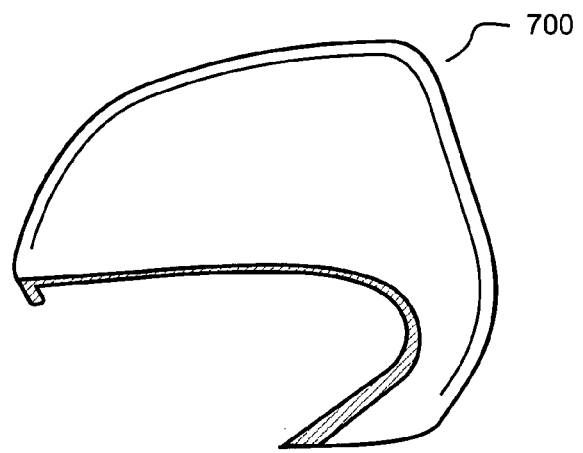
Figure 71:
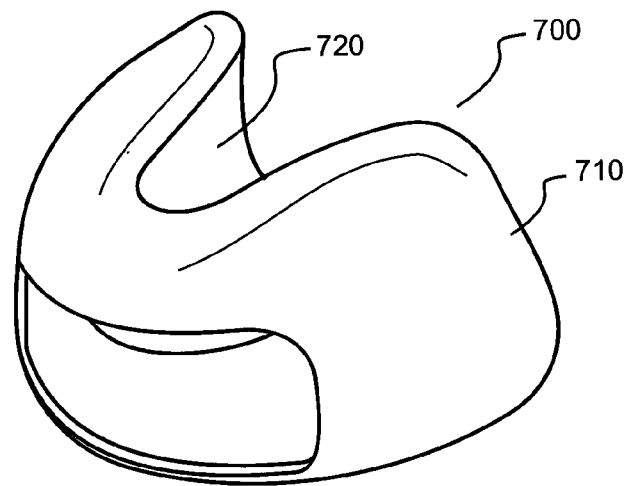
Figure 72:
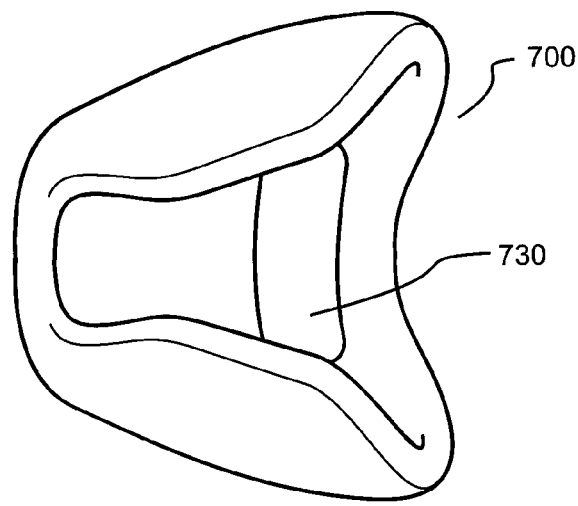
Figure 73:
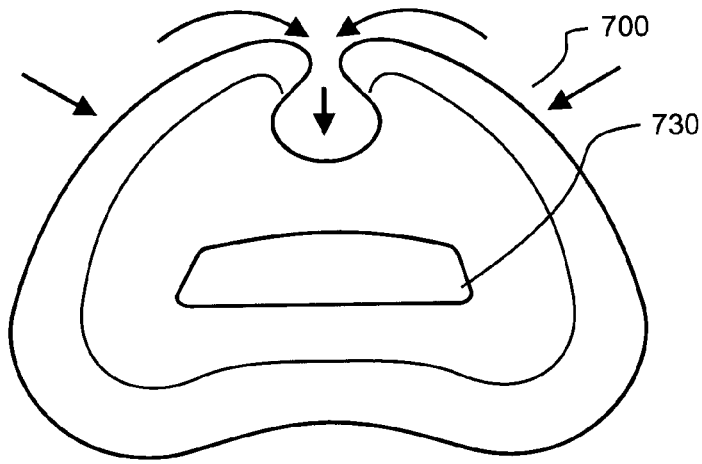
Figure 74:
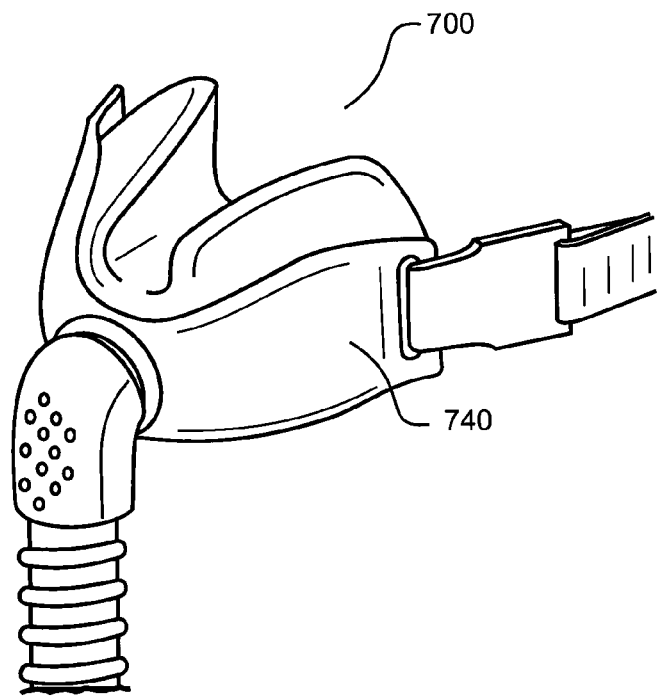
Figure 75:
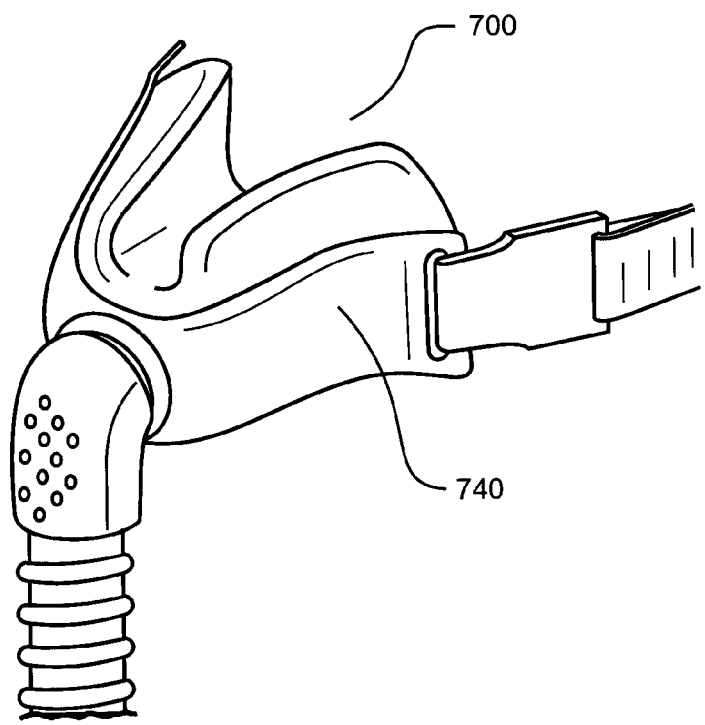
Figure 76:
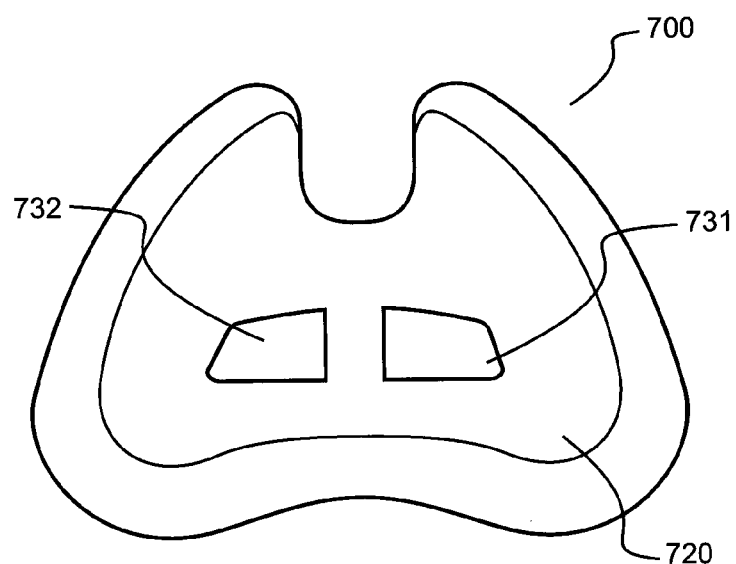
Figure 77:
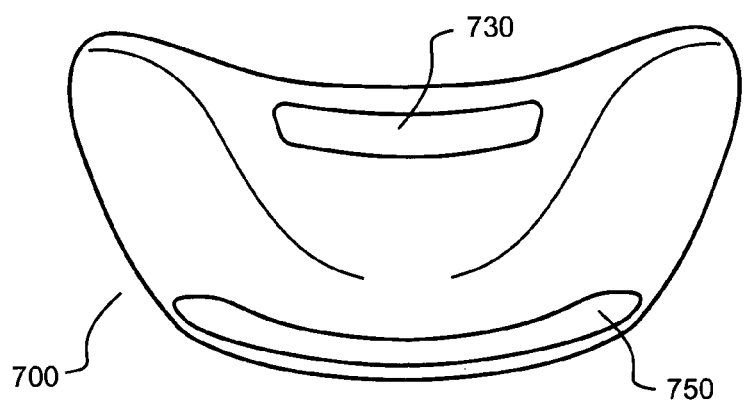
Figure 78:
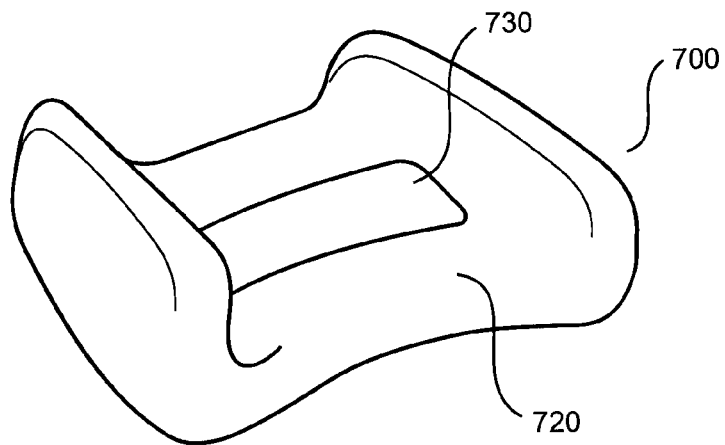

FIG. 63 illustrates a flexible mask frame 600 for OSA masks with arms 610 that cause the frame 600 to pinch inwards against the seal 620 when the headgear 630 is tightened. For example, the arms 610 could extend outwardly (away from the face of a user) to an attachment portion 611. Such an arrangement causes end portions 611 of a generally or substantially U-shaped central portion 612 of the mask frame 600 to flex inwardly to pinch the seal 620. Such an arrangement helps to hold the seal 620 more snugly against the nose, thereby improving the seal and/or stability.

Other Seals

Figure 79:
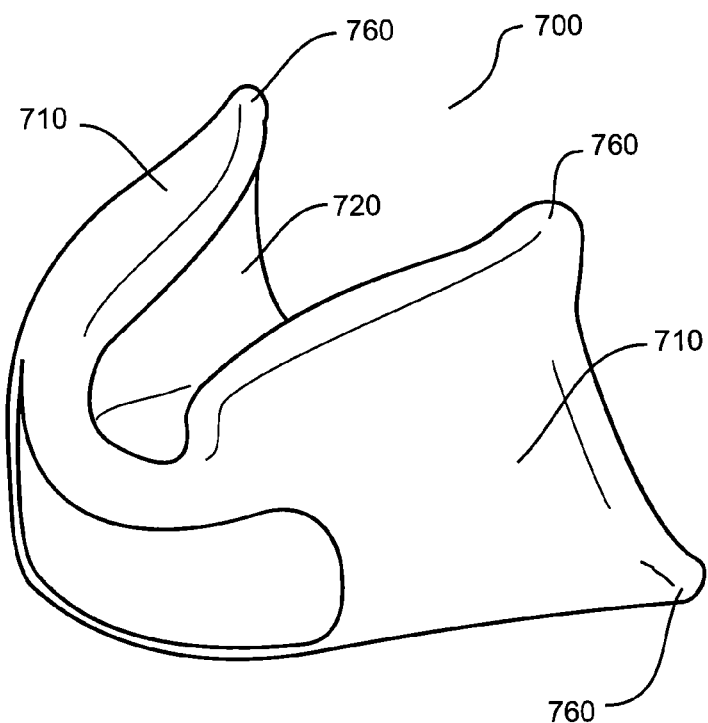
Figure 80:
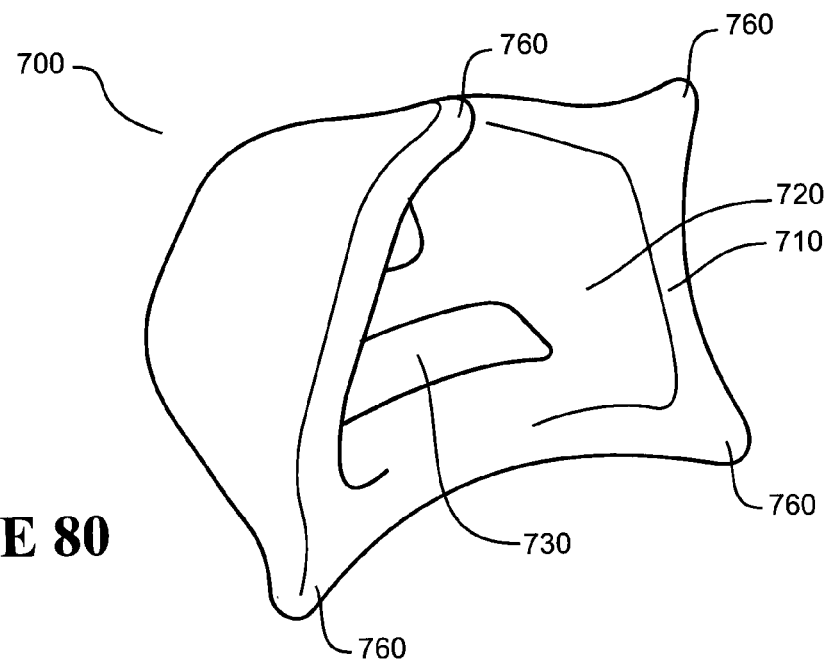
Figure 81:
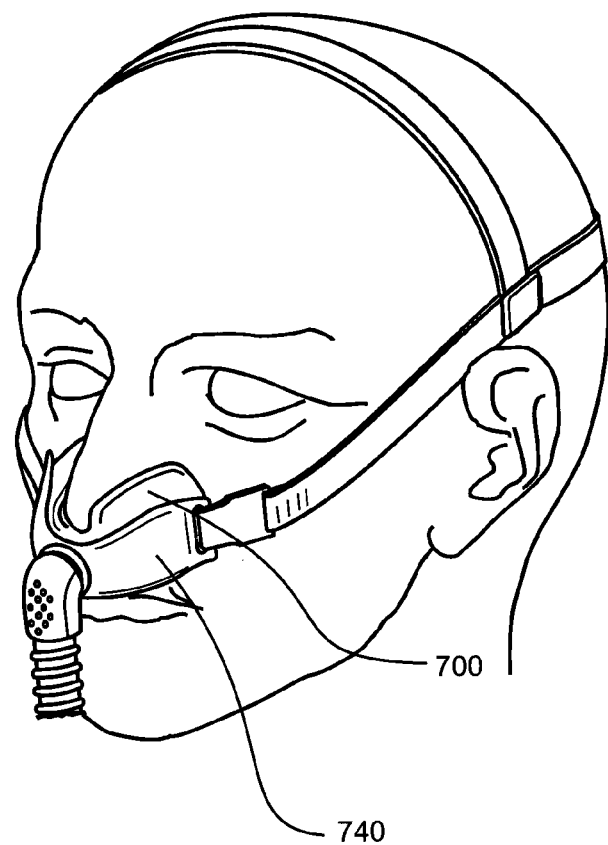
Figure 82:
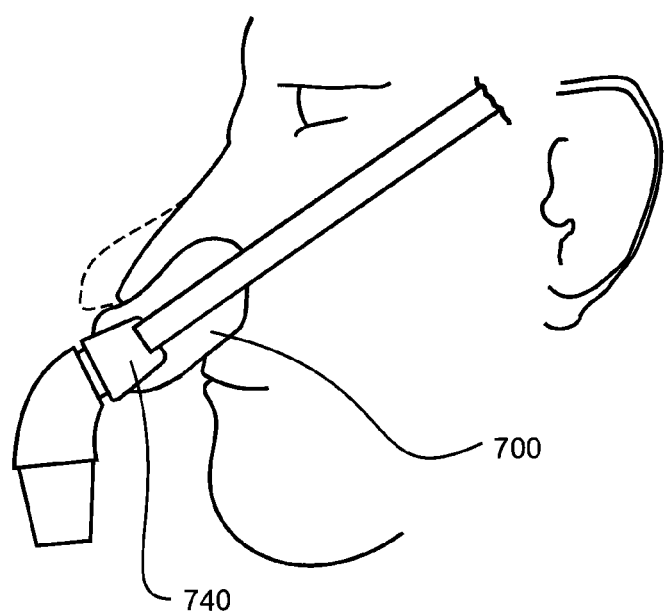

FIGS. 64 to 82 illustrate inflating nasal seals 700 that sit under the nose and comprises wings 710 which extend around the sides of the nose, preferably below the eyes and avoiding the bridge of the nose. See, for example, FIG. 79.

In some configurations, the wings 710 are shaped to sit in the transition between the nose and the cheeks on both sides for stability, to prevent leaks and tolerate movement of the seal 700.

In some configurations, the seal 700 is small enough that the tip of the nose is exposed to accommodate different sized noses. See, for example, FIG. 82.

In some configurations, the sealing portion 720 is relatively thin (such as about 0.1 mm-0.5 mm) but may be thicker in certain areas 721 to provide structure (e.g., greater stiffness). See, for example, FIG. 68.

In some configurations, downward pressure on the lower sealing surface 720 pulls the wings 710 inwards in a pinching motion, creating a better seal and a more secure fit. See, for example, FIG. 73.

In some configurations, the outside wall of one or more portions of the seal (e.g., the wings 710) is substantially thicker that the inside wall 720 to direct the inflation inwards and to push the inflating portion 720 against the face. See, for example, FIG. 68.

In some configurations, there is a single opening 730 for airflow to the nostrils. However, in other configurations, there could be two or more openings 730 for airflow to the nostrils.

In some configurations, the seal 700 may include the tip of the nose being contacted or partially or completely covered by the inflating portion to provide a better seal. See, for example, FIG. 71.

The nasal seal 700 may be used in combination with a mask frame 740 which is flexible enough to pinch the seal in towards the nose to provide a closer fit and a better seal. See, for example, FIG. 75.

As described above, in some configurations, the nasal seal 700 may have separate openings 731 and 732 for each nostril. See, for example, FIG. 76.

In at least one configuration, the inflating nasal seal 700 does not have wings, just a pad 750 under the nose. See, for example, FIG. 77.

In some configurations, the nasal seal 700 may have small angled projections 760 at the top and/or bottom corners of the seal 700 which can aid stability of the seal. See, for example, FIGS. 79-80.

One or more configurations of the nasal seal 700 of FIGS. 64-82 can be configured to work well with the Headgear 400 described herein with respect to FIGS. 37 to 47.

The foregoing describes the invention including preferred forms thereof and alterations and modifications as will be obvious to one skilled in the art are intended to be incorporated in the scope hereof.

The invention claimed is:

1. A nasal seal for a mask interface, the nasal seal comprising:
   a wearer side comprising:
   a nose-receiving portion having a concave shape and configured to sealingly contact a tip, lower sides, and base of a nose of a wearer and to sealingly contact an upper lip of the wearer, and
   an aperture for gas flow configured to be positioned beneath nares of the wearer; and
   an external side comprising:
   an opening configured to pass gas flow to the wearer through the aperture,
   a first stabilizing portion that extends on a first side of the opening,
   a first fold comprising a pair of spaced-apart first sidewall portions connected by an arcuate first end wall, the first fold configured to provide transverse movement of the first stabilizing portion,
   a second stabilizing portion that extends on a second opposite side of the opening,
   a second fold comprising a pair of spaced-apart second sidewall portions connected by an arcuate second end wall, the second fold configured to provide transverse movement of the second stabilizing portion,
   wherein an entirety of the first fold is positioned on the first stabilizing portion and an entirety of the second fold is positioned on the second stabilizing portion, the first fold and the second fold are discontinuous from one another such that a top wall of the external side of the nasal seal is uninterrupted by the first fold and the second fold and a bottom wall of the external side of the nasal seal is uninterrupted by the first fold and the second fold, and
   wherein a thickness of the first stabilizing portion is greater than a thickness of the first fold and a thickness of the second stabilizing portion is greater than a thickness of the second fold.

2. The nasal seal of claim 1, wherein the first fold and the second fold are directed into an interior of the nasal seal.

3. The nasal seal of claim 1, wherein the first fold and the second fold extend partially in a depth of a hollow interior of the nasal seal.

4. The nasal seal of claim 1, wherein the first fold and the second fold extend partially across a width of a hollow interior of the nasal seal.

5. The nasal seal of claim 1, wherein the nose-receiving portion comprises a left side wall and a right side wall to contact a left lower side of the nose and a right lower side of the nose of the wearer.

6. The nasal seal of claim 5, wherein at least an upper section of the left side wall and an upper section of the right side wall have a convex shape on opposite sides of the nasal seal.

7. The nasal seal of claim 6, wherein the convex shape of upper sections of a left side wall and a right side wall are above the aperture in a height of the nasal seal.

8. The nasal seal of claim 1, wherein the nose-receiving portion comprises an upper wall portion above the aperture to contact the tip of the nose of the wearer, a lower wall portion below the aperture, and rearward of the upper wall portion to contact the upper lip below the nose of the wearer.

9. The nasal seal of claim 8, wherein the upper wall portion and the lower wall portion have discrete curved shapes.

10. The nasal seal of claim 1, wherein a wall thickness of the nasal seal reduces from the external side of the nasal seal to the wearer side of the nasal seal.

11. The nasal seal of claim 1, wherein the first fold is the only fold in the first stabilizing portion and the second fold is the only fold in the second stabilizing portion.

12. The nasal seal of claim 1, wherein the nasal seal has a forward side closer to the opening and a rearward side further from the opening, wherein a portion of the first stabilizing portion is located on each of the forward side and the rearward side of the first fold, and a portion of the second stabilizing portion is located on each of the forward side and the rearward side of the second fold.

13. The nasal seal of claim 1, wherein the opening defines a length axis of the nasal seal, wherein the first fold and the second fold are located an equal distance from the opening along the length axis.

14. An interface comprising:
a seal comprising:
an inner side configured to create a sealing contact between a nose and an upper lip of a patient,
an opening configured to pass gas flow to the patient,
an outer side comprising:
a first stabilizing portion that extends on a first side of the opening,
a single first fold comprising a pair of spaced-apart first sidewall portions connected by an arcuate first end wall, the first fold configured to provide transverse movement of the first stabilizing portion,
a second stabilizing portion that extends on a second opposite side of the opening,
a single second fold comprising a pair of spaced-apart second sidewall portions connected by an arcuate second end wall, the second fold configured to provide transverse movement of the second stabilizing portion,
wherein an entirety of the first fold is positioned on the first stabilizing portion and an entirety of the second fold is positioned on the second stabilizing portion, the first fold and the second fold are discontinuous from one another, and
wherein a thickness of the first stabilizing portion is greater than a thickness of the first fold and a thickness of the second stabilizing portion is greater than a thickness of the second fold; and
a frame configured to retain the seal and move transversely relative to the inner side of the seal without breaking the sealing contact.

15. The interface of claim 14, wherein the first fold and the second fold of the seal are directed into an interior of the seal.

16. The interface of claim 14, wherein the first fold and the second fold of the seal extend partially in a depth of a hollow interior of the seal.

17. The interface of claim 14, wherein the first fold and the second fold of the seal extend partially across a width of a hollow interior of the seal.

18. The interface of claim 14, wherein the inner side further comprises a nose-receiving portion comprising a left side wall and a right side wall to contact a left lower side and a right lower side of the nose of the patient.

19. The interface of claim 18, wherein at least an upper section of the left side wall and an upper section of the right side wall have a convex shape on opposite sides of the seal.

20. The interface of claim 18, wherein the nose-receiving portion comprises an upper wall portion above an aperture to contact a tip of the nose of the patient, a lower wall portion below the aperture, and rearward of the upper wall portion to contact the upper lip below the nose of the patient.

21. The interface of claim 20, wherein the upper wall portion and the lower wall portion have discrete curved shapes.

22. The interface of claim 14, wherein the frame comprises left and right side arms which extend outwardly and rearwardly past left and right extremities of the seal, wherein the left and right side arms extend upwardly at an angle selected such that the left and right side arms extend along left and right cheeks of the patient, and wherein the left and right side arms connect to a headgear for holding the interface on a face of the patient.

23. The interface of claim 14, wherein a wall thickness of the seal reduces from an external side of the seal to a patient side of the seal.

24. The interface of claim 14, wherein a top wall of the outer side of the seal is uninterrupted by the first fold and the second fold and a bottom wall of the outer side of the seal is uninterrupted by the first fold and the second fold.

25. The interface of claim 14, wherein the seal has a forward side closer to the opening and a rearward side further from the opening, wherein a portion of the first stabilizing portion is located on each of the forward side and the rearward side of the first fold, and a portion of the second stabilizing portion is located on each of the forward side and the rearward side of the second fold.

26. The interface of claim 14, wherein the opening defines a length axis of the seal, wherein the first fold and the second fold are located an equal distance from the opening along the length axis.

* * * * *